US007343195B2

(12) United States Patent
Strommer et al.

(10) Patent No.: US 7,343,195 B2
(45) Date of Patent: Mar. 11, 2008

(54) METHOD AND APPARATUS FOR REAL TIME QUANTITATIVE THREE-DIMENSIONAL IMAGE RECONSTRUCTION OF A MOVING ORGAN AND INTRA-BODY NAVIGATION

(75) Inventors: Gera M. Strommer, Haifa (IL); Uzi Eichler, Haifa (IL); Liat Schwartz, Haifa (IL)

(73) Assignee: Mediguide Ltd., Haifa (IL)

( * ) Notice: Subject to any disclaimer, the term of this patent is extended or adjusted under 35 U.S.C. 154(b) by 454 days.

(21) Appl. No.: 09/949,160

(22) Filed: Sep. 7, 2001

(65) Prior Publication Data

US 2002/0049375 A1    Apr. 25, 2002

Related U.S. Application Data

(63) Continuation-in-part of application No. 09/782,528, filed on Feb. 13, 2001, which is a continuation-in-part of application No. 09/314,474, filed on May 18, 1999, now Pat. No. 6,233,476.

(51) Int. Cl.
*A61B 5/00* (2006.01)

(52) U.S. Cl. .................. 600/424; 600/415; 600/434; 600/437; 600/453

(58) Field of Classification Search ............ 600/407, 600/425, 426, 427, 437, 438, 439, 424, 415, 600/434, 453; 606/130; 378/20, 205, 69
See application file for complete search history.

(56) References Cited

U.S. PATENT DOCUMENTS

| 3,974,826 A | 8/1976 | Eggleton et al. ........... 128/2 V |
| 3,990,296 A | 11/1976 | Erikson .................... 73/67.5 H |
| 4,737,794 A | 4/1988 | Jones ....................... 342/448 |
| 5,016,642 A | 5/1991 | Dukes et al. ............... 128/696 |
| 5,152,290 A | 10/1992 | Freeland ................. 128/660.07 |
| 5,159,931 A | 11/1992 | Pini ....................... 128/660.07 |
| 5,398,691 A | 3/1995 | Martin et al. ............ 128/662.06 |
| 5,453,686 A | 9/1995 | Anderson ............... 324/207.17 |
| 5,529,070 A | 6/1996 | Augustine et al. ...... 128/660.07 |
| 5,577,502 A | 11/1996 | Darrow et al. |
| 5,588,432 A | 12/1996 | Crowley ................. 128/660.03 |
| 5,622,174 A | 4/1997 | Yamazaki |
| 5,669,385 A * | 9/1997 | Pesque et al. .............. 600/453 |
| 5,690,113 A | 11/1997 | Sliwa, Jr. et al. ....... 128/660.07 |
| 5,744,953 A | 4/1998 | Hansen .................. 324/207.17 |
| 5,787,889 A | 8/1998 | Edwards et al. ........ 128/660.07 |
| 5,806,521 A | 9/1998 | Morimoto et al. ...... 128/661.01 |
| 5,830,145 A | 11/1998 | Tenhoff ..................... 600/463 |
| 5,830,222 A | 11/1998 | Makower |
| 5,846,200 A | 12/1998 | Schwartz ................... 600/443 |
| 5,899,860 A | 5/1999 | Pfeiffer et al. ............. 600/424 |

(Continued)

Primary Examiner—Brian L. Casler
Assistant Examiner—Baisakhi Roy
(74) Attorney, Agent, or Firm—Darby & Darby P.C.

(57) ABSTRACT

Medical imaging and navigation system including a processor, a medical positioning system (MPS), a two-dimensional imaging system and an inspected organ monitor interface, the MPS including an imaging MPS sensor, the two-dimensional imaging system including an image detector, the processor being coupled to a display unit and to a database, the MPS being coupled to the processor, the imaging MPS sensor being firmly attached to the image detector, the two-dimensional imaging system being coupled to the processor, the image detector being firmly attached to an imaging catheter.

12 Claims, 40 Drawing Sheets

U.S. PATENT DOCUMENTS

| | | | |
|---|---|---|---|
| 5,913,820 A | 6/1999 | Bladen et al. ............... 600/407 |
| 5,924,989 A | 7/1999 | Polz ........................ 600/443 |
| 5,928,248 A | 7/1999 | Acker |
| 5,935,075 A | 8/1999 | Casscells .................... 600/474 |
| 5,938,606 A * | 8/1999 | Bonnefous ................. 600/437 |
| 5,949,491 A | 9/1999 | Callahan et al. ............ 348/442 |
| 5,955,879 A | 9/1999 | Durdle et al. .......... 324/207.17 |
| 5,957,844 A | 9/1999 | Dekel et al. ................. 600/439 |
| 5,967,980 A | 10/1999 | Ferre et al. ................. 600/424 |
| 5,976,088 A | 11/1999 | Urbano et al. .............. 600/443 |
| 5,993,390 A | 11/1999 | Savord et al. .............. 600/437 |
| 5,994,690 A | 11/1999 | Kulkarni et al. ............ 250/216 |
| 6,006,126 A * | 12/1999 | Cosman ...................... 600/426 |
| 6,035,856 A | 3/2000 | LaFontaine et al. |
| 6,047,080 A | 4/2000 | Chen et al. |
| 6,134,003 A | 10/2000 | Tearney et al. ............. 356/345 |
| 6,148,095 A | 11/2000 | Prause et al. |
| 6,169,917 B1 | 1/2001 | Masotti et al. |
| 6,175,669 B1 | 1/2001 | Colston et al. ............... 385/12 |
| 6,216,029 B1 * | 4/2001 | Paltieli ....................... 600/427 |
| 6,246,898 B1 | 6/2001 | Vesely et al. |
| 6,261,247 B1 * | 7/2001 | Ishikawa et al. ............ 600/587 |
| 6,317,621 B1 | 11/2001 | Graumann et al. |
| 6,321,109 B2 | 11/2001 | Ben-Haim et al. |
| 6,385,476 B1 | 5/2002 | Osadchy et al. |
| 6,390,982 B1 | 5/2002 | Bova et al. ................. 600/443 |
| 6,405,072 B1 | 6/2002 | Cosman ...................... 600/426 |
| 6,423,009 B1 * | 7/2002 | Downey et al. ............. 600/461 |
| 6,470,207 B1 * | 10/2002 | Simon et al. ............... 600/426 |
| 6,501,981 B1 * | 12/2002 | Schweikard et al. ........ 600/427 |
| 6,546,271 B1 | 4/2003 | Reisfeld |
| 6,556,695 B1 | 4/2003 | Packer et al. |
| 6,587,707 B2 * | 7/2003 | Nehrke et al. .............. 600/410 |
| 6,626,902 B1 | 9/2003 | Kucharczyk et al. |
| 7,235,084 B2 | 6/2007 | Skakoon et al. |
| 2002/0193686 A1 | 12/2002 | Gilboa |
| 2004/0097804 A1 | 5/2004 | Sobe |
| 2006/0058647 A1 | 3/2006 | Strommer et al. |
| 2006/0064006 A1 | 3/2006 | Strommer et al. |

* cited by examiner

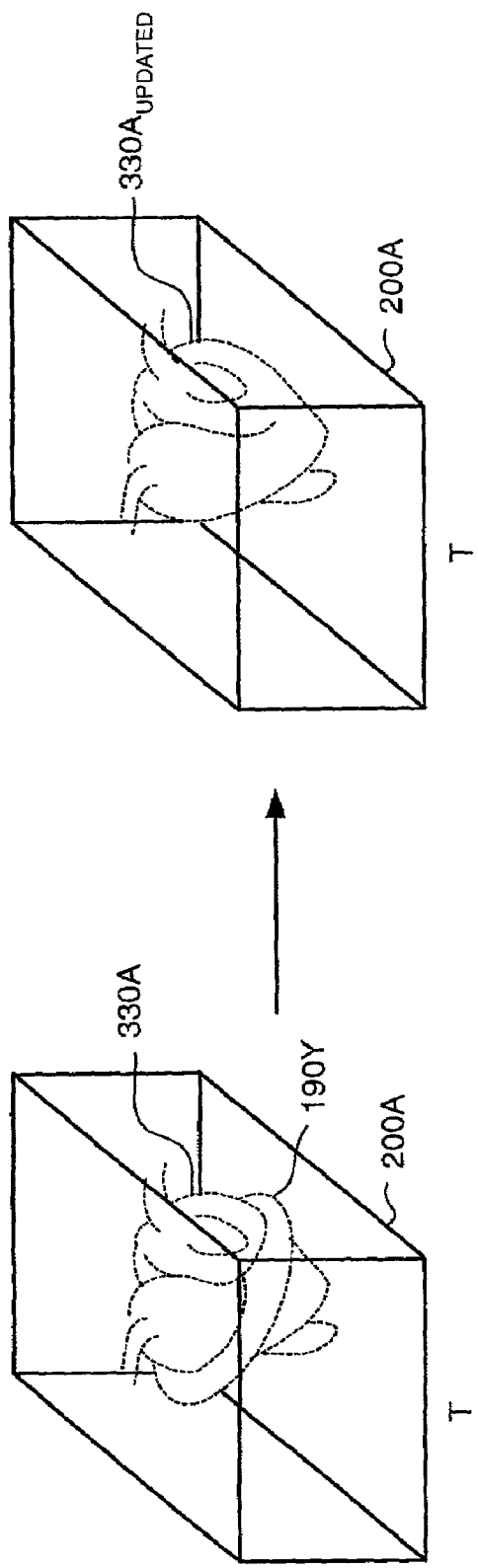
FIG. 5C
FIG. 5D
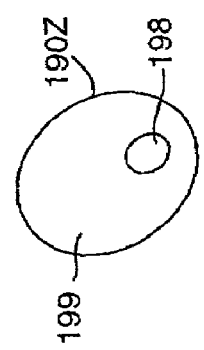

METHOD AND APPARATUS FOR REAL TIME QUANTITATIVE THREE-DIMENSIONAL IMAGE RECONSTRUCTION OF A MOVING ORGAN AND INTRA-BODY NAVIGATION

CROSS REFERENCE INFORMATION

This application is a Continuation-in-Part of application Ser. No. 09/782,528, filed Feb. 13, 2001, which is a Continuation-in-Part of application Ser. No 09/314,474, filed May 18, 1999 now U.S. Pat. N. 6,233,476.

FIELD OF THE INVENTION

The present invention relates to medical diagnostic and surgery systems and methods in general, and to methods and systems for three-dimensional medical imaging and navigation, in particular.

BACKGROUND OF THE INVENTION

Methods and systems for acquiring and presenting two-dimensional and three-dimensional images are known in the art. Three-dimensional imaging enhances modern diagnostics, therapy and surgery procedures.

A two-dimensional imaging system processes and represents two-dimensional internal body slices in static or in dynamic form on a display. A conventional two-dimensional ultrasound imaging system includes an ultrasound transducer, an image capturing module and an image-processing unit.

The ultrasound transducer is placed in close proximity to the tissue to be examined. The ultrasound transducer converts an electrical signal to ultrasonic waves and directs the waves toward the examined tissue. The ultrasonic waves are in part absorbed, dispersed, refracted and reflected. The ultrasound transducer detects the ultrasonic reflections. The ultrasound transducer converts the reflected ultrasonic waves to an electrical signal and provides it to the image-processing unit.

The image-processing unit processes the received electrical signal, thereby producing a plurality of two-dimensional images of slices of the inspected tissue. The image-capturing module captures each two-dimensional image and can provide each of them to a display or a printer.

U.S. Pat. No. 5,152,290 to Freeland, entitled "Method for recording ultrasound images to diagnose heart and coronary artery disease" is directed to a method for capturing and displaying two-dimensional ultrasound images of the heart for diagnosing heart disease, such as coronary artery disease. The method disclosed by Freeland includes the procedures of detecting an electrocardiogram (ECG) signal after peak exercise, detecting the two-dimensional images of the heart, storing selected images, each with the ECG reading at the time that the image was taken and displaying a quad-image group. The system detects and records a two-dimensional image sequence continuously at a rate of at least eight images per heartbeat.

U.S. Pat. No. 5,690,113, issued to Sliwa, Jr. et al., entitled "Method and apparatus for two-dimensional ultrasonic imaging" is directed to a method and apparatus for generating a two-dimensional ultrasonic image using a hand-held single element transducer probe, having a fixed scan-line. The system provides displaying two-dimensional ultrasonic images of the body of a patient. This system detects two-dimensional ultrasonic images, and determines the spatial location and orientation of the ultrasound transducer, at the same time. The system includes a probe with an ultrasound transducer, capable of imaging a single scan-line and a means for tracking the spatial location and orientation of the ultrasound transducer. The scan-line is fixed in an orientation and spatial position relative to the movable transducer. The system further includes a computing means, which computes the spatial location and the orientation of each scan-line as the transducer is moved. Thereby, the scan-lines are presented as a complete image. Alternatively, an electromagnetic transmitter and a receiving sensor determine the spatial orientation and position of each scan-line in free space.

A typical three-dimensional ultrasound imaging system includes a conventional two-dimensional ultrasound imaging system, a location and orientation detection system, an image processing system and a displaying system. Such systems provide three-dimensional imaging of internal organs such as the liver, kidneys, gallbladder, breast, eyes, brain, and the like.

The location and orientation detection system provides the location and orientation of ultrasound transducer. The location and orientation of each of the captured two-dimensional images are determined from the location and orientation of the transducer.

The image processing system reconstructs a three-dimensional image of the inspected organ, by processing the captured two-dimensional images, each according to the location and orientation thereof. Finally, the displaying system displays the received three-dimensional image of the inspected organ.

U.S. Pat. No. 5,787,889 issued to Edwards et al., and entitled "Ultrasound imaging with real time 3D image reconstruction and visualization" is directed to generation and visualization of three-dimensional ultrasound images. The method disclosed by Edwards includes the following procedures: acquiring data, reconstructing a volume, and visualizing an image. The system provides for achieving and visualizing three-dimensional ultrasound images with a two-dimensional ultrasound medical imaging system included therein. An operator can perform various visualization tasks on the reconstructed three-dimensional image, such as rotating the image in different viewing angles and plans.

Another type of three-dimensional imaging system, which is known in the art, is operative to produce a motion picture of the heart or the lungs. This system includes a conventional two-dimensional ultrasound imaging system, an ECG monitor, a location and orientation detection system, an image processor and a display system. The ECG monitor detects the timing signal of the heart. The ECG timing signal is used to synchronize or trigger the recording of the two-dimensional images representative of selected points in the ECG timing signal. The ultrasound transducer detects two-dimensional ultrasound images of the heart at any given moment (e.g., at a selected point of time on ECG timing signal). Each two-dimensional image represents a specific slice of the heart according to the specific activity-state thereof. The location and orientation of each of the two-dimensional images are directly determined from the location and orientation of the transducer.

The image processor reconstructs a three-dimensional image of the heart from captured two-dimensional images having the same activity-state. Finally, the display system displays a sequence of the reconstructed images, thereby presenting a three-dimensional motion picture of the heart.

U.S. Pat. No. 5,924,989 issued to Polz, and entitled "Method and device for capturing diagnostically acceptable three-dimensional ultrasound image data records", is directed to a method and a system for generating a three-dimensional image sequence of the heart. This system includes a three-dimensional ultrasound imaging system, combined with an echocardiograph. The system detects two-dimensional ultrasound images and stores each of them together with the location and orientation thereof and with the organ cycle location as provided by the echocardiogram, at the time that the image was acquired. Utilizing a special algorithm, the system reconstructs a three-dimensional image from all of the two-dimensional images having the same organ cycle location, and displays a sequence of the reconstructed three-dimensional images.

U.S. Pat. No. 5,830,145 issued to Tenhoff and entitled "Enhanced Accuracy of Three-Dimensional Intraluminal Ultrasound (ILUS) Image Reconstruction", is directed to a system and a method for imaging an organ within a body. The system of Tenhoff is described herein below, with reference to FIGS. 13A and 13B.

FIG. 13A is a schematic illustration of a system for displaying a three-dimensional image of an organ, generally referenced 10, which is known in the prior art. FIG. 13B is a schematic illustration of the trajectory of the imaging tip of the catheter of the system of FIG. 13A, inside an artery of the patient.

With reference to FIG. 13A, system 10 includes a catheter 12, an automatic pull-back device 14, a processing system 16, a chest harness 18 and a catheter tracking system (not shown). The proximal end of catheter 12 includes a handle 20. Processing system 16 includes a control console, an ultrasound transceiver and a display. Catheter 12 includes a catheter imaging tip (not shown) located at the distal end thereof. The catheter imaging system is an intraluminal ultrasound (ILUS) transducer (not shown). The catheter tracking system includes at least one tracking transducer (not shown), mounted on catheter 12 and typically adjacent the catheter imaging tip. The catheter tracking system further includes a plurality of reference frame transducers located within chest harness 18. Each of the tracking transducers and the reference frame transducers, is an ultrasound transducer. The reference frame transducers define the origin of a global coordinate system. In another embodiment of the patent, the catheter imaging system is an optical coherence tomography (OCT) imaging system.

Handle 20 is coupled to automatic pull-back device 14. The reference frame transducers are coupled to processing system 16 by wires 24. The tracking transducers are coupled to processing system 16 by wires 26. The catheter imaging system is coupled to processing system 16 by wires 28. Automatic pull-back device 14 is coupled to processing system 16 by wires 30.

The operator (not shown) enters catheter 12 in the body of a patient 22 through the femoral artery and positions catheter 12 within a region of interest (e.g., the coronary arteries). The catheter imaging system provides a plurality of two-dimensional images (e.g., echographic images in case of an ILUS transducer) of the area which surrounds the catheter imaging tip, when the catheter imaging tip is located in the region of interest.

The catheter imaging system is carried through a pull-back sequence, optionally using automatic pull-back device 14. The echographic data sets obtained during pull-back, provide the necessary input to produce an image to be displayed on the display. During the pull-back of the catheter imaging tip, processing system 16 records the position (X, Y, Z) and the time at each interval for which data is recorded.

The angulation in three dimensional space of the catheter imaging tip, for each image, is determined by using the coordinates of one or more of the tracking transducers. A pair of transducers marks the location of the catheter imaging tip during the pull-back. The pair of closely spaced transducers define a line which calculates the tangent to the curve defined by the catheter imaging tip at that point. The tangent is calculated by the line defined by the two or more points determined by the location of the tracking transducers.

In another embodiment of the patent, a single marker transducer is employed to mark the location of the catheter imaging tip during pull-back. In this case, the tangent is calculated by the line through two points determined by the successive locations of the marker transducer at two positions during the pull-back.

Processing system 16 uses the coordinates (X, Y, Z) of each echographic image acquired along the catheter pull-back path, in conjunction with the time data, to reconstruct a three-dimensional image. Each three-dimensional image is reconstructed by stacking the echographic images around the catheter pull-back trajectory.

With further reference to FIG. 13B, processing system 16 (FIG. 13A) generates a trajectory 50 of the imaging tip of catheter 12 during pull-back and the display displays trajectory 50 with reference to the origin of the global coordinate system. Trajectory 50 is defined by a plurality of points in the global coordinate system, such as points 52, 54, 56, 58, 60, 62, 64, 66 and 68. Each of the points 52, 54, 56, 58, 60, 62, 64, 66 and 68 corresponds to a different position of the catheter imaging tip during pull-back.

However, it is noted that during the pull-back sequence, the artery constantly moves to different positions such as positions 70, 72 and 74, and the location and orientation of the artery with respect to the origin of the global coordinate system, changes. Thus, trajectory 50 of catheter 12 does not represent the true trajectory of catheter 12 within the artery and trajectory 50 is substantially inaccurate.

Optical Coherence Tomography (OCT) is a general name for a method optically scans through tissue at very high resolution. OCT measures the intensity of back-reflected infrared light and yields imaging resolution, which is 5-25 times greater than other current clinical imaging technologies, such as ultrasound.

U.S. Pat. No. 6,134,003 to Tearney et al., entitled "Method and apparatus for performing optical measurements using a fiber optic imaging guidewire, catheter or endoscope", U.S. Pat. No. 6,175,669 to Colston et al., entitled "Optical coherence domain reflectometry guidewire" and U.S. Pat. No. 5,994,690 to Kulkami et al., entitled "Image enhancement in optical coherence tomography using deconvolution" are all directed to methods and system using OCT imaging technology.

Intra-vascular plaques may be prone to rupture and may provoke fatal vessel obstruction. These plaques often exhibit a different temperature than other inner vessel structures and hence, can be detected and consequently treated according to a temperature map of the inner layers of the vessel. Methods and systems for intra-vascular temperature mapping are known in the art, and are conventionally based on Infrared technology, using optic fibers, which are inserted into the blood vessel, for detecting "hot" plaques. This technique is called thermography. U.S. Pat. No. 5,935,075 to Casscells et al., entitled "Detecting Thermal Discrepancies in Vessel Walls" is directed to a system for analyzing optical radiation in blood vessels, which attempts to detect "hot" plaques.

SUMMARY OF THE PRESENT INVENTION

It is an object of the present invention to provide a novel method and system for medical in-vivo invasive probing. In accordance with the present invention, there is thus provided a medical imaging and navigation system. The system includes a processor, a display unit, a database, a medical positioning system (MPS), a two-dimensional imaging system, an inspected organ monitor interface, and a superimposing processor.

The MPS includes a transducer MPS sensor and a surgical tool MPS sensor. The two-dimensional imaging system includes an imaging transducer. The processor is coupled to the display unit, the database, the MPS, the two-dimensional imaging system, the inspected organ monitor interface, and to the superimposing processor. The inspected organ monitor interface is further coupled to an organ monitor. The surgical tool MPS sensor is firmly attached to a surgical tool. The transducer MPS sensor is firmly attached to the imaging transducer. The organ monitor monitors an organ timing signal associated with an inspected organ. The system reconstructs a plurality of three-dimensional images from a plurality of detected two-dimensional images, according to the respective location and orientation of each two-dimensional image and its position within the inspected organ timing signal. Since the all of the MPS sensors belong to the same MPS system, the system provides the location and orientation of the surgical tool, within the same coordinate system of the detected two-dimensional images.

In accordance with another aspect of the present invention, there is thus provided a medical imaging and navigation system. The system includes a processor, a display unit, a database, an MPS, an inspected organ monitor interface and a superimposing processor. The processor is coupled to the display unit, the database, the MPS, the inspected organ monitor interface and to the superimposing processor. The inspected organ monitor interface is coupled to an organ monitor. The MPS includes a surgical tool MPS sensor being firmly attached to a surgical tool. The organ monitor monitors an organ timing signal associated with an inspected organ. This system is adapted to operate on pre-stored images.

In accordance with a further aspect of the present invention, there is thus provided a method for displaying an image sequence of a moving inspected organ. The method includes the procedures of detecting an organ timing signal of the inspected organ, detecting a plurality of two-dimensional images of the inspected organ using an image detector, and detecting the location and orientation of the image detector. The method further includes the procedures of associating each of the two-dimensional images with the image detector location and orientation and with the detected organ timing signal, and reconstructing a plurality of three-dimensional images from the two-dimensional images. The method further includes the procedures of selecting one of the three-dimensional images according to a real-time reading of the organ timing signal, and displaying the selected three-dimensional image.

In accordance with another aspect of the present invention, there is thus provided a method for displaying an image sequence of a moving inspected organ. The method includes the procedures of detecting an organ timing signal of the inspected organ, and selecting one of previously stored three-dimensional images according to a real-time reading of the organ timing signal. The method further includes the procedures of detecting the location and orientation of a surgical tool, superimposing a representation of the surgical tool onto the selected three-dimensional image, and displaying the superimposed three-dimensional image.

In accordance with a further aspect of the present invention, there is thus provided a method for displaying an image sequence of a moving inspected organ. The method includes the procedures of detecting an organ timing signal of the inspected organ, detecting the location and orientation of a point of view of a user and selecting one of previously stored three-dimensional images according to a real-time reading of the organ timing signal. The method further includes the procedures of rendering the selected three-dimensional image according to the detected location and orientation of the point of view and displaying the selected three-dimensional image.

In accordance with another aspect of the present invention, there is thus provided a method for displaying an image sequence of a moving inspected organ. Each image in the image sequence is associated with the location and orientation of the image within a predetermined coordinate system. The method includes the procedures of detecting an organ timing signal of the inspected organ, selecting one of a previously stored two-dimensional images according to a real-time reading of the organ timing signal and displaying the selected two-dimensional image. This system is adapted for a two-dimensional imaging and displaying environment.

In accordance with a further aspect of the present invention, there is thus provided a medical imaging and navigation system. The medical imaging and navigation system includes a processor, an MPS, a two-dimensional imaging system and an inspected organ monitor interface. The MPS includes an imaging MPS sensor and the two-dimensional imaging system includes an image detector. The processor is coupled to a display unit, the inspected organ monitor interface, a database, and to the MPS. The inspected organ monitor interface is further connected to an organ monitor. The imaging MPS sensor is firmly attached to the image detector. The two-dimensional imaging system is coupled to the processor. The image detector is firmly attached to an imaging catheter. The image detector is an optical coherence tomography detector, an ultrasound detector, a magnetic resonance imaging detector, thermography detector, and the like.

The image detector detects two-dimensional images of an inspected organ. The organ monitor monitors an organ timing signal associated with the inspected organ. The imaging MPS sensor provides information respective of the location and orientation of the image detector, to the MPS. The processor associates each of the detected two-dimensional images with the respective location and orientation information and with the organ timing signal, and reconstructs a three-dimensional image of the inspected organ, according to the two-dimensional images.

In accordance with another aspect of the present invention, there is thus provided a medical imaging and navigation system. The medical imaging and navigation system includes a processor, an MPS and an inspected organ monitor interface. The MPS includes a catheter MPS sensor. The processor is coupled to a display unit, the MPS, an inspected organ monitor interface and to a database. The inspected organ monitor interface is coupled to an organ monitor. The catheter MPS sensor is firmly attached to a surgical tool and the surgical tool is firmly attached to a surgical catheter.

The organ monitor monitors an organ timing signal associated with the inspected organ. The catheter MPS sensor provides information respective of the location and orientation of the surgical tool, to the MPS. The processor reconstructs a three-dimensional image of the inspected organ, according to the location and orientation information associated with the two-dimensional images, and according to a real time organ timing signal reading. The processor superimposes a representation of the surgical tool, and a representation of a trajectory of the image detector on the reconstructed three-dimensional image, according to the location and orientation information respective of the surgical tool.

In accordance with a further aspect of the present invention, there is thus provided a graphical user interface. The graphical user interface includes a plurality of windows, wherein each window presents an image of the inspected organ. The image is selected according to the organ timing signal. The image can be an external three-dimensional image of the inspected organ, an internal three-dimensional image thereof, an historical two-dimensional image thereof, a real time two-dimensional image of the portion of the body of the patient which includes the inspected organ, and the like. For example, a projection of the external three-dimensional image, a representation of a surgical tool and a representation of a trajectory of an imaging catheter are superimposed on the real time two-dimensional image. Furthermore, a representation of the surgical tool and a representation of the trajectory, are superimposed on the internal three-dimensional image. The ECG of the patient is also displayed, wherein the operator can play a pseudo-video three-dimensional image of the inspected organ, according to the ECG, forward or backward in time or at a selected point in the ECG.

In accordance with another aspect of the present invention, there is thus provided a method for displaying the occluded regions of the inspected organ. The method includes the procedures of comparing a plurality of occlusion values of the inspected organ, with a selected occlusion value, determining the occluded regions according to the outcome of the comparison and producing a presentation of the occluded regions. The operator selects an occlusion threshold and those occlusion regions of the inspected organ whose occlusion values are greater than the selected occlusion threshold, are superimposed on a three-dimensional image of the inspected organ.

In accordance with a further aspect of the present invention, there is thus provided a method for displaying an image sequence of a moving inspected organ. The method includes the procedures of detecting an organ timing signal of the inspected organ and detecting a plurality of two-dimensional images of the inspected organ by using an image detector. The method further includes the procedures of detecting a real time two-dimensional image of the inspected organ, detecting the location and orientation of the image detector, and detecting the location and orientation of a surgical tool.

The method further includes the procedures of associating each of the two-dimensional images with the image detector location and orientation and with the detected organ timing signal, and reconstructing a plurality of three-dimensional images from the two-dimensional images. The method further includes the procedures of selecting one of the three-dimensional images according to a real-time reading of the organ timing signal and displaying the selected three-dimensional image. The organ timing signal defines an organ timing signal cycle. Each of the three-dimensional images is reconstructed from selected two-dimensional images, wherein the selected two-dimensional images correspond to a selected position within the organ timing signal cycle. The processor superimposes a projection of the reconstructed three-dimensional image of the inspected organ and a representation of the surgical tool, on the detected real time two-dimensional image of the inspected organ.

In accordance with another aspect of the present invention, there is thus provided a method for reconstructing an image. The method includes the procedures of determining translated coordinates for an auxiliary two-dimensional image, which belongs to an activity-state other than a selected activity-state and associating the auxiliary two-dimensional image with the selected activity-state, according to the translated coordinates. The processor reconstructs the three-dimensional image from the auxiliary two-dimensional images which belong to activity-states other than the selected activity-states, as well as those two-dimensional images which belong to the selected activity-state. Thus, a much more detailed image is obtained, if only the images, which belong to the selected activity-state, were used.

BRIEF DESCRIPTION OF THE DRAWINGS

The present invention will be understood and appreciated more fully from the following detailed description taken in conjunction with the drawings in which:

FIG. 5C is a schematic illustration of a selected three-dimensional volume of FIG. 5A, going through a procedure of image updating;

FIG. 5D is a schematic illustration of a two-dimensional image, which includes foreign object information;

DETAILED DESCRIPTION OF PREFERRED EMBODIMENTS

Figure 1:
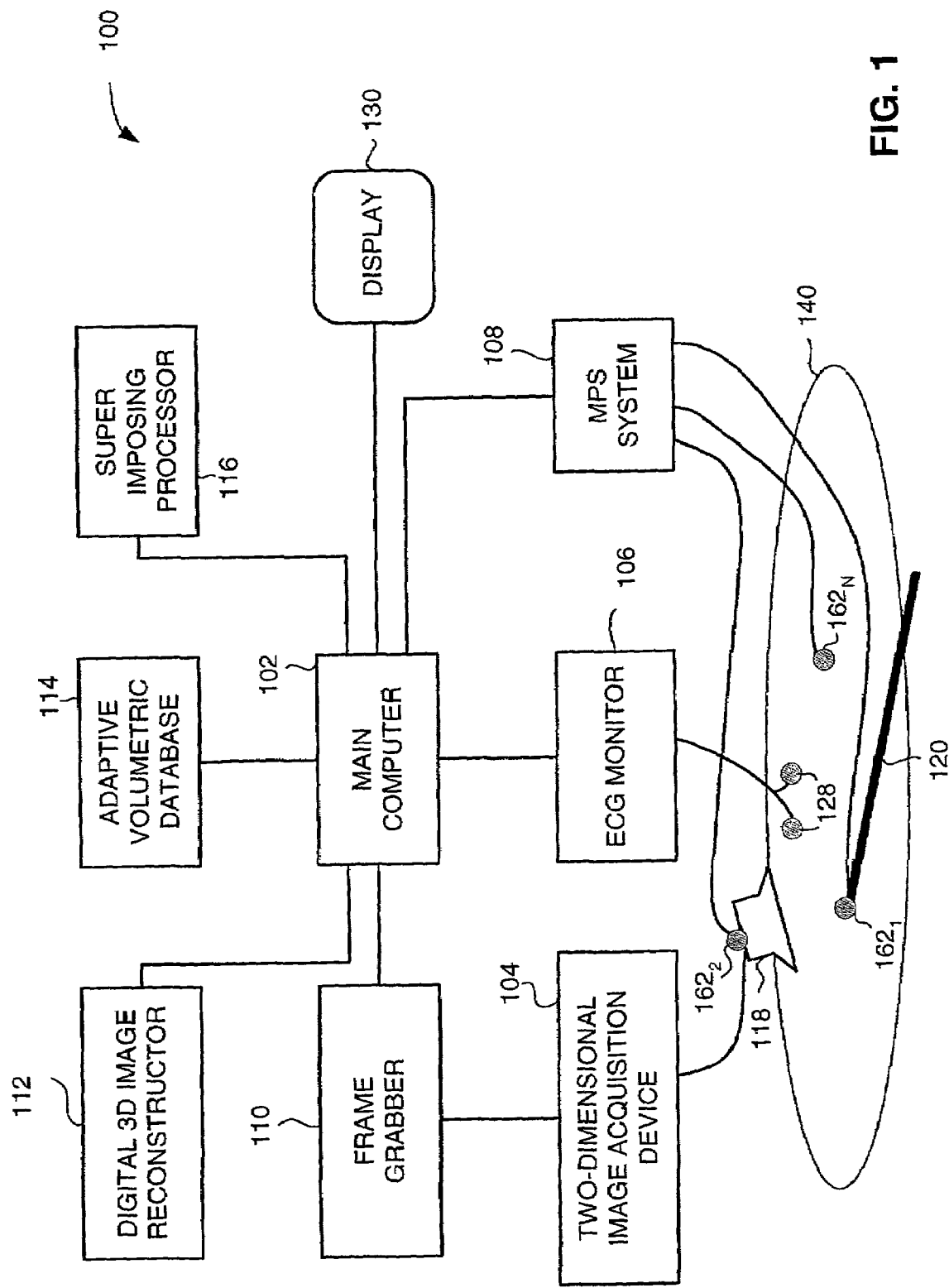
FIG. 1 is a schematic illustration of a multi functional three-dimensional imaging system, constructed and operative in accordance with a preferred embodiment of the present invention.

The present invention overcomes the disadvantages of the prior art by providing methods and systems for constructing and displaying three-dimensional images of moving organs, synchronously with the movement of these organs and synchronously with an invasive tool, such as a catheter. According to a preferred embodiment, the three-dimensional images and the presentation of the invasive tool, all reside within a single coordinate system, and no registration of a plurality of coordinate systems is required.

According to one aspect of the invention there is provided a pseudo real time imaging system, for minimal invasive surgery. This system includes a two-dimensional image acquisition system, a medical positioning system (MPS) which is basically a location and orientation detection system, a specific organ monitor and an image processing system. The location and orientation detection system includes at least three sensors. The first sensor is mounted on the image detector of the two-dimensional image acquisition system. The second sensor is mounted on the minimal invasive surgery tool. The third sensor is attached to the body of the patient for reference. Attaching the third sensor to the body of the patient during all of the procedures of the method of the disclosed technique, assures that both the sensor of the image detector and the sensor of the surgical tool, as well as additional sensors which are attached to further modules of the system of the invention, remain in a single coordinate system at all times.

The system acquires two-dimensional images at a rate, faster than the organ cycle frequency, and preferably equal to the organ cycle frequency multiplied by a natural number. The system records each two-dimensional image, acquired by the image detector, in association with the detected location and orientation thereof, and with the organ timing signal reading, as detected by the organ monitor. It is noted that the system operates under the assumption that the detected organ is characterized by a cyclic behavior, and that a reading in one cycle is likely to be detected in subsequent cycles.

The imaging system reconstructs a three-dimensional image from all of the recorded two-dimensional images, which have the same organ timing signal reading (from different cycles). When the reconstructed three-dimensional images include sufficient information, the system displays a sequence of these three-dimensional images, synchronized with a real-time reading of the organ timing signal, thereby providing a real-time visualization of the inspected organ. At the same time, the system continues to acquire additional two-dimensional images and to update and elaborate the existing three-dimensional image. Hence, the quality of the displayed sequence of three-dimensional images, constantly improves.

At this point, the physician can insert a minimal invasive surgical tool into the body of the patient. The system detects the location and orientation of the MPS detector mounted on the surgical tool and super-imposes a representation thereof, on the currently displayed three-dimensional image.

The system detects movements of the patient using the MPS detector, which is attached to the patient. These movements shift the coordinate system of the detected organ relative to the coordinate system in which the two-dimensional images were acquired and the three-dimensional images are reconstructed. The system utilizes the patient MPS reading both for placing all the acquired two-dimensional images in a moving coordinate system defined by the location of the inspected organ, and for placing and orienting the surgical tool, in that same moving coordinate system.

According to another aspect of the invention, by removing the surgical tool, the system can be used merely as a pseudo real-time imaging system, used for diagnostic purposes. According to a further aspect of the invention, the system displays the three-dimensional image sequence, using semi transparent stereoscopic goggles, which have an MPS sensor attached thereto. The system uses the goggles MPS sensor to set the location and orientation of the goggles, within the coordinate system of the patient. Accordingly, the system produces a visualization of the three-dimensional image sequence, which is perceived by the physician, as being located at the same place of the organ.

The following is an example of a system and method for image acquisition, playback and minimal invasive surgery, where the inspected organ is a heart. Reference is now made to FIG. 1, which is a schematic illustration of a multi functional three-dimensional imaging system, generally referenced 100, constructed and operative in accordance with a preferred embodiment of the present invention. In the example set forth in FIG. 1, system 100 is adapted for producing a three-dimensional image sequence of the heart and playing it in real time synchronicity, with the motion of the heart.

Three-dimensional imaging system 100 includes, a main computer 102, a two-dimensional image acquisition device 104, an ECG monitor 106, a medical positioning system (MPS) 108, a frame grabber 110, a digital three-dimensional image reconstructor (D3DR) 112, an adaptive volumetric database (AVDB) 114, a superimposing processor 116, a surgical tool 120, a plurality of MPS sensors $162_1$, $162_2$ and $162_N$, and a display 130.

Two-dimensional image acquisition device 104 provides a two-dimensional image of an area within the body of the patient. Two-dimensional image acquisition device 104 can be of any type known in the art, such as ultra-sound, inner-vascular ultra-sound, X-ray, computerized tomography, nuclear magnetic resonance, positron-emission tomography, single-photon-emission tomography, and the like.

Two-dimensional image acquisition device 104 includes an image transducer 118. ECG-monitor continuously detects an electrical timing signal of the heart during inspection or surgery procedure, by employing a plurality of ECG-electrodes 128.

Main computer 102 is coupled to ECG monitor 106, MPS system 108, frame grabber 110, D3DR 112, superimposing processor 116, AVDB 114 and to display 130. Two-dimensional image acquisition device 104 is coupled to frame grabber 110. MPS system 108 includes an MPS transmitter (not shown) and MPS sensors $162_1$, $162_2$ and $162_N$.

Figure 2A:
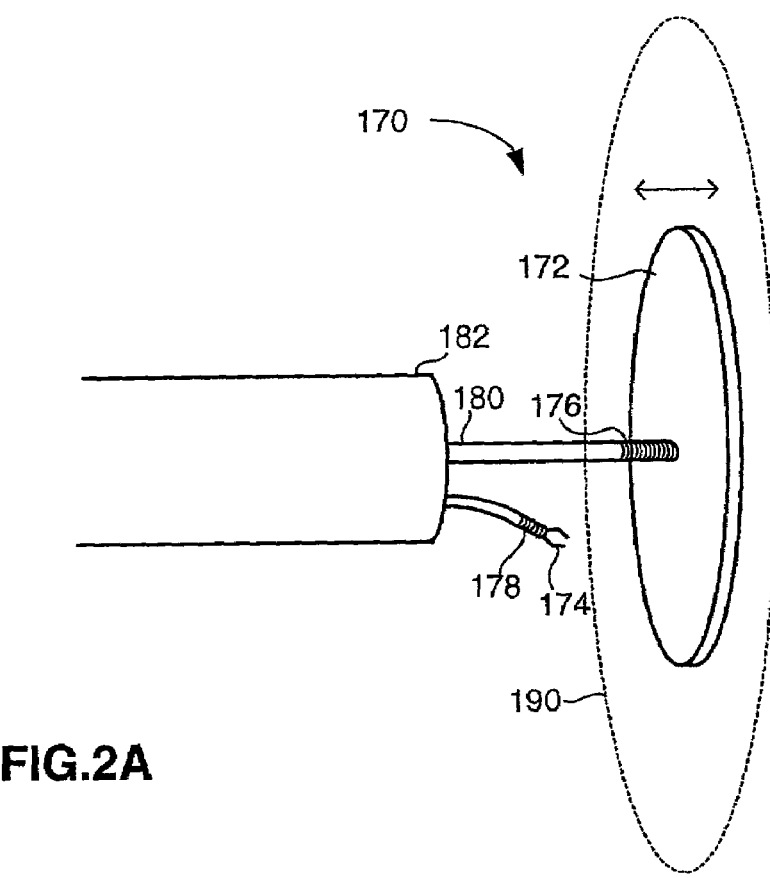
FIG. 2A is an illustration in perspective of an inner-body radial ultrasound imaging system, constructed and operative in accordance with another preferred embodiment of the present invention.
Figure 2B:
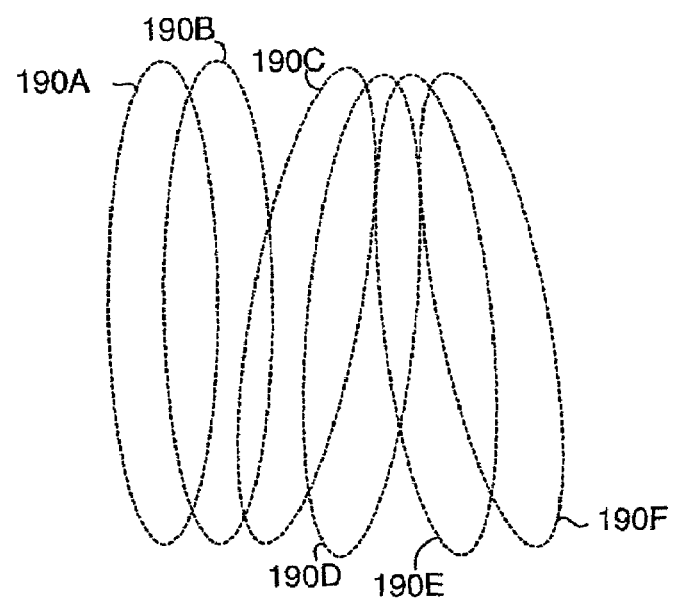
FIG. 2B is an illustration in perspective of a plurality of radial two-dimensional images of the walls of an inspected vessel.
Figure 2C:
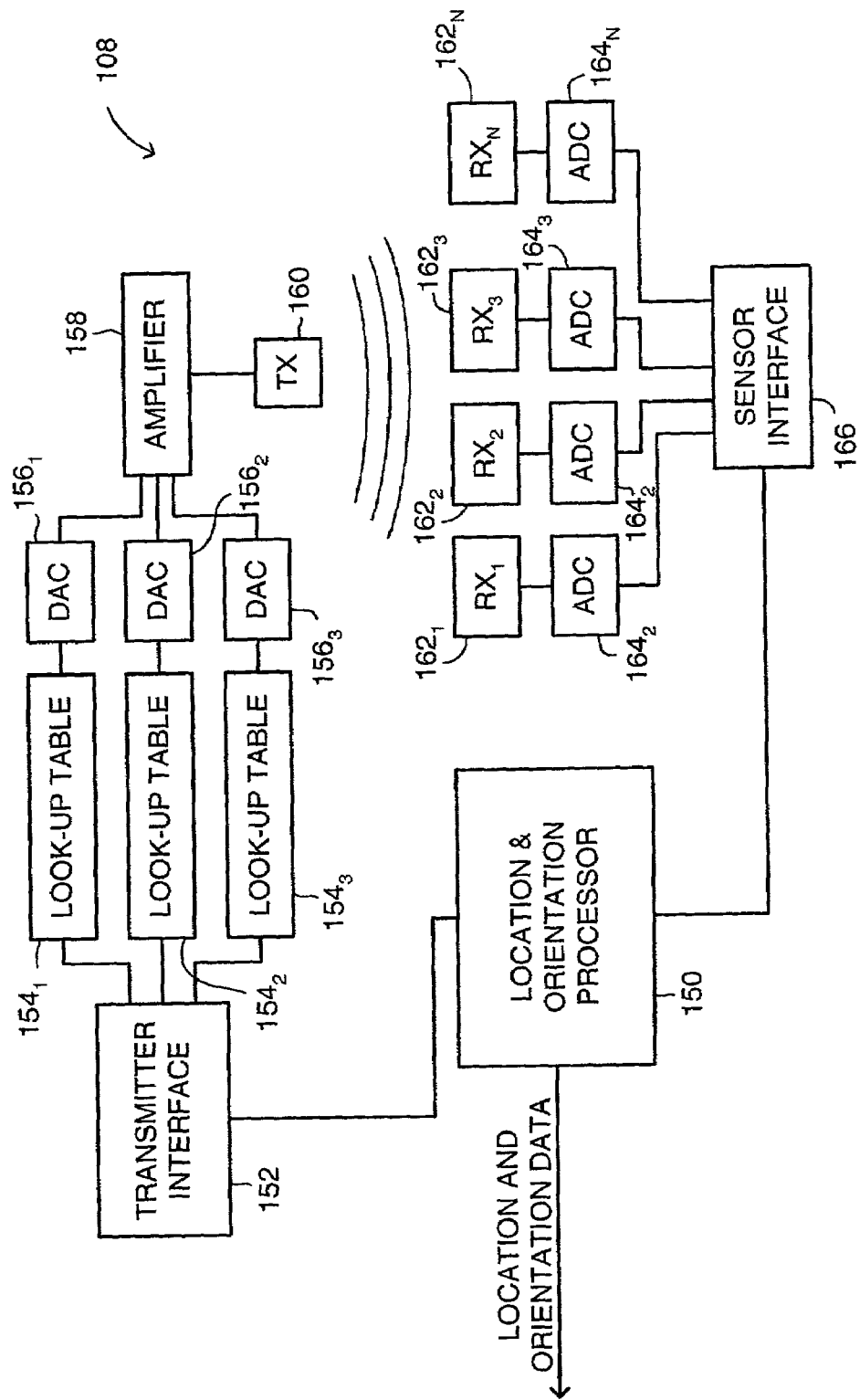
FIG. 2C is a schematic illustration in detail of the MPS system of FIG. 1, constructed and operative in accordance with a further preferred embodiment of the present invention.

Reference is further made to FIG. 2C, which is a schematic illustration in detail of MPS system 108, constructed and operative in accordance with another preferred embodiment of the present invention. MPS system 108 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is coupled to location and orientation processor 150 and to look-up table units $154_1$, $154_2$ and $154_3$. DAC units $156_1$, $156_2$ and $156_3$ are coupled to a respective one of look-up table units $154_1$, $154_2$ and $154_3$ and to amplifier 158. Amplifier 158 is further coupled to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively.

Analog to digital converters (ADC) $164_1$, $164_2$, $164_3$ and $164_N$ are respectively coupled to sensors $162_1$, $162_2$, $162_3$ and $162_N$ and to sensor interface 166. Sensor interface 166 is further coupled to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ coupled thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150.

Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

Referring back to FIG. 1, image transducer 118 detects a plurality of two-dimensional images, each representing a slice of the inspected organ (i.e., the heart). Each of these two-dimensional images has a different spatial location and orientation.

Frame grabber 110 grabs each detected two-dimensional image and provides it to main computer 102. MPS system 108 receives and processes data related to the location and orientation of surgical tool 120 via MPS sensor $162_1$ and processes data related to the location and orientation of image transducer 118 via MPS sensor $162_2$.

MPS system 108 further receives and processes data related to the location and orientation of the body of a patient, via MPS sensor $162_N$. It is noted that MPS sensor $162_N$ is used as reference in case the patient moves. MPS sensor $162_N$ is generally attached to an inspected area of a patient body (reference 140). It is noted that MPS system 108 can include additional MPS sensors, to be used as further references, thereby enhancing the performance of system 100. It is noted however that other methods for assigning a reference point can be used such as initial referencing between all of the MPS sensors and strapping the patient during the entire procedure, analyzing the acquired images and identifying a recurring visual point or section therein for each of the MPS sensors other than the one for the transducer, and the like.

MPS system 108 produces predetermined electromagnetic fields using the MPS transmitter. Each of the MPS sensors $162_1$, $162_2$ and $162_N$ includes electromagnetic field detection elements, such as coils, for detecting the electromagnetic fields produced by MPS system 108.

MPS system 108 processes the detected electromagnetic fields and provides an indication of the three-dimensional location and orientation of MPS sensors $162_1$, $162_2$ and $162_N$. Hence, MPS system 108 is operative to determine the location and orientation of image transducer 118, surgical tool 120 and a selected point on the body of the patient.

The location and orientation of each of the captured two-dimensional images are directly derived from the location and orientation of image transducer 118. Hence, by determining the location and orientation of MPS sensor $162_2$, MPS system 108 can determine the location and orientation of each of the two-dimensional images captured by image transducer 118.

ECG monitor 106 obtains and represents an electrical timing signal (ECG—electrocardiogram) of the inspected heart. It is noted that ECG is a heart timing signal, which includes ECG cycles and represents the propagation of electrical currents through specific regions of the heart. The duration of an ECG cycle (or cardiac cycle) is defined as the time between two subsequent heart contractions. ECG is detected using at least two ECG-electrodes, which are placed on selected areas of the body of the patient (e.g., the arms, legs, chest, abdomen, and the like).

ECG-electrodes 128 continuously obtain an electrical signal from the heart and provide this signal to ECG monitor 106. ECG monitor 106 amplifies the received electrical signal, produces a graphic line tracing the electrical activity of the heart, as a function of the time, and provides this data in digital format to main computer 102.

Main computer 102 receives each of the two-dimensional images, the respective three-dimensional location and orientation of that specific two-dimensional image and the organ timing signal of the heart at the time the image was captured. Main computer 102 can further receive the three-dimensional location and orientation of surgical tool 120. Main computer 102 associates each detected two-dimensional image, with the location and orientation information and the heart-timing signal.

When the surgical tool 120 is located within the inspected organ, a two-dimensional image can include a sliced representation of a portion thereof. Main computer 102 receives the location and orientation of MPS sensor $162_1$, which is attached to the surgical tool and can extrapolate the location and orientation of a larger portion of the surgical tool, in case that portion of the surgical tool is substantially rigid. Hence, main computer 102 can determine if that portion of surgical tool 120 is located within an area of the acquired two-dimensional image. Main computer 102 can discard this area, while updating the three-dimensional image, to which the two-dimensional image belongs.

D3DR 112 reconstructs a three-dimensional image from captured two-dimensional images, having the same activity-state (e.g., for each determined point of the heart timing cycle) and from the three-dimensional location and orientation data associated with each of the images.

AVDB 114 contains the reconstructed three-dimensional images of the inspected organ, along with the activity-state associated therewith and with the location and orientation of the coordinate system thereof. The detected ECG sequence is further used for synchronously playing back the three-dimensional images, where every three-dimensional image is displayed when the activity-state associated therewith is substantially equal to the real-time detected activity-state of the inspected organ.

In case surgical tool 120 is inserted in the heart, superimposing processor 116 can add the three-dimensional location and orientation of surgical tool 120 to the reconstructed three-dimensional image. Alternatively, main computer 102 can extrapolate the shape of surgical tool 120 in the coordinate system of the reconstructed three-dimensional image.

Display 130 presents a three-dimensional motion picture of the inspected organ in synchrony therewith, which can be considered a pseudo real-time simulation thereof. It is noted that main computer 102 can determine the display reference coordinate system to be any of the following:

The coordinate system of the patient, where the body of the patient is still and the inspected organ and the surgical tool, move.

The coordinate system of the inspected organ, where the inspected organ is still, and surgical tool and the rest of body of the patient, move. It is noted that this viewing coordinate system can be extremely useful in cases where the inspected organ exhibits rapid movement.

The coordinate system of the surgical tool, where the surgical tool is still, and the inspected organ as well as the rest of the body of the patient, move.

Reference is now made to FIGS. 2A and 2B. FIG. 2A is an illustration in perspective of an inner-body radial ultrasound imaging system, generally referenced 170, constructed and operative in accordance with a further preferred embodiment of the present invention. FIG. 2B is an illustration in perspective of a plurality of radial two-dimensional images of the inner walls of an inspected vessel, generally referenced 190.

System 170 includes an Inner-body radial image transducer 172, a surgical tool (i.e., typically a minimal invasive surgical device) 174, MPS sensors 176 and 178, a mounting catheter 180 and a dilation catheter 182. It is noted that inner-body radial ultrasound imaging system 170 can be replaced with alternative ultrasound systems such as an inner-vascular ultrasound system (IVUS) which is discussed in further detail in FIG. 12 herein below, or other types of two-dimensional imaging systems.

Radial image transducer 172 is mounted on mounting catheter 180, which is further inserted in dilation catheter 182. MPS sensor 176 is located at a tip of mounting catheter 180 adjacent to radial image transducer 172. Mounting catheter 180 is inserted in dilation catheter 182. MPS sensor 178 is located in close proximity to the tip of surgical tool 174. Surgical tool 174 is further inserted in dilation catheter 182.

Radial image transducer 172 detects a plurality of two-dimensional images of different areas of the inspected organ (such as two-dimensional images 190A, 190B, 190C, 190D, 190E and 190F (FIG. 2B). MPS system 108 (FIG. 1) detects the location and orientation of radial image transducer 172, using sensor 176. MPS system 108 (FIG. 1) further detects the location and orientation of surgical tool 174, using sensor 178. The location and orientation of two-dimensional images 190A, 190B, 190C, 190D, 190E and 190F (FIG. 2B) are directly derived from the location and orientation of the transducer 172.

As can be seen in FIG. 2B, each of the detected two-dimensional images 190A, 190B, 190C, 190D, 190E and 190F is a two-dimensional representation of a different peripheral portion of the inspected area within the inspected organ and its vicinity. Radial image transducer 172 provides the detected two-dimensional images 190A, 190B, 190C, 190D, 190E and 190F to two-dimensional image acquisition device 104 (FIG. 1). The System 100 associates each two-dimensional image, with the location and orientation thereof.

Figure 3:
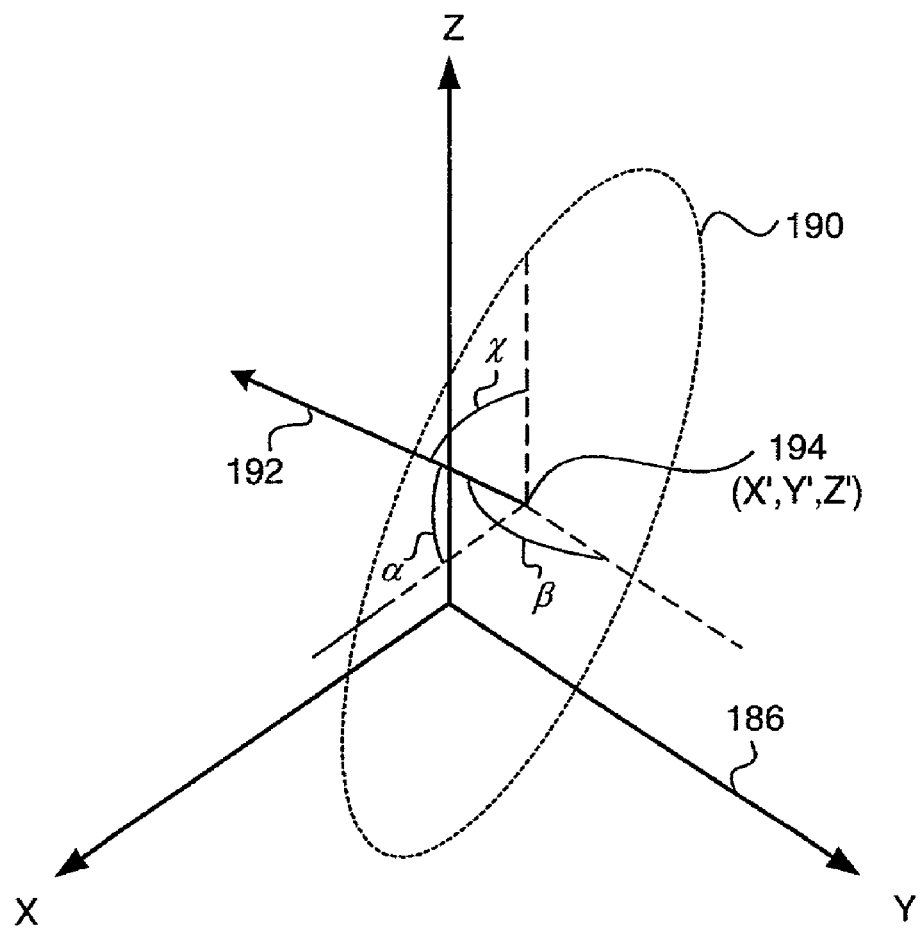
FIG. 3 is a schematic illustration of a two-dimensional image in a given coordinate system.

Reference is now made to FIG. 3, which is a schematic illustration of a two-dimensional image, generally referenced 190, in a given coordinate system, generally referenced 186. FIG. 3 is mainly used for visualizing the terms "location" and "orientation" of the two-dimensional image 190 in coordinate system 186.

The location and orientation of each two-dimensional image 190 are determined in the coordinate system 186 (X, Y and Z). System 100 determines a selected point in each captured two-dimensional image, which is to be the reference point for that image. In the example set forth in FIG. 3, the center of the image is determined to be the reference location point thereof. A unit vector extending from that point, perpendicular to the plane of that image determines the orientation of that image.

Each detected two-dimensional image 190 is taken in a specific location (X', Y' and Z') and a specific orientation (angles ☐, ☐ and ☐). Vector 192 extends from a selected point 194 of the image 190. The coordinates of this point X', Y' and Z' determine the specific three-dimensional location of the image 190 in the coordinate system 186. Angles ☐, ☐ and ☐ are the angles between the vector 192 and each of the axes X, Y and Z, accordingly. Thereby, vector 192 determines the specific three-dimensional orientation of the image 190 in coordinate system 186.

Figure 4:
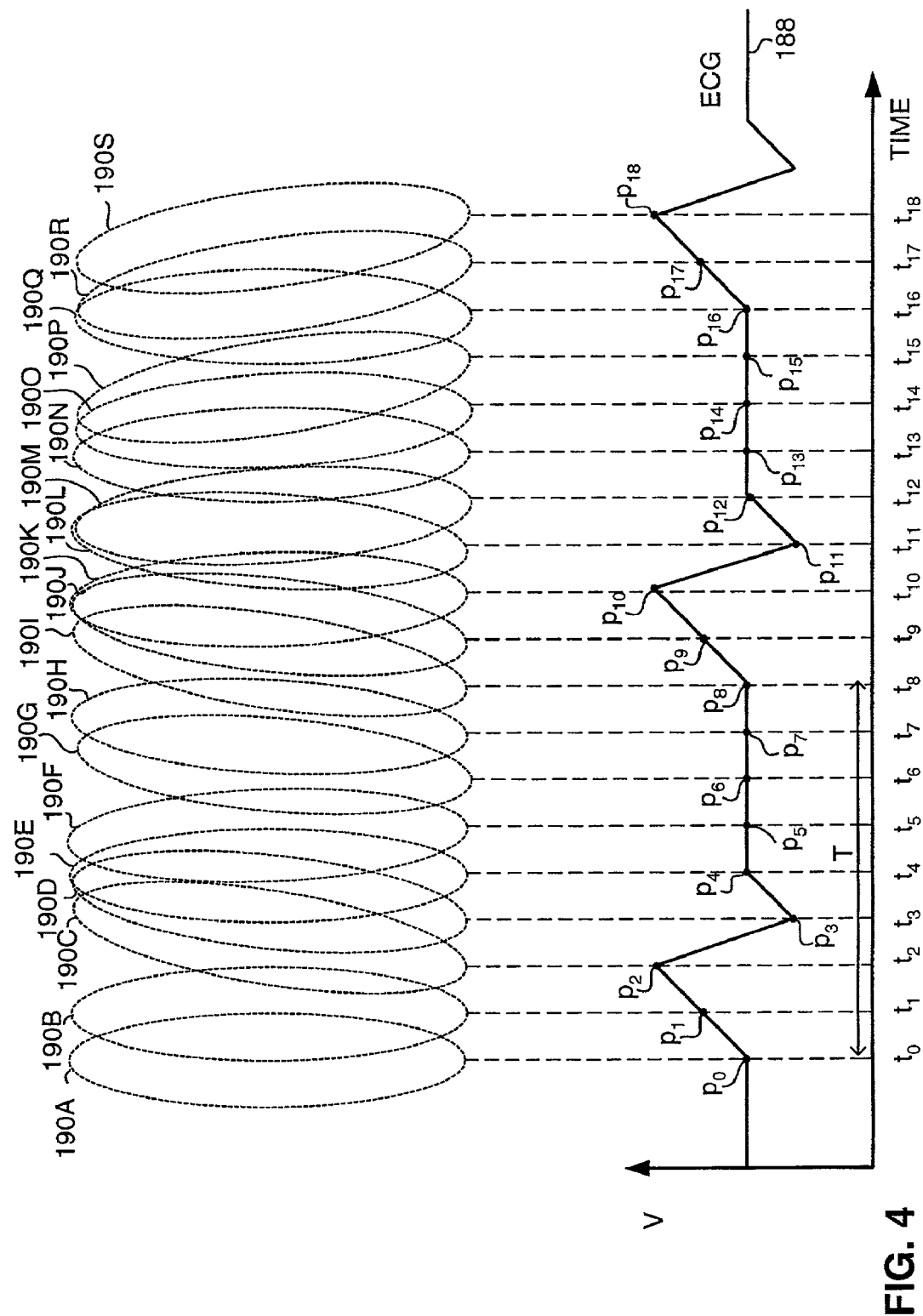
FIG. 4 is an illustration in perspective of a plurality of two-dimensional images and an organ timing signal.

Reference is now made to FIG. 4, which is an illustration in perspective of a plurality of two-dimensional images, generally referenced 190, and an organ timing signal, generally referenced 188. In the example set forth in FIG. 4, the organ timing signal is an ECG signal.

The ECG signal can be used for synchronizing the detection procedure of two-dimensional images 190A, 190B, 190C, 190D, 190E, 190F, 190G, 190H, 190I, 190J, 190K, 190L, 190M, 190N, 190O, 190P, 190Q, 190R and 190S, where each image is taken at a predetermined position in the organ timing signal. Two-dimensional images 190A, 190B, 190C, 190D, 190E, 190F, 190G, 190H, 190I, 190J, 190K, 190L, 190M, 190N, 190O, 190P, 190Q, 190R and 190S are detected at predefined points in time $t_0$, $t_1$, $t_2$, $t_3$, $t_4$, $t_5$, $t_6$, $t_7$, $t_8$, $t_9$, $t_{10}$, $t_{11}$, $t_{12}$, $t_{13}$, $t_{14}$, $t_{15}$, $t_{16}$, $t_{17}$ and $t_{18}$, respectively. T denotes the cycle duration of ECG signal 188 (e.g., the time interval between the time points $t_0$ and $t_8$). Each point $p_0$, $p_1$, $p_2$, $p_3$, $p_4$, $p_5$, $p_6$, $p_7$, $p_8$, $p_9$, $p_{10}$, $p_{11}$, $p_{12}$, $p_{13}$, $p_{14}$, $p_{15}$, $p_{16}$, $p_{17}$ and $p_{18}$ denotes a specific position on the ECG timing signal and is associated with specific activity-state of the heart.

In this example, two-dimensional images are detected continuously at a rate of eight images per ECG cycle into predetermined points in each heart cycle. Each point $p_0$, $p_1$, $p_2$, $p_3$, $p_4$, $p_5$, $p_6$ and $p_7$ denotes a specific position on the first ECG cycle, each point $p_8$, $p_9$, $p_{10}$, $p_{11}$, $p_{12}$, $p_{13}$, $p_{14}$ and $p_{15}$ denotes a specific position on the second ECG cycle, and the like. Points $p_8$ and $p_{16}$ have the same specific position on the ECG timing signal, as point $p_0$, and hence are associated with the same activity-state. Points $p_9$ and $p_{17}$ have the same specific position on the ECG timing signal, as point $p_1$, and hence are associated with the same activity-state. Points $p_{10}$ and $p_{18}$ have the same specific position on the ECG timing signal, as point $p_2$, and hence are associated with the same activity-state. Thus, each detected two-dimensional image is associated with a specific activity-state of the heart.

Figure 5A:
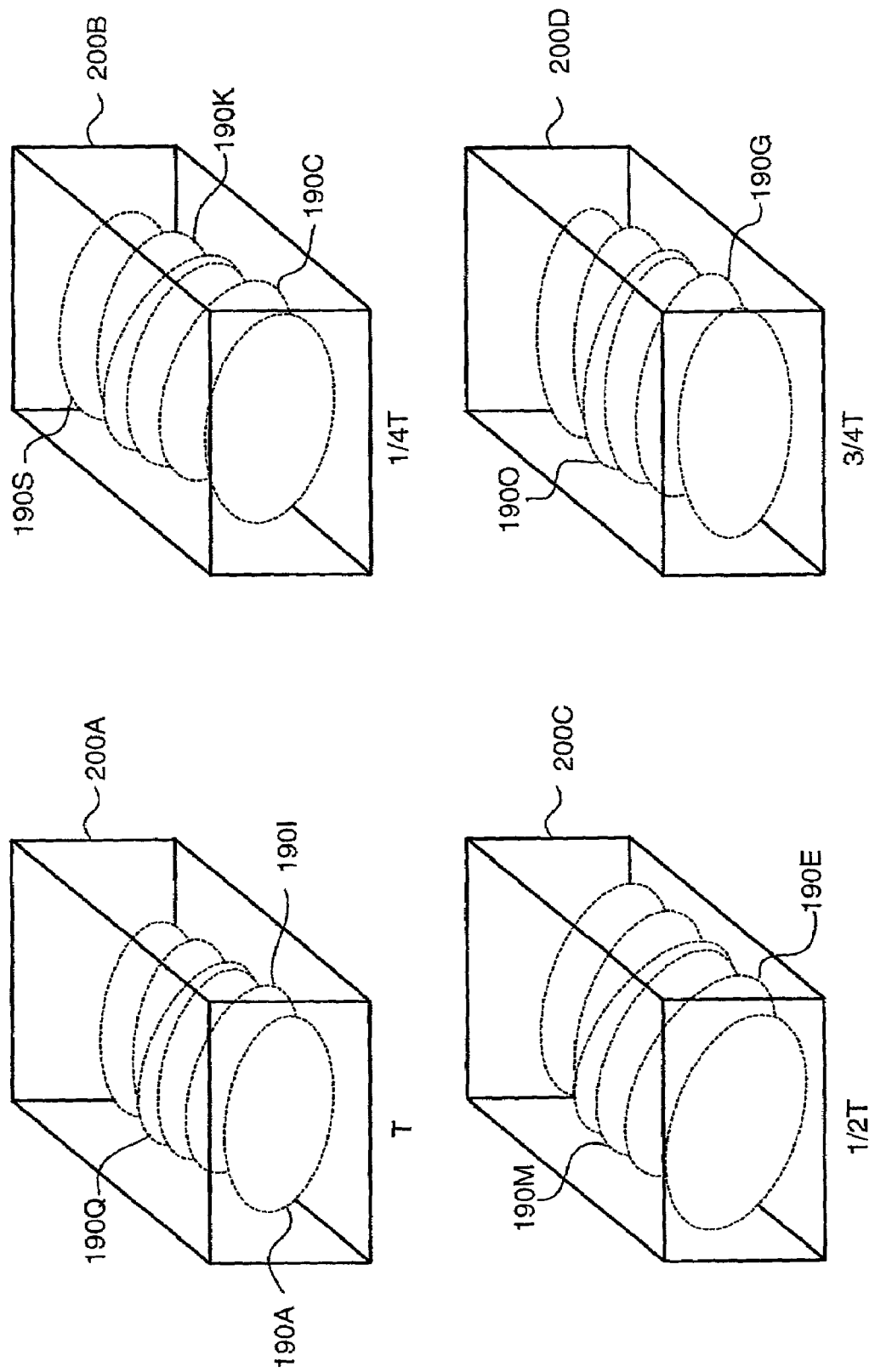
FIG. 5A is a schematic illustration of a plurality of three-dimensional volumes, according to another preferred embodiment of the present invention.
Figure 5B:
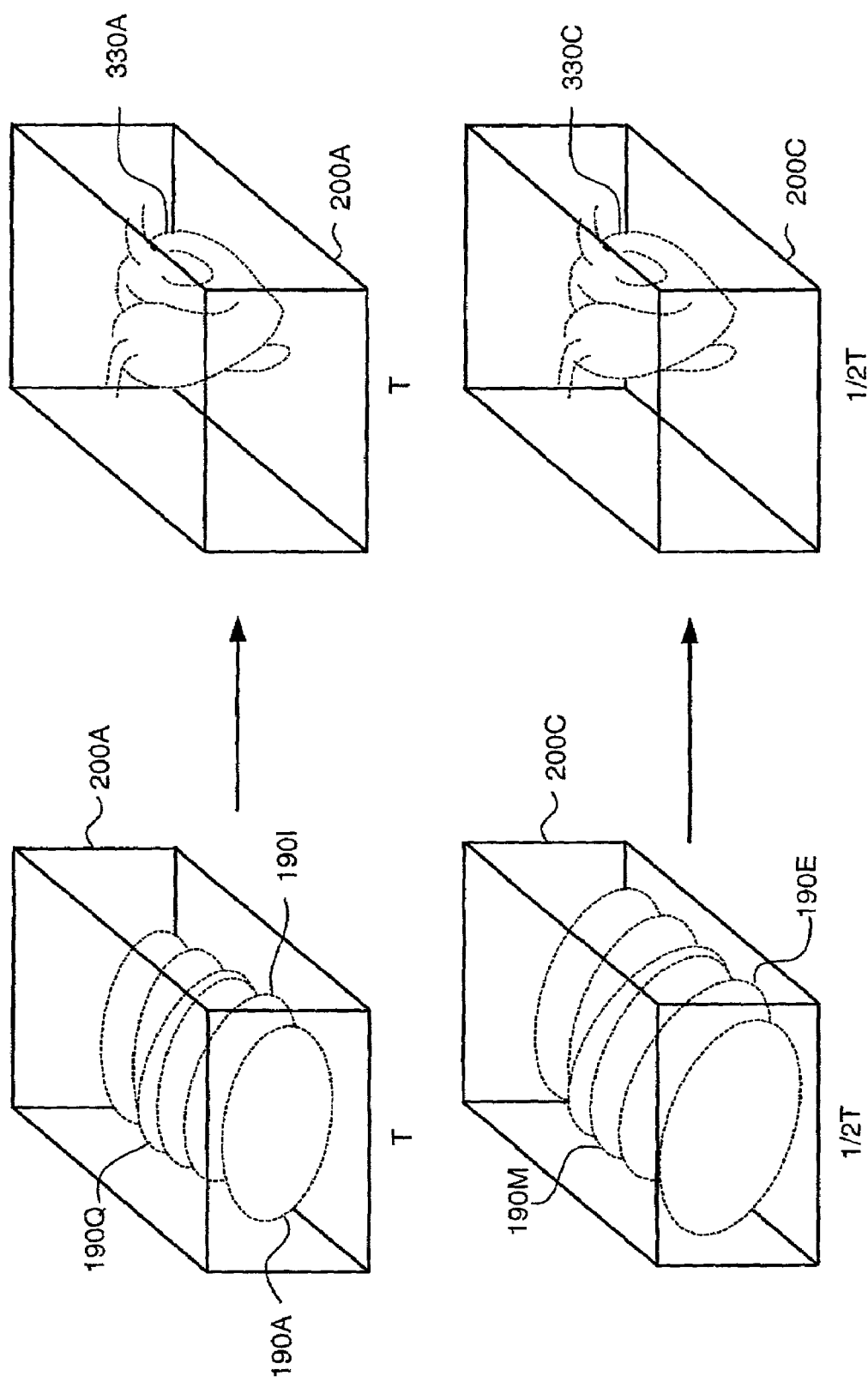
FIG. 5B is a schematic illustration of some of the three-dimensional volumes of FIG. 5A, at a later stage of image reconstruction.

Reference is now made to FIGS. 5A, 5B, 5C and 5D. FIG. 5A is a schematic illustration of a plurality of three-dimensional volumes, generally referenced 200, according to another preferred embodiment of the present invention. FIG. 5B is a schematic illustration of some of the three-dimensional volumes of FIG. 5A, at a later stage of image reconstruction. FIG. 5C is a schematic illustration of a selected three-dimensional volume of FIG. 5A, going through a procedure of image updating. FIG. 5D is a schematic illustration of a two-dimensional image, which includes foreign object information.

With reference to FIG. 5A, each of the three-dimensional volumes 200 is associated with a selected one of the specific positions in the organ timing signal cycle, and hence is associated with the respective activity-state. In the present example, three-dimensional volumes 200A, 200B, 200C and 200D are associated with organ timing signal cycle locations T, ¼T, ½T and ¾T, respectively.

Each of the three-dimensional volumes 200A, 200B, 200C and 200D is used for reconstructing a three-dimensional image for a selected location in the organ timing signal cycle, and hence for the respective activity-state. Main computer 102 (FIG. 1) sorts the two-dimensional images according to the timing position of the image on the ECG signal (i.e., a specific activity-state).

In the present example, volume 200A includes two-dimensional images 190A, 190I and 190Q (FIG. 4), which were detected at time points $t_0$, $t_8$ and $t_{16}$, respectively. The position in the organ timing signal cycle of these images is T. Volume 200B includes two-dimensional images 190C, 190K and 190S (FIG. 4), which were detected at time points $t_2$, $t_{10}$ and $t_{18}$, respectively. The position in the organ timing signal cycle of these images is ¼ T. Volume 200C includes two-dimensional images 190E and 190M (FIG. 4), which were detected at time points $t_4$ and $t_{12}$, respectively. The position in the organ timing signal cycle of these images is ½ T. Volume 200D includes two-dimensional images 190G and 190O (FIG. 4), which were detected at time points $t_6$ and $t_{14}$, respectively. The position in the organ timing signal cycle of these images is ¾ T.

At this point, volume 200A contains information relating to the two-dimensional images that were stored therein, while portions of volume 200A remain at zero value, since no two-dimensional image is related thereto. D3DR 112 analyzes the content of three-dimensional volume 200A and attempts to determine the value of some of these zero value portions, for example, by means of extrapolation. With reference to FIG. 5B, D3DR 112 (FIG. 1) reconstructs image 330A within three-dimensional volume 200A. Similarly, D3DR 112 reconstructs image 330C within three-dimensional volume 200C.

System 100 (FIG. 1) updates the three-dimensional image 330A in real time. Main computer 102 (FIG. 1) continuously receives two-dimensional images, associated with a location and orientation thereof and an organ activity-state. Main computer 102 (FIG. 1) provides each of these two-dimensional images to Db 3DR 112 (FIG. 1) together with the three-dimensional volume, associated with the same organ activity-state. D3DR 112 updates the three-dimensional volume according to the values of the new two-dimensional images.

The update procedure can be performed in many ways. According to one aspect of the invention, a new value in a selected three-dimensional pixel (voxel) replaces an old value. According to another aspect of the invention, an updated voxel value includes a combination (linear or otherwise) of the old voxel value (i.e., which already exists in the three-dimensional volume) and the newly acquired value (i.e., received from the two-dimensional image). It is noted that system 100 can operate either using polygonal or voxel representations.

According to a further aspect of the invention, each of the voxels in the three-dimensional volume includes various attributes such as if the current value thereof, was provided from an acquired image, or was calculated in the process of reconstructing the three-dimensional image, by means of extrapolation. In this case, a newly acquired value is preferred over a calculated one. With reference to FIG. 5C, D3DR 112 receives a new two-dimensional image 190Y, which is associated with an organ activity state of t=T. D3DR 112 updates the respective three-dimensional volume 200A and the image therein 330A, thereby producing an updated image $330A_{UPDATED}$.

In case where a surgical tool 120 (FIG. 1) is inserted in the inspected organ, the system 100 excludes a fragment of the two-dimensional image, which contains a representation of the surgical tool 120. Main computer 102 (FIG. 1) modifies the two-dimensional image by excluding these fragments (e.g. by introducing null values to those fragments). D3DR 112 analyzes the modified two-dimensional image and does not update the respective portions in the respective three-dimensional volume.

System 100 incorporates the ability to update the three-dimensional image sequence of the inspected object, in real time, even in the presence of foreign objects such as surgical tool 174 (FIG. 2A). According to a preferred embodiment of the invention, main computer 102 can determine according to the location and orientation of an acquired image and of surgical tool 174, if the surgical tool was included in the slice represented by the acquired image. With reference to FIG. 5D, two-dimensional image 190Z incorporates a small section 198, which is a representation of a portion of surgical tool 120, as determined from the location and orientation of MPS sensor $162_1$. Two-dimensional image 190Z and section 198 define a section 199, in which section 198 is excluded from two-dimensional image 190Z. According to real-time updating procedure of the three-dimensional image sequence which was described in connection with FIG. 5D, system 100 updates only section 199 to the respective three-dimensional image. Hence, when the surgical tool is removed from the body of the patient, it leaves no traces in the reconstructed three-dimensional images.

It is noted that each ECG cycle consists of a period of relaxation, named a diastole followed by a period of contraction named a systole. Duration of the ECG cycle is defined as a time between two subsequent heart contractions. According to a further preferred embodiment, the ECG cycle is evenly divided by N, where N denotes the number of three-dimensional images in the final image sequence.

Figure 6:
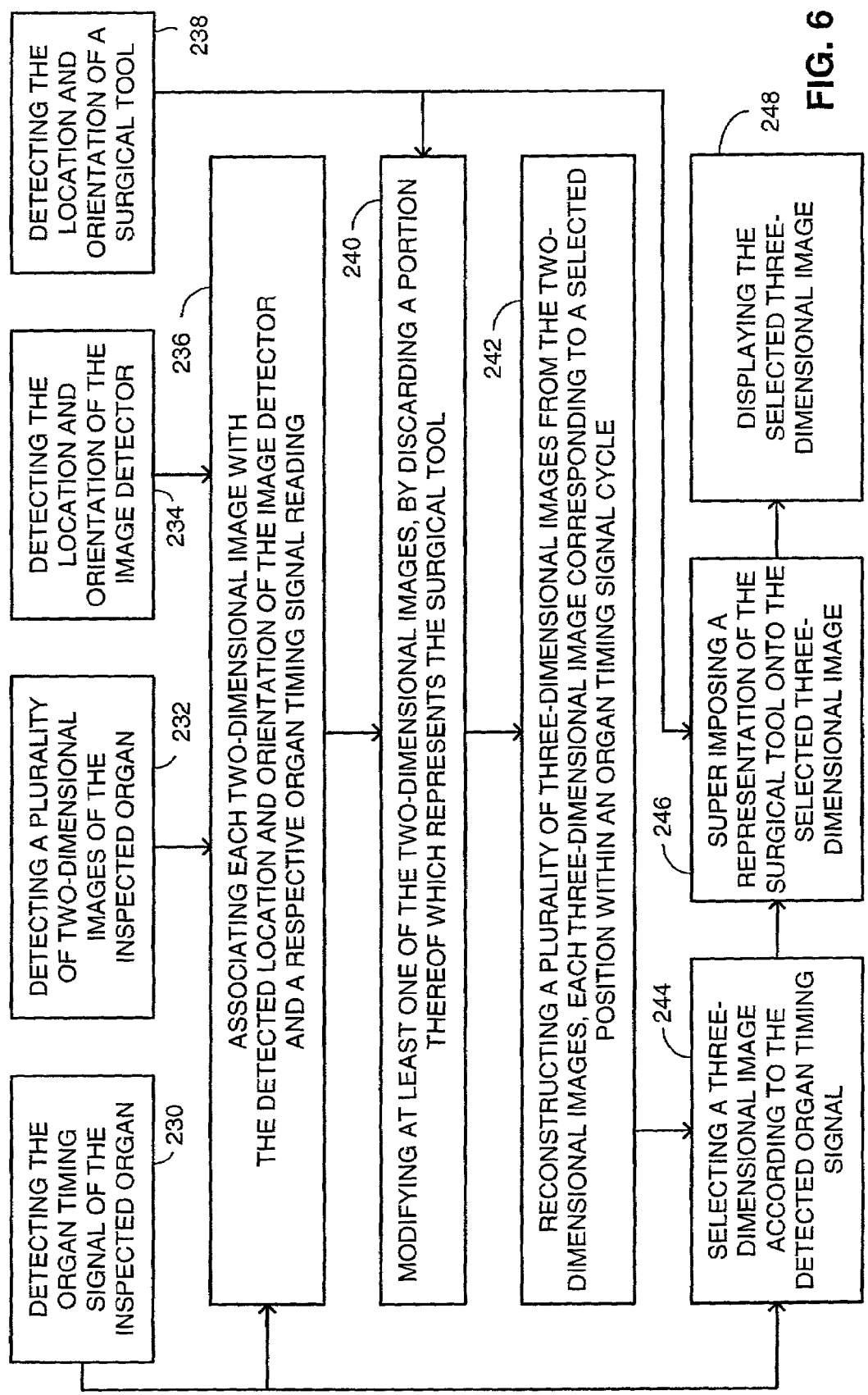
FIG. 6 is a schematic illustration of a method for operating the three-dimensional imaging system of FIG. 1, operative in accordance with a further preferred embodiment of the presented invention.

Reference is now made to FIG. 6, which is a schematic illustration of a method for operating the three-dimensional imaging system 100, operative in accordance with a further preferred embodiment of the presented invention. In procedure 230, the timing signal of an inspected organ is detected. The detection is performed by a medical monitoring device, which is selected according to the inspected organ. For example, if the inspected organs are blood vessels of the heart, then the medical monitoring device is an ECG monitor. If the inspected organs are the lungs, then the medical device is a respiratory rate monitor. Special devices can be constructed for detecting the movement of the eye lid, the eye, and the like. For example, an MPS sensor can be attached to the eye lid for detecting the movement thereof. With reference to FIG. 1, ECG monitor 106 detects the organ timing signal through ECG-electrodes 128.

In procedure 232, a plurality of two-dimensional images of the inspected organ is detected. With reference to FIG. 1, two-dimensional image acquisition device 104 detects a plurality of two-dimensional images of the inspected organ through image transducer 118.

In procedure 234, the three-dimensional location and orientation of the image detector is detected. With reference to FIG. 1, MPS system 108 detects the three-dimensional location and orientation of the image detector using MPS sensor $162_2$, mounted thereon.

In procedure 236, each detected two-dimensional image is associated with the location and orientation information thereof and the organ timing signal at the time the two-dimensional image was taken. With reference to FIG. 1, main computer 102 receives the ECG signal, the acquired two-dimensional images and the location and orientation of each two-dimensional image. Main computer 102 associates each detected image with the location and orientation information thereof and with the organ-timing signal.

In procedure 238, the location and orientation of a surgical tool are detected. With reference to FIG. 1, MPS system 108 detects the location and orientation of surgical tool 120, via MPS sensor $162_1$.

In procedure 240, the two-dimensional images are modified by discarding a portion thereof, which represents the surgical tool. It is noted that two-dimensional images which are located in planes which do not intersect the surgical tool, do not include any image respective thereof and hence remain unchanged. With reference to FIGS. 1 and 5D, main computer 102 estimates the portion within an acquired two-dimensional image, such as two-dimensional image 190Z, that might include a representation of the image of surgical tool 120. Main computer 102 performs that estimation according to the detected location and orientation of surgical tool 120. Main computer 102 determines a three-dimensional space, which is occupied by surgical tool 120, according to the information which MPS sensor $162_1$ acquires and according to data respective of the physical dimensions of surgical tool 120. Main computer 102 calculates an intersection area (e.g., portion 198 as illustrated in FIG. 5D), in which an acquired two-dimensional image (e.g., reference 190Z in FIG. 5D) and that three-dimensional space intersect. Main computer 102 discards that intersection area for example, by changing the values thereof to null values. Discarding of the image of surgical tool 120 from the two-dimensional images, is necessary in order to reconstruct a three-dimensional image of the inspected organ, free of artifacts such as the image of surgical tool 120.

In procedure 242, a three-dimensional image is reconstructed. The reconstruction includes three procedures. The first procedure is sorting the two-dimensional images into groups, according to their respective timing position (i.e., activity-state) within the organ timing signal. With reference to FIG. 1 main computer 102 sorts the two-dimensional images according to the image timing position in the organ timing signal cycle.

The second procedure is the placing of all of the two-dimensional images of a selected group in a three-dimensional virtual volume (such as a three-dimensional matrix), according to their respective location and orientation. With reference to FIG. 1, main computer 102 stores each two-dimensional image in a selected one of the three-dimensional virtual volumes 200 (FIG. 5A) within adaptive volumetric database 114.

The third procedure is filling the missing parts in the three-dimensional virtual volumes, for example, by means of interpolation. With reference to FIG. 1, D3DR 112 reconstructs a three-dimensional image in each of the three-dimensional virtual volumes 200 (FIG. 5B), from the two-dimensional images stored therein.

In procedure 244, a three-dimensional image is selected according to the organ timing signal detected in procedure 230. With reference to FIGS. 1 and 4, ECG monitor 106 detects the organ timing signal 188 of the inspected organ via ECG-electrodes 128. Main computer 102 selects three-dimensional images according to a real time detected organ timing signal. The selected three-dimensional image has to be associated with the position in the organ timing signal cycle, as the position of the real time detected organ timing signal cycle.

In procedure 246, a representation of the surgical tool is added to the selected three-dimensional image. With reference to FIG. 1, MPS sensor $162_1$ detects the location and orientation of surgical tool 120. Superimposing processor 116 adds a representation (e.g., a symbol) of surgical tool 120, to the selected three-dimensional image. Superimposing processor 116 adds the representation according to the location and orientation of surgical tool 120, which MPS sensor $162_1$ detects in procedure 238. Since the location and orientation of the surgical tool and the location and orientation of the acquired images, are all detected using the same MPS system, they all reside in a single coordinate system and hence do not have to be correlated with one another.

Figure 8:
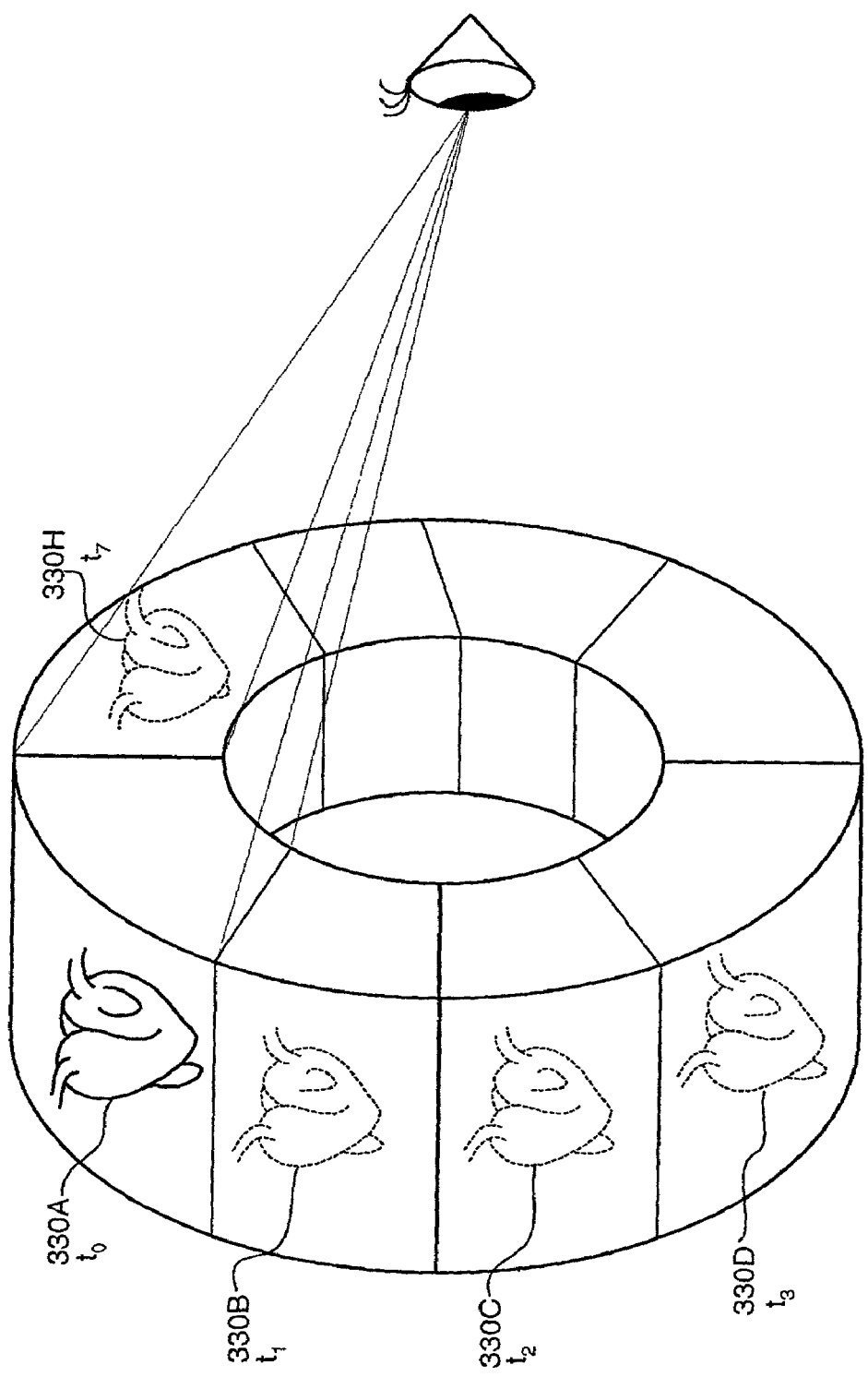
FIG. 8 is an illustration in perspective of a cyclical sequence of three-dimensional images, according to a further preferred embodiment of the present invention.

In procedure 248, the selected three-dimensional image is displayed. With reference to FIGS. 1 and 8, display 130 displays the selected three-dimensional images in a sequence, according to the real time detected organ timing signal cycle. For example, the operator can view a video of the heart of the patient, which corresponds to the real time detected heartbeat of the patient and at the same time, hear this heartbeat through a stethoscope.

Figure 7A:
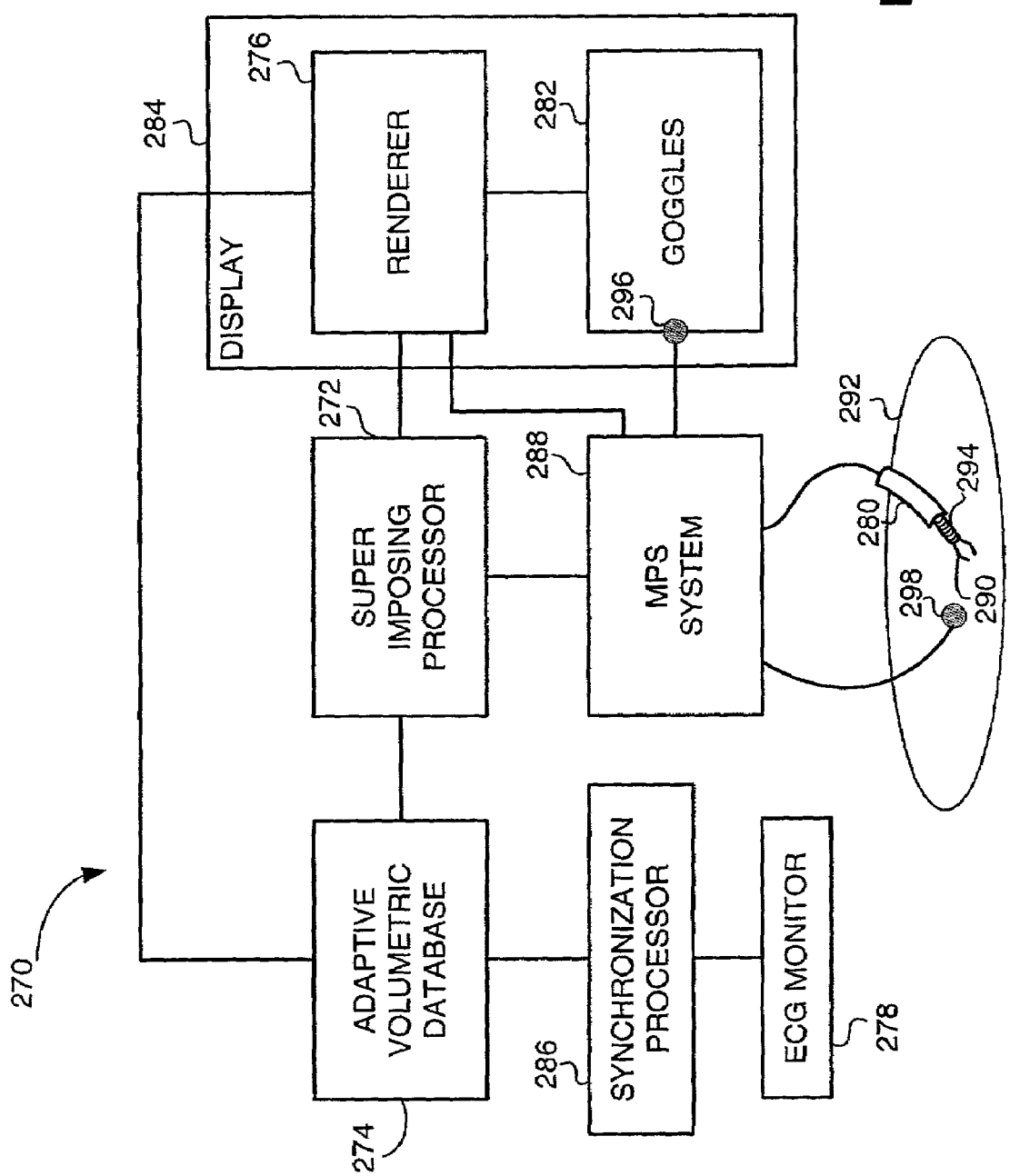
FIG. 7A is a schematic illustration of a real-time three-dimensional display playback system, constructed and operative in accordance with another preferred embodiment of the present invention.
Figure 7B:
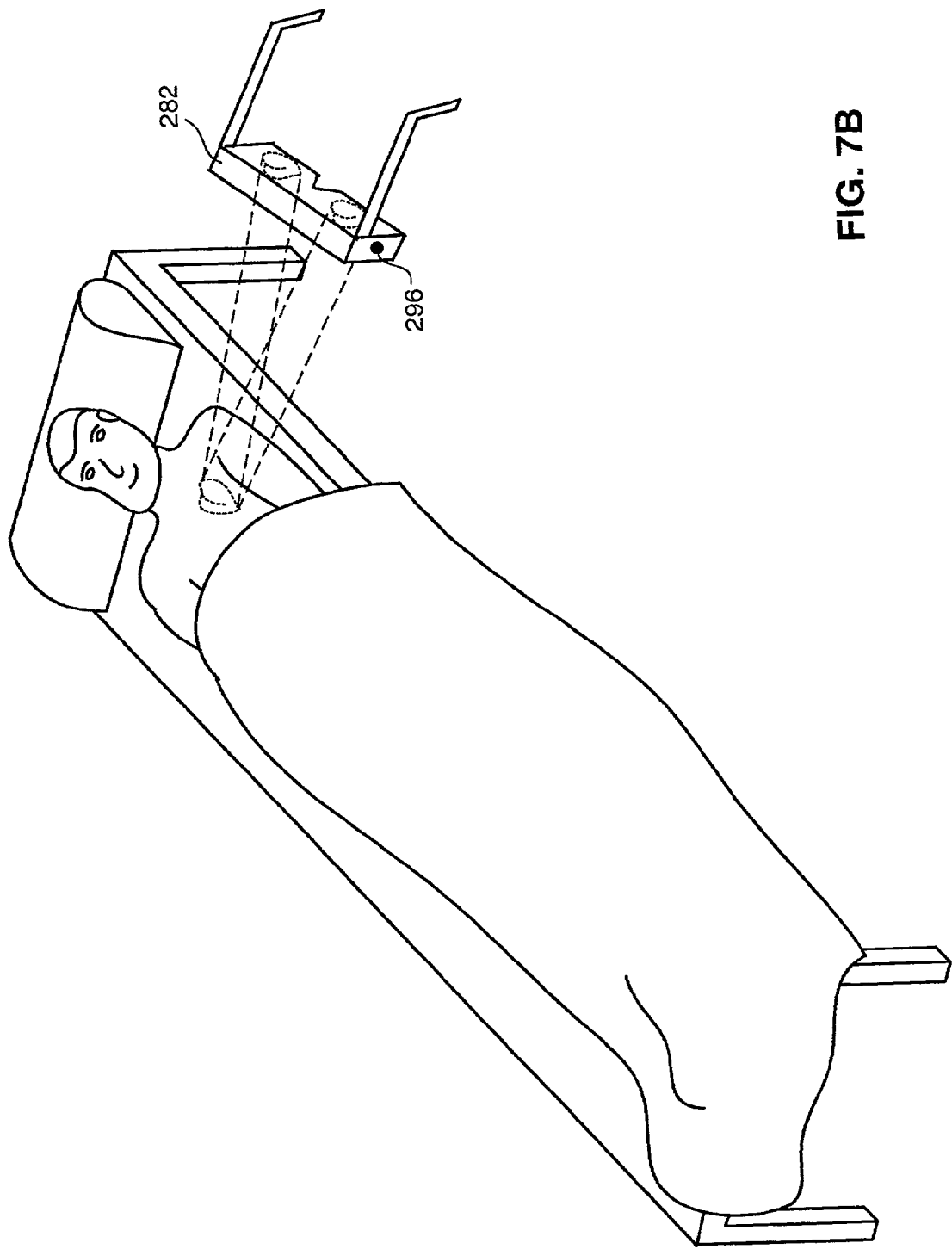
FIG. 7B is a schematic illustration of the goggles of FIG. 7A, displaying a three-dimensional image of the heart of a patient.

Reference is now made to FIGS. 7A and 7B. FIG. 7A is a schematic illustration of a real-time three-dimensional display playback system, generally referenced 270, constructed and operative in accordance with another preferred embodiment of the present invention. FIG. 7B is a schematic illustration of the goggles of FIG. 7A, displaying a three-dimensional image of the heart of a patient.

With reference to FIG. 7A, system 270 includes a superimposing processor 272, an adaptive volumetric database (AVDB) 274, an ECG monitor 278, a display 284, a synchronization processor 286, a medical positioning system (MPS) 288, a dilation catheter 280 and a plurality of MPS sensors 294, 296 and 298. Display 284 includes a renderer 276 and goggles 282. A surgical tool 290 is inserted into dilation catheter 280.

Superimposing processor 272 is coupled to AVDB 274, renderer 276 and to MPS system 288. Renderer 276 is further coupled AVDB 274 and to goggles 282. MPS system 288 is further coupled to dilation catheter 280, renderer 276 and to MPS sensors 294, 296 and 298. Synchronization processor 286 is coupled to AVDB 274 and to ECG monitor 278.

ECG monitor 278 detects the organ timing signal of the inspected organ and provides this signal to synchronization processor 286. The detected organ timing signal is used for synchronizing a sequence of the three-dimensional images with the movement of the inspected heart.

Synchronization processor 286 analyzes the ECG signal, and determines activity-states therein. Synchronization processor 286 provides a retrieval command to AVDB 274, to retrieve an image record, according to the currently detected activity-state.

AVDB 274 contains a sequence of three-dimensional images of the inspected organ, along with an activity-state associated therewith and with the location and orientation of the coordinate system thereof. It is noted that this sequence of the three-dimensional images can be acquired using system 100 (FIG. 1) or any other system for acquiring three-dimensional images (e.g., MRI, X-rays, and the like).

AVDB 274 selects a three-dimensional image of the organ, which is associated with the specific activity-state according to the received retrieval command. This three-dimensional image can be rendered and displayed as is, in synchrony with the organ timing signal. In the example, where the inspected organ is the heart, the physician is presented with an image sequence, which is real-time synchronized with the ECG signal. The physician, as she uses her stethoscope to hear the heart beats, can see a moving visual representation of the heart, at the same time.

Renderer 276 can render the three-dimensional image according to reference coordinates of surgical tool 290, reference coordinates of the inspected organ, or reference coordinates of the body of the patient. The selected reference coordinates define a stationary reference coordinate system, in which all the other objects may move.

For example, if the coordinates of surgical tool 290 are selected as reference, then renderer 276 renders the three-dimensional image so that the surgical tool is stationary and the heart moves relative thereto. Accordingly, when the physician moves surgical tool 290 relative to the inspected organ, she observes a stationary representation of surgical tool 290, while the inspected organ exhibits movement due to the motion of the inspected organ relative to the representation of surgical tool 290.

On the contrary, if the coordinates of the inspected organ are selected as reference, then renderer 276 renders the three-dimensional image so that the inspected organ is stationary and surgical tool 290 moves relative thereto. Accordingly, when the physician moves surgical tool 290 relative to the inspected organ, she observes a stationary image of the inspected organ, while surgical tool 290 exhibits movement due to the motion of the representation or surgical tool 290 relative to the inspected organ.

MPS system 288 includes an MPS transmitter (not shown) and MPS sensors 294, 296 and 298. MPS system 288 determines the location and orientation of surgical tool 290, using sensor 294 mounted thereon. MPS system 288 determines the location and orientation of the point of view of the user, using MPS sensor 296 (FIG. 7B), mounted on goggles 282. MPS system 288 determines the location and orientation of the body of the patient using MPS sensor 298, attached thereto.

Superimposing processor 272 receives the selected three-dimensional image of the heart from AVDB 274. Superimposing processor 272 further receives parameters related to the location and orientation of surgical tool 290 and parameters related to the location and orientation of reference points on the body of the patient, from MPS system 288.

Superimposing processor 272 uses the location and orientation of the reference points to align the coordinate system of the three-dimensional images with the coordinate system of surgical tool 290. Superimposing processor 272 adds a representation of surgical tool 290 to the three-dimensional image of the heart and provides this image to renderer 276.

Renderer 276 receives parameters related to the location and orientation of goggles 282 and the parameters related to the location and orientation of the reference points of the body of the patient, from MPS system 288. Renderer 276 uses these parameters to determine a viewing plane, and renders the three-dimensional images to that viewing plane. Renderer 276 provides the rendered images to goggles 282.

Goggles 282 (FIG. 7B) are preferably see-through, so that they are semi-transparent, in a way that the physician can actually see the body of the patient as well as an image projected on the goggle screens. System 270 (FIG. 7A) determines a projection plane on the body of the patient, according to the location and orientation of the body of the patient and of goggles 282. System 270 displays the three-dimensional image sequence using goggles 282 so that it is perceived to be within the body of the patient, as actually seen by the physician through goggles 282.

Reference is now made to FIG. 8, which is an illustration in perspective of a cyclical sequence of three-dimensional images, according to a further preferred embodiment of the present invention. The sequence is presented, image by image to a user, so as to produce an illusion of a moving image. The intermediate presented three-dimensional image is selected according to a real-time detected specific location in the organ timing signal cycle.

With reference to FIG. 7A, AVDB 274 selects three-dimensional images continuously, for example, at a rate of eight images per each heart cycle. Synchronization processor 286 provides a retrieval command to AVDB 274, according to the currently detected specific position in the organ timing signal cycle. AVDB 274 retrieves three-dimensional images 330A, 330B, 330C, 330D and 330H according to selected points $t_1=0$, $t_1=\frac{1}{8}T$, $t_2=\frac{2}{8}T$, $t_3=\frac{3}{8}T$, $t_4=\frac{4}{8}T$ and $t_7=\frac{7}{8}T$ within the heart timing signal (FIG. 4), respectively. As stated above, each three-dimensional image 330 is associated with the specific activity-state of the heart. Hence, playing images 330A, 330B, 330C, 330D and 330H in cyclic sequence provides a pseudo-realistic illustration of the motion of the organ (i.e., due to the repetitive nature of the periodic cardiac motion).

Figure 9:
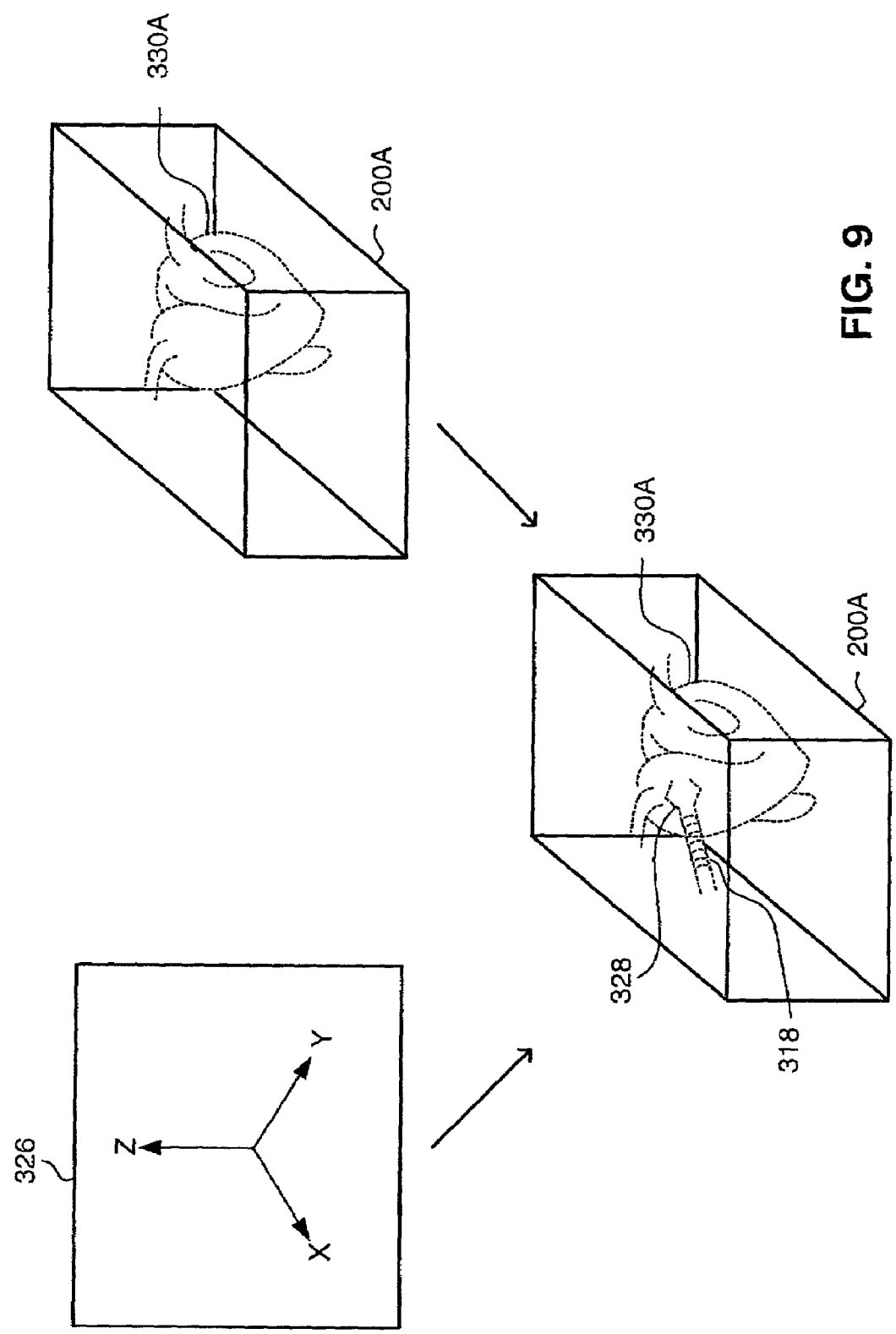
FIG. 9 is a schematic illustration of a superimposing process, operative in accordance with another preferred embodiment of the present invention.

Reference is now made to FIG. 9, which is a schematic illustration of a superimposing process, operative in accordance with another preferred embodiment of the present invention. The system 270 (FIG. 7A) introduces a representation of the currently used surgical tool 328 in each selected image, such as image 330A. This representation can either be a minimal one (e.g., in the form of a cursor) or an elaborated one which provides pseudo-realistic visualization of that surgical tool.

The location and orientation of three-dimensional image 330A are determined in a coordinate system 326 (X, Y and Z). Similarly, the location and orientation of a MPS sensor 318, and hence the location and orientation of a surgical tool 328 are also determined in the coordinate system 326 (X, Y and Z). Accordingly, a real-time representation of surgical tool 328 can be added to three-dimensional image 330A. With reference to FIG. 7A, superimposing processor 272 adds the representation of surgical tool 328 to the selected three-dimensional image 330A, which was reconstructed in thee-dimensional volume 200A. It is noted that the surgical tool is a conventional tool, such as clamp, laser cutter, brush, catheter, stent, balloon, pace maker electrode, solution dispensing unit, neuron electrode, substance collection unit, surgical delivery tool (e.g., for delivering genes, drugs, devices and the like), and the like. For example, a device delivery tool can be a medical tool for delivery of a medical device, such as a permanent stent, a removable stent, and the like, to the body of the patient.

Figure 10:
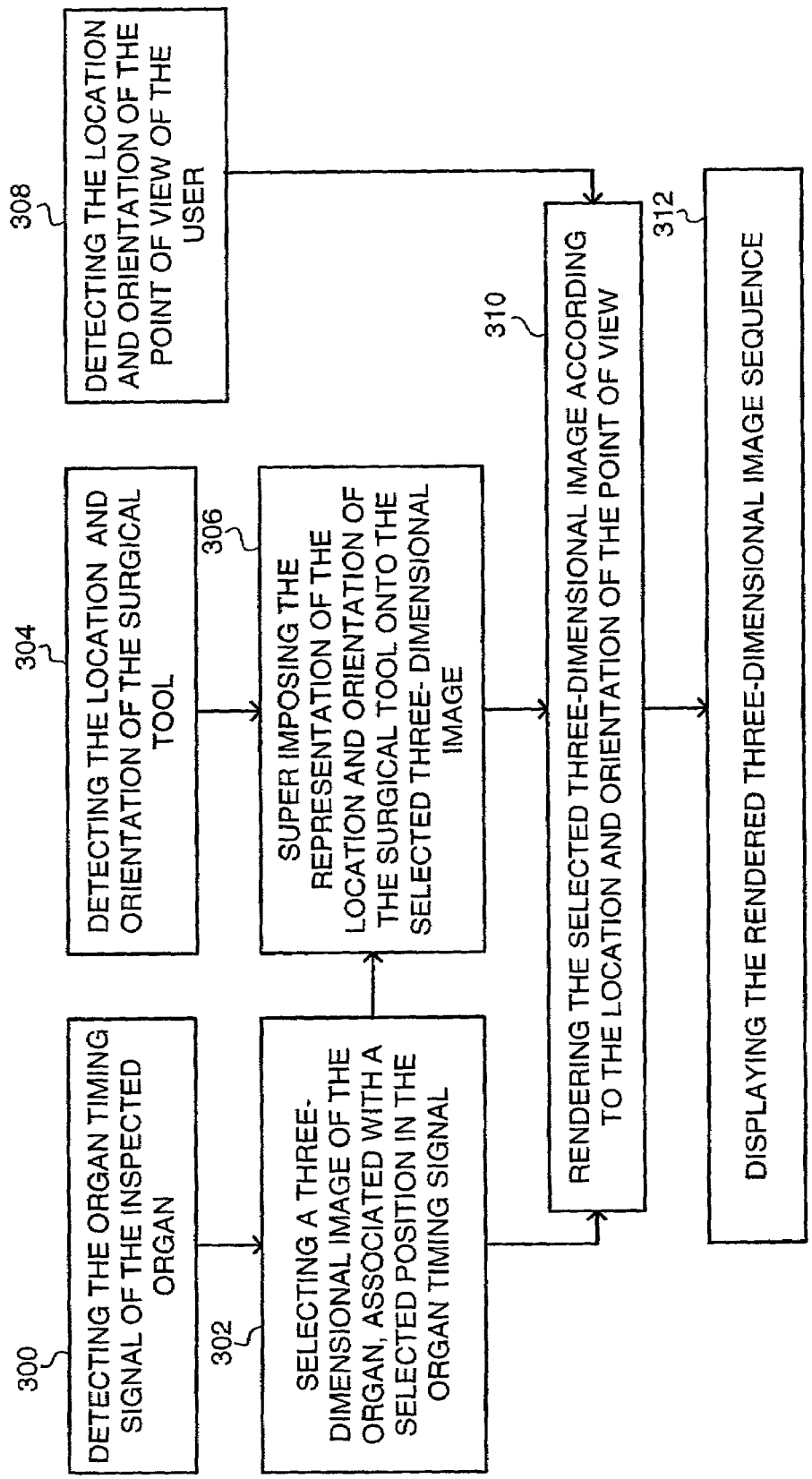
FIG. 10 is a schematic illustration of a method for operating the system of FIG. 7A, operative in accordance with a further preferred embodiment of the present invention.

The present invention allows the physician to operate on a dynamically moving object such as the heart, with a real-time representation surgical tool that she is using. Reference is now made to FIG. 10, which is a schematic illustration of a method for operating system 270, operative in accordance with a further preferred embodiment of the present invention. In procedure 300, an organ timing signal of the inspected organ is detected. According to the present invention, the system 100 (FIG. 1) includes a medical monitoring device, which is selected according to the inspected organ. Such device detects a time dependent signal of the organ, which is associated with an organ movement. With reference to FIG. 7A, ECG monitor 278 detects the heart-timing signal.

In procedure 302, a three-dimensional image of the organ (e.g., the heart), associated with a selected timing point within the organ timing signal is selected. With reference to FIG. 7A, AVDB 274 selects the three-dimensional image of the organ.

In procedure 304, the location and orientation of a surgical tool, are detected. Detection of the location and orientation of a surgical tool can be performed by methods known in the art, such as magnetic fields, ultrasound triangulation or radiation, inertial sensor—dead reckoning sensor, and the like. With reference to FIG. 7A, MPS system 288 detects the location and orientation of surgical tool 290, using sensor 294 mounted thereon.

In procedure 306, a representation of the location and orientation of the surgical tool is superimposed on the selected three-dimensional image. With reference to FIG. 7A, superimposing processor 272 superimposes parameters related to location and orientation of the surgical tool on the selected three-dimensional image.

In procedure 308, the location and orientation of the point of view of the user, are detected. The location and orientation of the point of view of the user are derived from the location and orientation of goggles 282. Parameters of the location and orientation of goggles 282 determine a viewing plane of the user. System 270 can determine two adjacent viewing planes, one for each LCD element of the goggles (one for each eye). With reference to FIG. 7A, MPS system 288 detects the location and orientation of goggles 282, using sensor 296 mounted thereon. It is noted that more than one display unit (i.e., more than one goggles unit) can be introduced to the system, employing a different MPS sensor, mounted thereon.

In procedure 310, the selected three-dimensional image is rendered according to the location and orientation of the point of view of the user. With reference to FIG. 7A, renderer 276 renders the selected three-dimensional image according to the location and orientation of the point of view.

In procedure 312, a rendered three-dimensional image sequence (i.e., a three-dimensional motion picture) is displayed. The three-dimensional motion picture of the inspected organ can be displayed on any type of display, monoscopic, stereoscopic or holographic (e.g., a video monitor, goggles, holographic generator, and the like). With reference to FIG. 7A, goggles 282 display a rendered three-dimensional image sequence.

Figure 11:
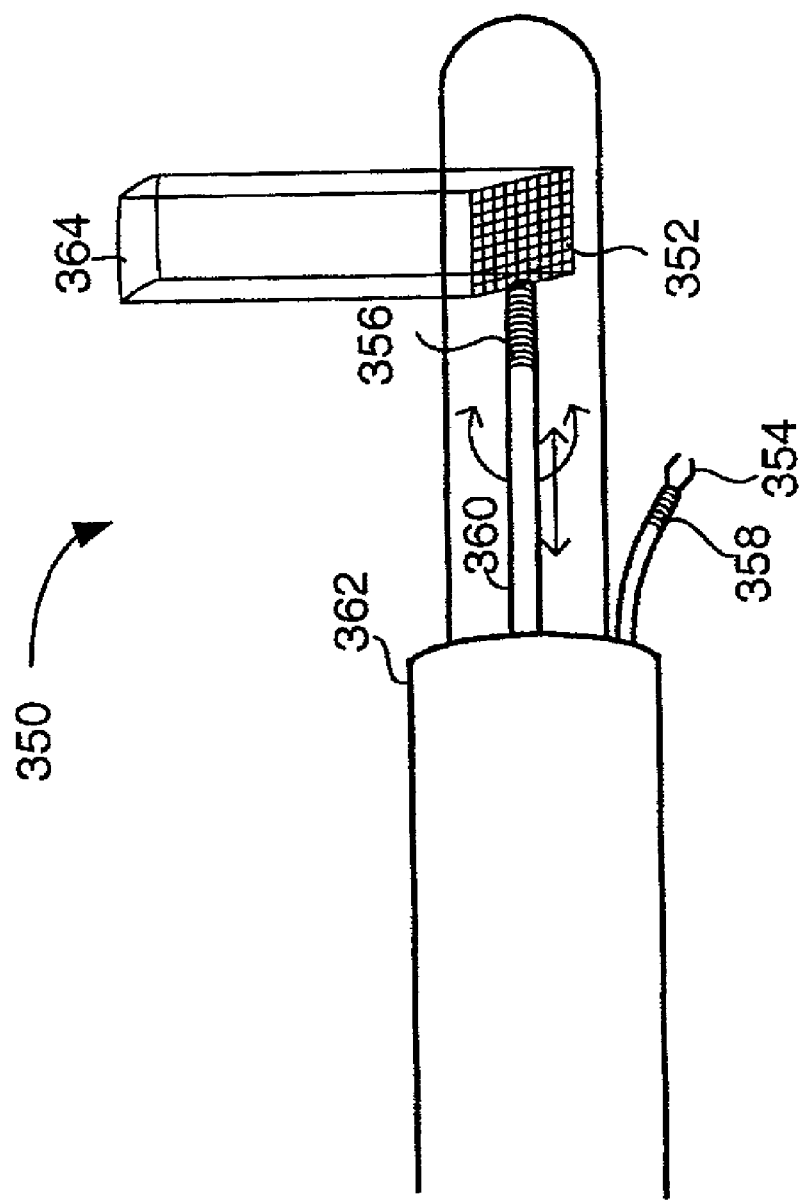
FIG. 11 is an illustration in perspective of an innervascular imaging and surgery system, constructed and operative in accordance with another preferred embodiment of the invention.

Reference is now made to FIG. 11, which is an illustration in perspective of an inner-vascular imaging and surgery system, generally referenced 350, constructed and operative in accordance with another preferred embodiment of the invention. Inner-vascular imaging and surgery system 350 includes an inner-vascular ultrasound system (IVUS) transducer 352, a surgical tool (i.e., typically a minimal invasive surgical device) 354, MPS sensors 356 and 358, a mounting catheter 360 and a dilation catheter 362. IVUS transducer 352 is mounted on mounting catheter 360. It is noted that other IVUS devices, such as ones, which include rotary acoustic mirrors, are also applicable to this embodiment.

IVUS transducer 352 produces ultrasound waves and directs them at the inner wall of a tubular organ (not shown), covering a surface referenced 364. Surface 364 reflects a portion of the ultrasonic waves directed thereto. IVUS transducer 352 detects these reflected ultrasonic waves and provides a respective signal to an image processing system (not shown) coupled thereto. A conventional image processing system reconstructs a single three-dimensional image from all of the two-dimensional images, according to the location and orientation of each of them. According to the present invention, the image processing system reconstructs a plurality of three-dimensional images, each for a different position in the timing cycle of the organ timing signal.

It is noted, that the IVUS is used for imaging the interior of coronary arteries during diagnosis, clinical treatment and performing research. This system provides a comprehensive and detailed understanding of the coronary arteries (or other blood vessels). A conventional IVUS detector is, for example, the Ultra-Cross system, manufactured by Boston Scientific Scimed or the In-Vision system, manufactured by Jomed USA (aka Endosonics) both companies located in San-Diego, Calif. USA. These systems are mainly used for slicing images of coronary images.

The present invention provides a novel structure, for producing a quantitative model of the blood vessel, using a combination of conventional IVUS elements and the unique miniature MPS sensor. Such combination shall be referred to as Guided IVUS or GIVUS, in the description to follow. According to a further preferred embodiment of the invention, the GIVUS image sequence can be visually stabilized using the ECG signal. A selected time point in the ECG signal cycle, determines the momentary local blood pressure in the blood vessel, which in turn determines the momentary diameter of that blood vessel for that position within the cycle. Hence, the visual diameter of the blood vessel can be adjusted artificially, by means of image processing, so as to display a steady image of the blood vessel during the surgical procedure.

In general, the new GIVUS system produces a "3D road map" in which the surgeon navigates. Other imaging methods can also be used for producing such a road map, which can be stored in the volumetric database and played back according to the method of the invention, such as 3D ANGIO, real time MRI, and the like.

Figure 12:
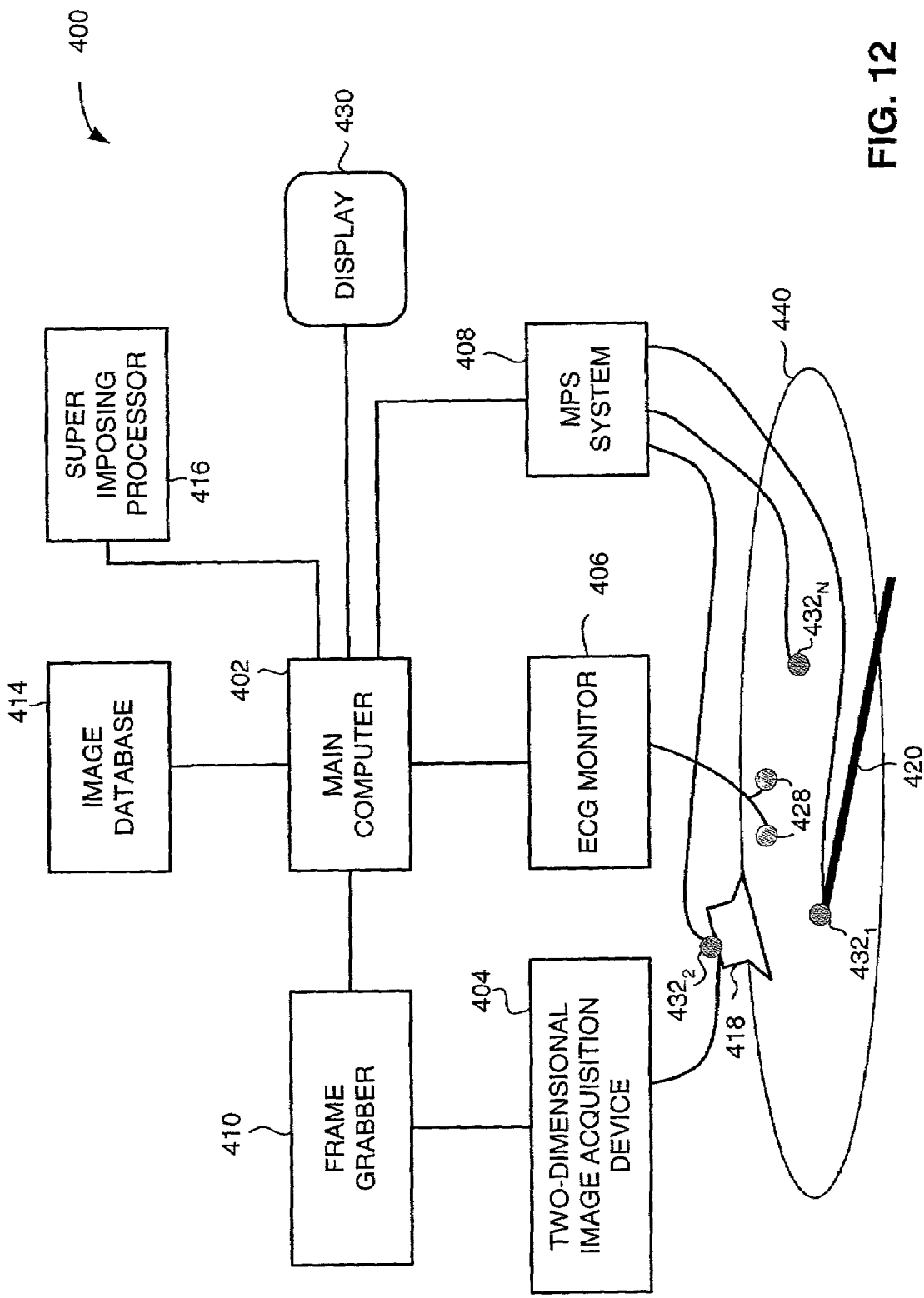
FIG. 12 is a schematic illustration of a multi function two-dimensional imaging system, constructed and operative in accordance with a further preferred embodiment of the present invention.

Reference is now made to FIG. 12, which is a schematic illustration of a multi functional two-dimensional imaging system, generally referenced 400, constructed and operative in accordance with a further preferred embodiment of the present invention. In the example set forth in FIG. 12, system 400 is adapted for producing a two-dimensional image sequence of the heart and playing it in real time in synchrony with the motion of the heart.

Two-dimensional imaging system 400 includes a main computer 402, a two-dimensional image acquisition device 404, an ECG monitor 406, a medical positioning system (MPS) 408, a frame grabber 410, an image database 414, a superimposing processor 416, a surgical tool 420, a plurality of MPS sensors $432_1$, $432_2$ and $432_N$, and a display 430.

Two-dimensional image acquisition device 404 includes an image transducer 418. ECG monitor 406 continuously detects an electrical timing signal of the heart during inspection or surgery, by employing a plurality of ECG electrodes 428.

Main computer 402 is coupled to ECG monitor 406, MPS system 408, frame grabber 410, superimposing processor 416 and to display 430. Two-dimensional image acquisition device 404 is coupled to frame grabber 410. MPS system 408 includes an MPS transmitter (not shown) and MPS sensors $432_1$, $432_2$ and $432_N$.

System 400 is directed at capturing and playing a two-dimensional image sequence of the inspected organ, with a superimposed representation of the projection of the surgical tool 420. Transducer 418 detects a plurality of two-dimensional images of the inspected organ and provides them to two-dimensional image acquisition device 404, which further transfers them to frame grabber 410. Frame grabber 410 grabs each detected two-dimensional image and provides it to main computer 402, which stores them in image database 414, along with an organ timing signal, as received from ECG monitor 406. The images can be used at any time to produce a two-dimensional cyclic image sequence of a selected plane of the inspected organ. System 400 can synchronize this image sequence with a real-time reading of the timing signal of the inspected organ, using procedures similar to those described above.

The example set forth in FIG. 12 includes MPS sensor $432_2$, which detects the location and orientation of transducer 418 for each of the acquired images and MPS system 408, which determines if all of the acquired images reside on the same plane. If not, then MPS system 408 can indicate to the user a detected deviation from a given plane, either visually, audibly or mechanically (e.g., by means of vibration, and the like). It is noted that a simpler version of system 400, according to a further preferred embodiment, does not include an MPS sensor attached to the transducer.

MPS sensor $432_1$ detects the location and orientation of surgical tool 420. MPS system 408 determines the location and orientation of surgical tool 420 and provides this information to main computer 402, which in turn provides it to super-imposing processor 416. Superimposing processor 416 determines a representation in space, of the surgical tool 420, derives a projection thereof, onto the plane of the detected images and superimposes that projection on each of the images in real time. Display 430 displays the superimposed image sequence to the user.

Superimposing processor 416 can add additional information to the super-imposed sequence, such as the location of the surgical tool, above or under the viewed plane. For example, portions of the surgical tool which are located on one side of the viewed plane shall be indicated using red color, portions of the surgical tool which are located on the other side of the viewed plane shall be indicated using blue color, and portions of the surgical tool which are located on viewed plane shall be indicated using red color. It is noted that although two-dimensional system 400 provides less visual information than system 100 of FIG. 1, it requires significantly less processing power and storage area and hence can be manufactured at considerably lower costs.

Figure 13A:
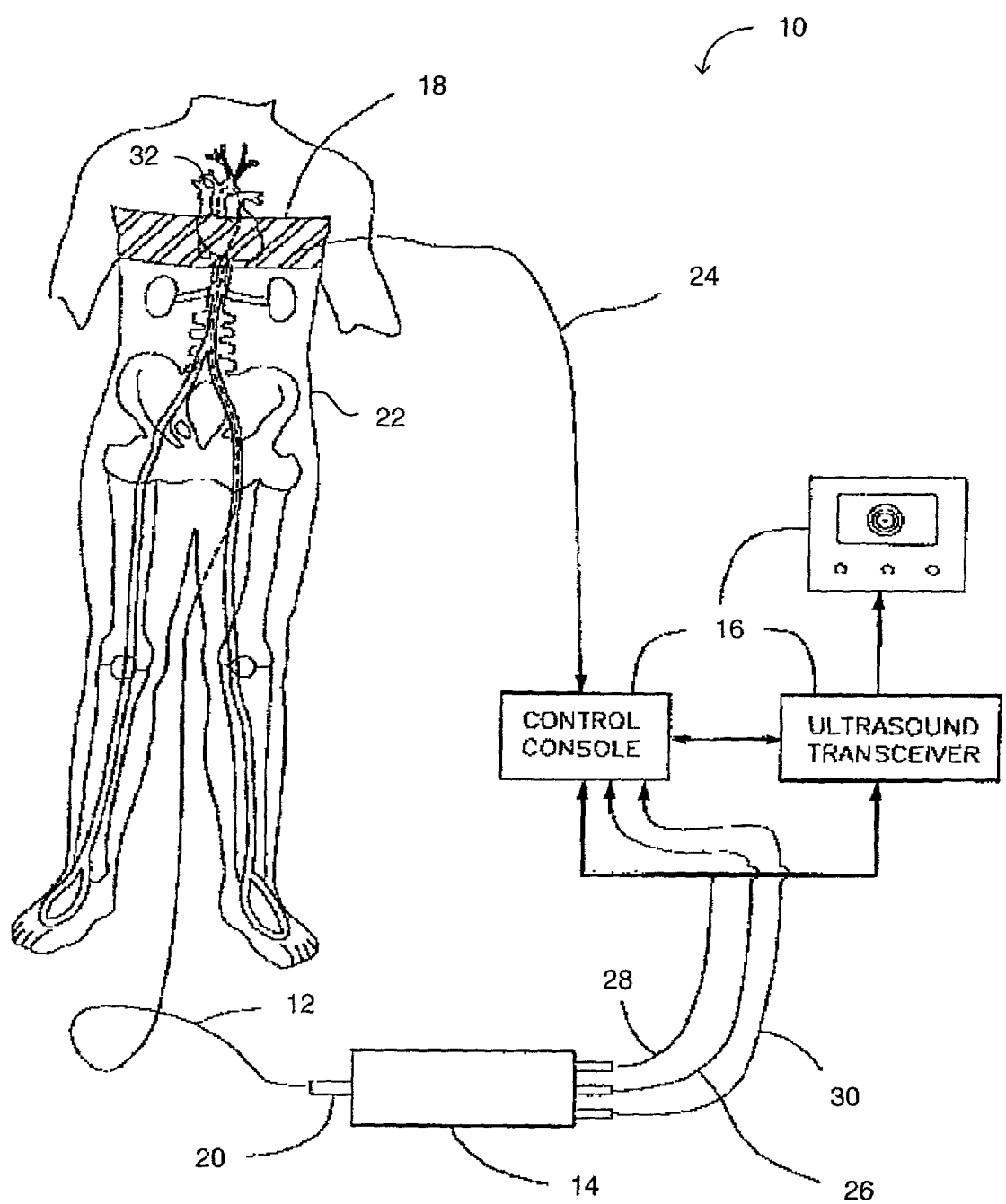
FIG. 13A is a schematic illustration of a system for displaying a three-dimensional image of an organ, which is known in the prior art.
Figure 13B:
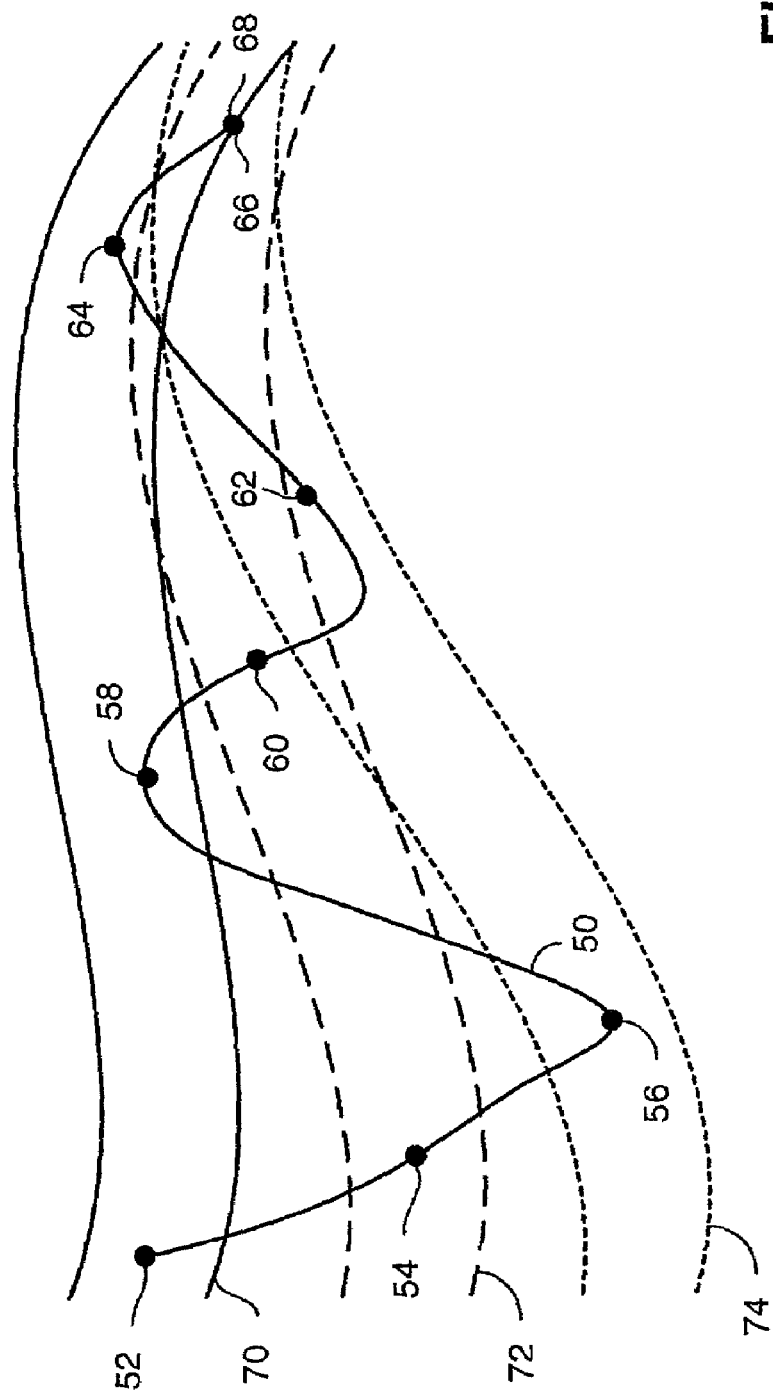
FIG. 13B is a schematic illustration of the trajectory of the imaging tip of the catheter of the system of FIG. 13A, inside an artery of the patient.
Figure 14:
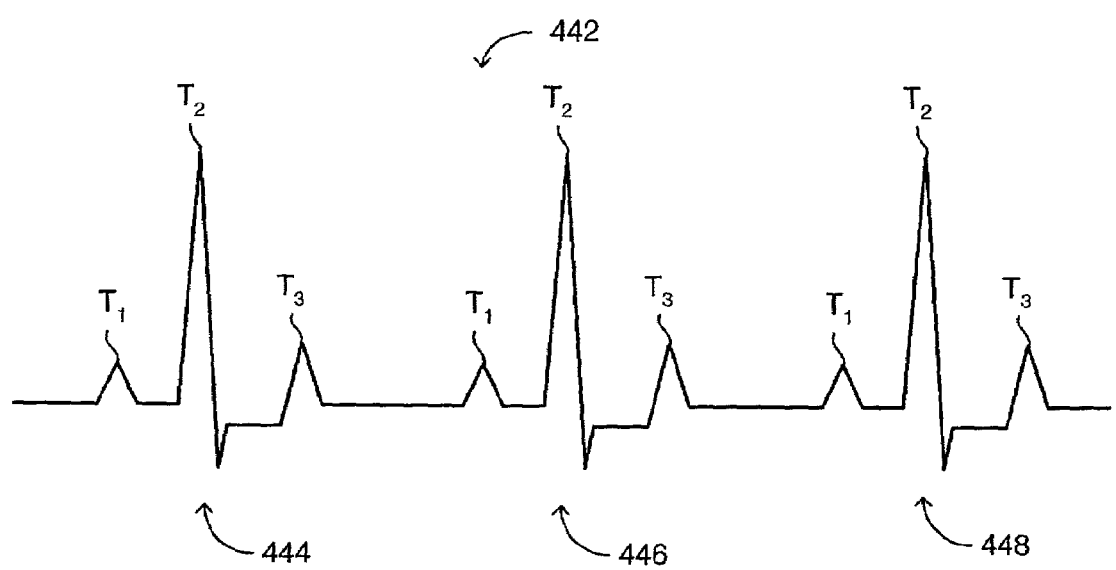
FIG. 14 is a schematic illustration of an ECG of a patient.

Reference is now made to FIG. 14, which is a schematic illustration of an ECG of a patient, generally referenced 442. ECG 442 includes a plurality of activity-states (e.g. ECG cycle phases), such as activity-states $T_1$, $T_2$ and $T_3$ in each of a plurality of heart cycles 444, 446 and 448. Applicant has found that the changes in positions of the artery, such as positions 70 (FIG. 13B), 72 and 74, are due to the heart beat of the patient and that this is the reason for inaccuracy of trajectory 50. Thus, the location and orientation of the artery is different at different activity-states, during each of the heart cycles 444, 446 and 448.

For example, at activity-state $T_1$ of each of the heart cycles 444, 446 and 448, the location and orientation of the artery is represented by an artery image at position 70 (FIG. 13B). At activity-state $T_2$ of each of the heart cycles 444, 446 and 448, the location and orientation of the artery is represented by an artery image at position 72. At activity-state $T_3$ of each of the heart cycles 444, 446 and 448, the location and orientation of the artery is represented by an artery image at position 74. Thus, each of the points 52, 54, 56, 58, 60, 62, 64, 66 and 68 corresponds to a location and orientation of the imaging tip of catheter 12 (FIG. 13A), while the artery is at a different location and orientation, in a different activity-state of a heart cycle.

For example, point 52 corresponds to activity-state $T_1$ in heart cycle 444, meaning that when the imaging tip of catheter 12 is at point 52, the heart 32 of patient 22 is at activity-state $T_1$. Point 54 corresponds to activity-state $T_2$ in heart cycle 444, meaning that when the imaging tip of catheter 12 is at point 54, the heart 32 of patient 22 is at activity-state $T_2$. Point 56 corresponds to activity-state $T_3$ in heart cycle 444, meaning that when the imaging tip of catheter 12 is at point 56, the heart 32 of patient 22 is at activity-state $T_3$. Point 58 corresponds to activity-state $T_1$ in heart cycle 446. Point 60 corresponds to activity-state $T_2$ in heart cycle 446. Point 62 corresponds to activity-state $T_3$ in heart cycle 446. Point 64 corresponds to activity-state $T_1$ in heart cycle 448. Point 66 corresponds to activity-state $T_2$ in heart cycle 448. Point 68 corresponds to activity-state $T_3$ in heart cycle 448.

According to another aspect of the present invention, location and orientation measurements, as well as images acquired, are processed with respect to the activity-state of the inspected organ, at the time of acquisition or measurement. For example, in a system according to this aspect of the invention, the imaging system displays the trajectory of an imaging catheter superimposed on a three-dimensional image of an inspected organ, wherein the three-dimensional image corresponds to an activity-state determined by the current location and orientation of the imaging catheter inside the inspected organ. The system records the path which the imaging catheter follows inside the inspected organ, in either a forward or a backward direction. The system, further registers this path with monitored activity-states of the inspected organ and with the instantaneous location and orientation of the imaging catheter.

Figure 15A:
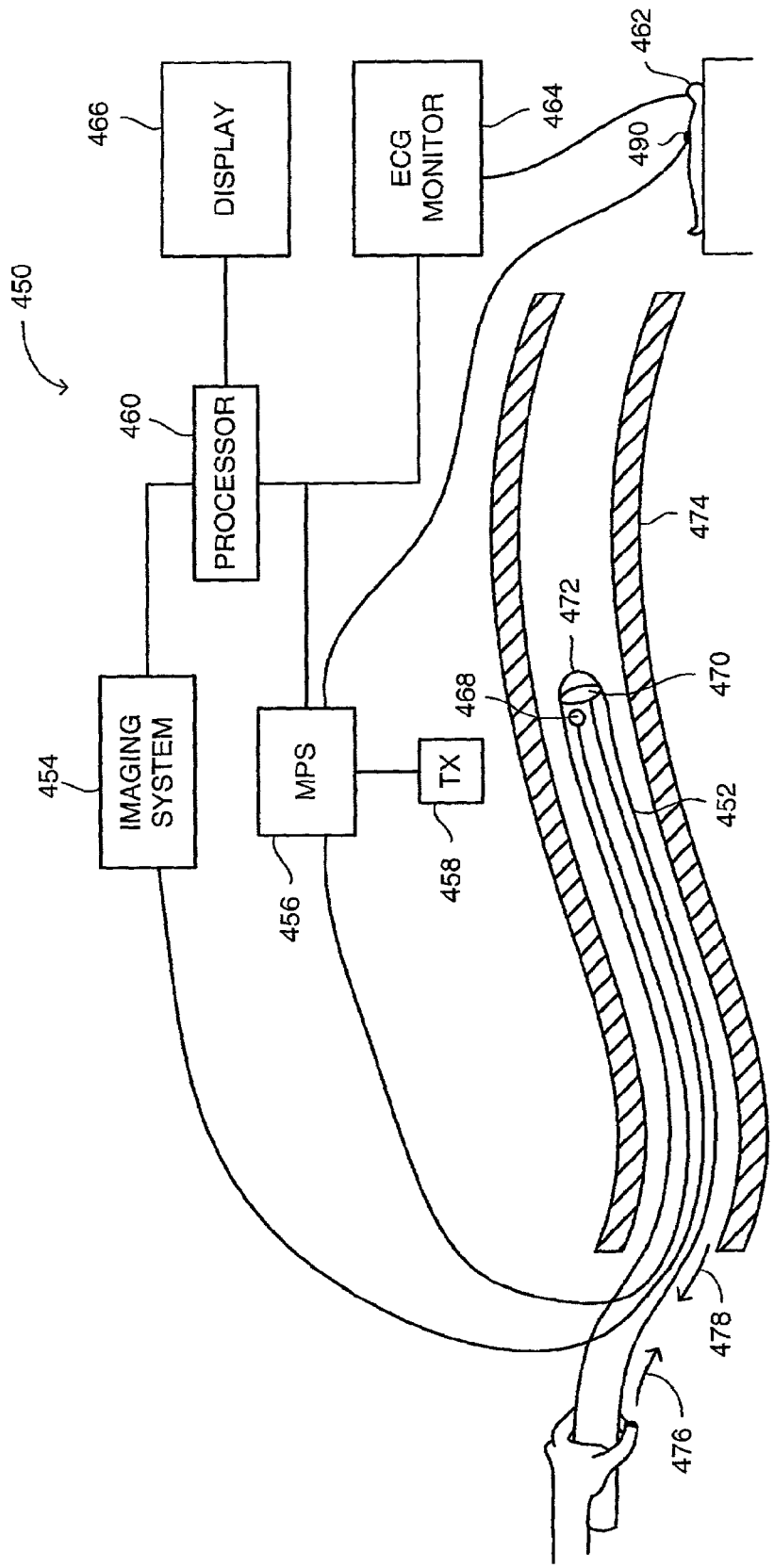
FIG. 15A is a schematic illustration of a system, constructed and operative in accordance with another preferred embodiment of the present invention.
Figure 15B:
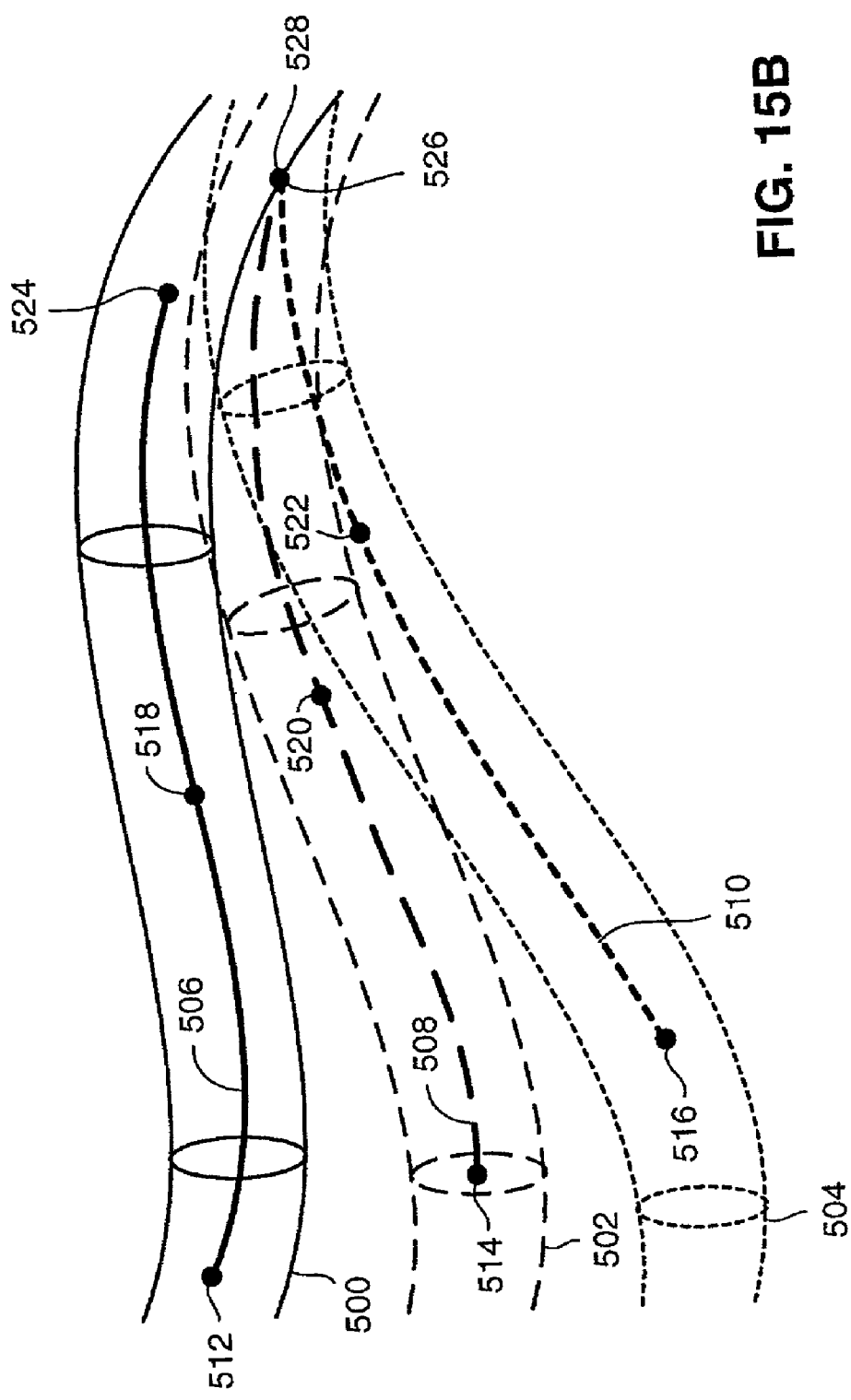
FIG. 15B is a schematic illustration of trajectories of the tip of the imaging catheter of the system of FIG. 15A, respective of different activity-states of the ECG of FIG. 14.

Reference is now made to FIGS. 15A and 15B. FIG. 15A is a schematic illustration of a system, generally referenced 450, constructed and operative in accordance with another preferred embodiment of the present invention. FIG. 15B is a schematic illustration of trajectories of the tip of the imaging catheter of the system of FIG. 15A, respective of different activity-states of the ECG of FIG. 14.

With reference to FIG. 15A, system 450 includes an imaging catheter 452, an imaging system 454, an MPS 456, a transmitter 458, a body MPS sensor 490, a processor 460, a plurality of ECG electrodes (not shown), an ECG monitor 464 and a display 466. Imaging catheter 452 includes an imaging MPS sensor 468 and an image detector 470, both located at a tip 472 of imaging catheter 452.

In the example set forth in FIG. 15A, image detector 470 is an optical coherence tomography (OCT) imaging element. It is noted that image detector 470 can be replaced with an IVUS transducer as described herein above or other types of ultrasound transducers, a magnetic resonance imaging (MRI) element, a thermography device, and the like.

Imaging system 454 produces a signal respective of the images which image detector 470 detects. MPS 456, processor 460, ECG monitor 464 and display 466 are similar to MPS 108 (FIG. 1), main computer 102, ECG monitor 106 and display 130, respectively. Display 466 can be a two-dimensional display, an auto-stereoscopic display to be viewed with a suitable pair of spectacles, a pair of goggles, and the like. Location and orientation processor of MPS 456 defines the origin of a global coordinate system. ECG monitor 464 can be replaced by a dedicated organ monitor to monitor the organ timing signals of an organ other than the heart, such as intestines, eyelid, eye, brain, liver, lungs, kidneys, and the like. Imaging MPS sensor 468 determines the location and orientation of tip 472 of imaging catheter 452 and hence, of image detector 470.

Imaging catheter 452 is located within an inspected organ 474, which in the present example is an artery. It is noted that the inspected organ can be an organ other than the artery, such as an esophagus, a vein, a bronchus, a ureter, and the like.

The ECG electrodes are attached to the body of a patient 462 and to ECG monitor 464. Body MPS sensor 490 is attached to the body of patient 462 and to MPS 456. Processor 460 is coupled to imaging system 454, MPS 456, ECG monitor 464 and to display 466. MPS 456 is further coupled to imaging MPS sensor 468 and to transmitter 458. Imaging system 454 is further coupled to image detector 470.

For each of the MPS sensors, MPS 456 determines the coordinates of the MPS sensor, relative to the origin of the global coordinate system. The determined coordinates include three rectilinear parameters and three angular parameters. MPS 456 provides MPS coordinate data respective of the determined coordinates, to processor 460.

Using body MPS sensor 490, MPS 456 determines location and orientation of patient 462, which serves as reference in case the patient moves during the operation. The operator (not shown) can manually insert or withdraw imaging catheter 452 into or out of inspected organ 474, in directions designated by arrows 476 and 478, respectively.

Following is a description of a scanning process according to one embodiment of the present invention. This embodiment overcomes the disadvantages of the prior art by processing imaging data and location and orientation data, with respect to organ activity.

The operator inserts imaging catheter 452 into inspected organ 474 and moves imaging catheter 452 within inspected organ 474, in directions 476 and 478. Image detector 470 detects a plurality of two-dimensional images of the region of inspected organ 474, which surrounds tip 472 of imaging catheter 452 and provides a respective image signal to imaging system 454. Imaging system 454 analyzes the received image signal, produces a digital representation of the two-dimensional images and provides them as image data to processor 460.

Using signals received from imaging MPS sensor 468, MPS 456 determines the location and orientation of tip 472 of imaging catheter 452, and hence, the location and orientation of each of the detected two-dimensional images, during movement of imaging catheter 452 within inspected organ 474. It is noted that the measurements of imaging MPS sensor 468 are indifferent to the movement directions 476 and 478 of imaging catheter 452.

The ECG electrodes detect the ECG of patient 462 and provide an ECG signal respective of the detected ECG, to ECG monitor 464. ECG monitor 464 generates ECG data by analyzing the received ECG signal and provides the ECG data to processor 460.

Processor 460 processes the two-dimensional images, their respective location and orientation data and their respective ECG timing, and associates each two-dimensional image, with the respective location and orientation data and with the respective ECG timing. Processor 460 sorts the two-dimensional images and their respective location and orientation data, according to their respective ECG timing, reconstructs three-dimensional images from two-dimensional images respective of selected activity states, calculates catheter trajectories from location and orientation data respective of selected activity-states, and the like. Processor 460, then stores these two-dimensional images in a database, such as adaptive volumetric database 114 (FIG. 1).

For example, with reference to FIG. 14, processor 460 associates between all of the two-dimensional images (i.e., images acquired at points 512, 518 and 524) which were detected during activity-state $T_1$ at any cycle of ECG signal 442. Similarly, processor 460 associates between all of the two-dimensional images (i.e., images acquired at points 514, 520 and 526) which were detected during activity-state $T_2$ at any cycle of ECG 442 and further associates between all of the two-dimensional images (i.e., images acquired at points 516, 522 and 528) which were detected during activity-state $T_3$ at any cycle of ECG 442.

Processor 460 reconstructs a three-dimensional image from all of the two-dimensional images, which were associated with respect to a given activity-state $T_1$. With reference to FIG. 15B, processor 460 reconstructs a three-dimensional image 500, which is the image of inspected organ 474 at activity-state $T_1$ (FIG. 14), and a three-dimensional image 502, which is the image of inspected organ 474 at activity-state $T_2$. Likewise, processor 460 reconstructs a three-dimensional image 504, which is the image of inspected organ 474 at activity-state $T_3$.

Processor 460 calculates a trajectory 506 from points 512, 518 and 524, associated with activity state $T_1$. Similarly, processor 460 calculates a trajectory 508 from points 514, 520 and 526 associated with activity state $T_2$ and further calculates a trajectory 510 from points 516, 522 and 528 associated with activity state $T_3$.

Processor 460 associates between each of the calculated trajectories and one of the reconstructed three-dimensional images, respective of a given organ activity-state. With reference to FIG. 15B, processor 460 associates between trajectory 512 and reconstructed three-dimensional image 500, respective of activity state $T_1$. Similarly, processor 460 associates between trajectory 514 and reconstructed three-dimensional image 502, respective of activity state $T_2$ and further between trajectory 514 and reconstructed three-dimensional image 504, respective of activity state $T_3$.

Since points 512, 514, 516, 518, 520, 522, 524, 526 and 528, used for calculating the trajectories are also the points at which their respective two-dimensional images were acquired, processor 460 can superimpose each of the calculated trajectories on its respective reconstructed three-dimensional image. For example, processor 460 superimposes trajectory 506 on three-dimensional image 500, trajectory 508 on three-dimensional image 502 and trajectory 510 on three-dimensional image 504.

It is noted that points 512, 514, 516, 518, 520, 522, 524, 526 and 528 represent a situation similar to that presented by points 52, 54, 56, 58, 60, 62 64, 66 and 68 (FIG. 13B). However, according to the present invention, processor 460 reconstructs each three-dimensional image, and calculates each of the trajectories, with respect to those coordinates of the tip of the imaging catheter, which belong to the same activity-state as that of the reconstructed three-dimensional image.

It is noted that processor 460 monitors the travel speed of imaging catheter 452 during the scanning process, according to data received from MPS 456. It is noted that a predetermined number of two-dimensional images, per travel of the imaging detector 470, is required, so as to fill the three-dimensional volume with enough image data. Some image detectors can only detect so many images in a given time period. Hence, processor 460 detects that the travel speed of imaging detector 470 catheter 452 is equal to or below a predetermined threshold, which determines that the image detector 470 detected enough two-dimensional images, for any given portion of the inspected volume. If processor 460 detects that the travel speed of imaging detector 470 is above a predetermined threshold, then processor 460 produces an alarm signal to notify the operator that the scan is unacceptable or should be repeated, partially or completely. The operator then repeats the scanning process. The type of the alarm signal is audio, visual, tactile, and the like.

The term "surgical procedure" herein below, refers to an in vivo operation on an organ of the patient, such as performing an incision, collecting a sample of a tissue, collecting a sample of bodily fluids, introducing a chemical substance into the organ, introducing a surgical tool or device, and the like.

Figure 16A:
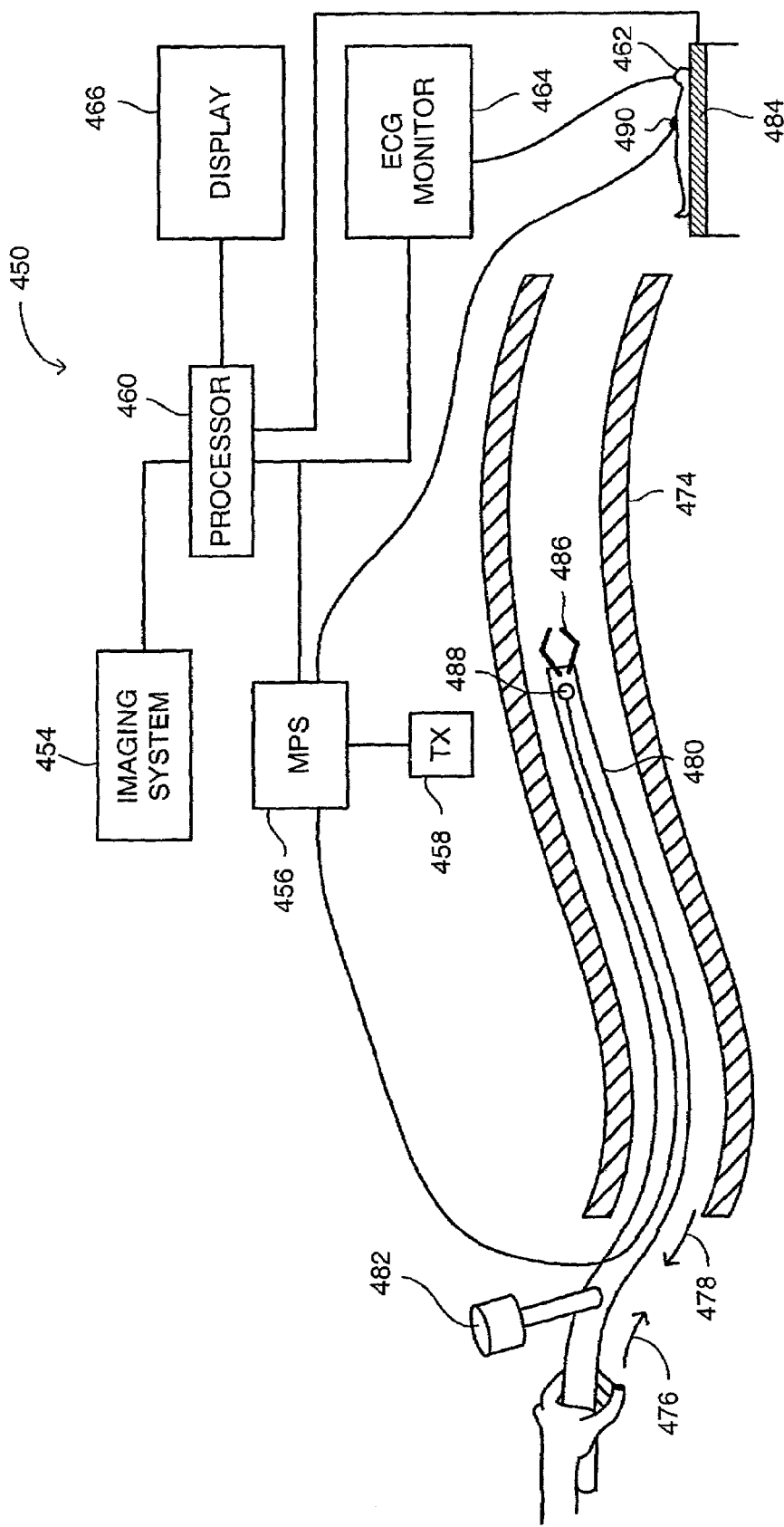
FIG. 16A is a schematic illustration of the system of FIG. 15A, further adapted for surgical procedure.
Figure 16B:
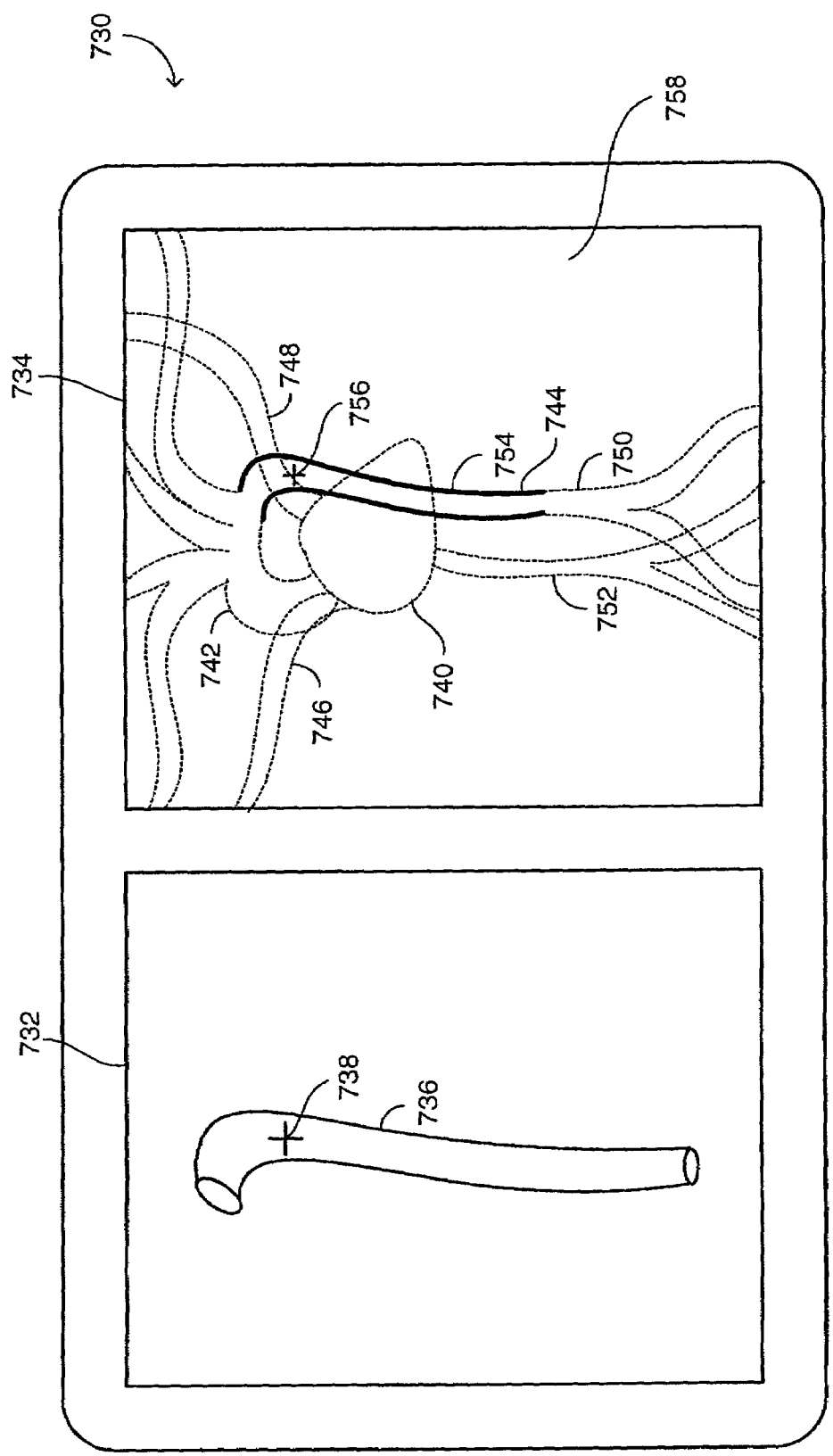
FIG. 16B is a schematic illustration of a graphical user interface (GUI), constructed and operative in accordance with a further preferred embodiment of the present invention.
Figure 16C:
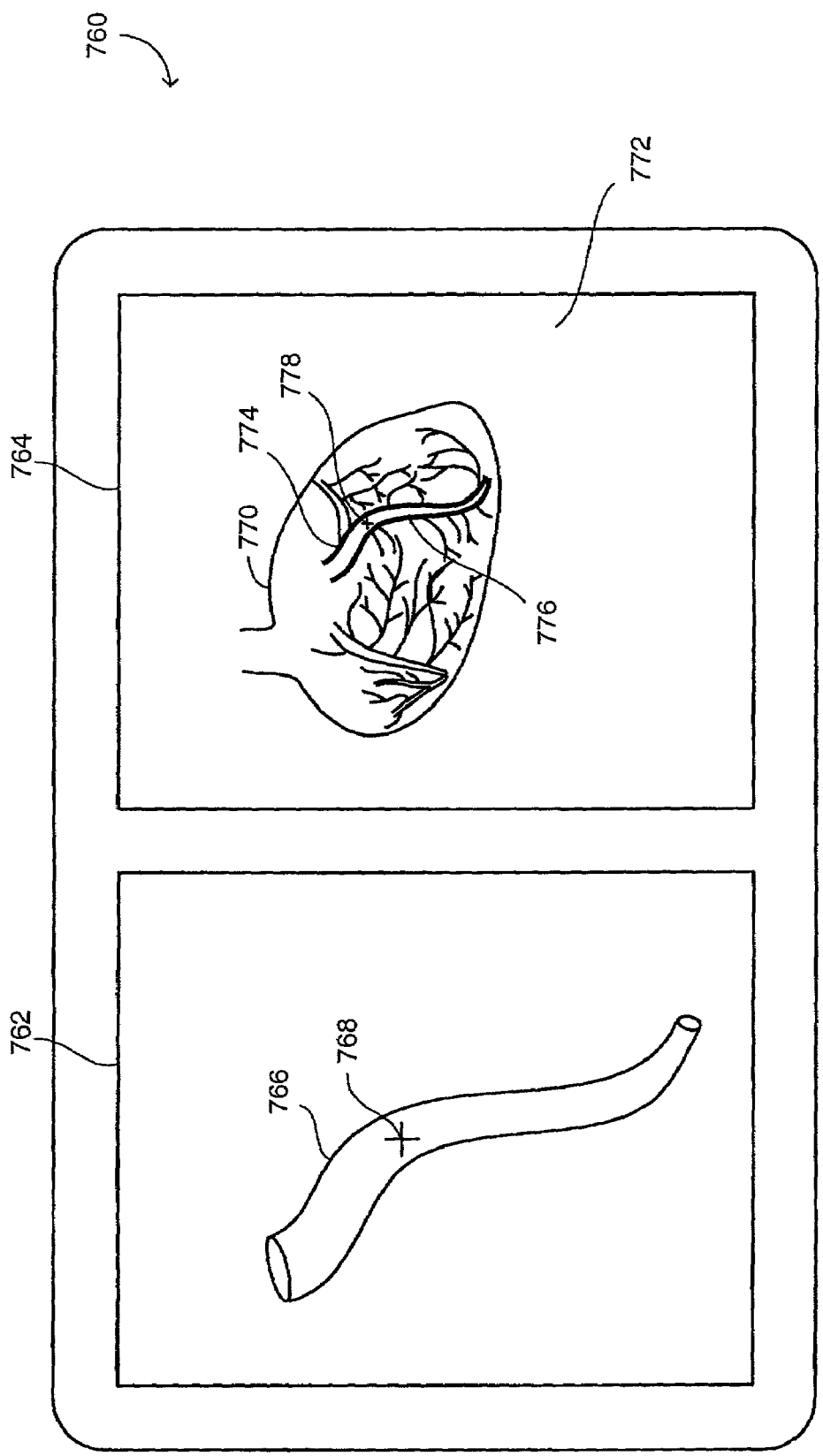
FIG. 16C is a schematic illustration of a GUI, constructed and operative in accordance with another preferred embodiment of the present invention.
Figure 16D:
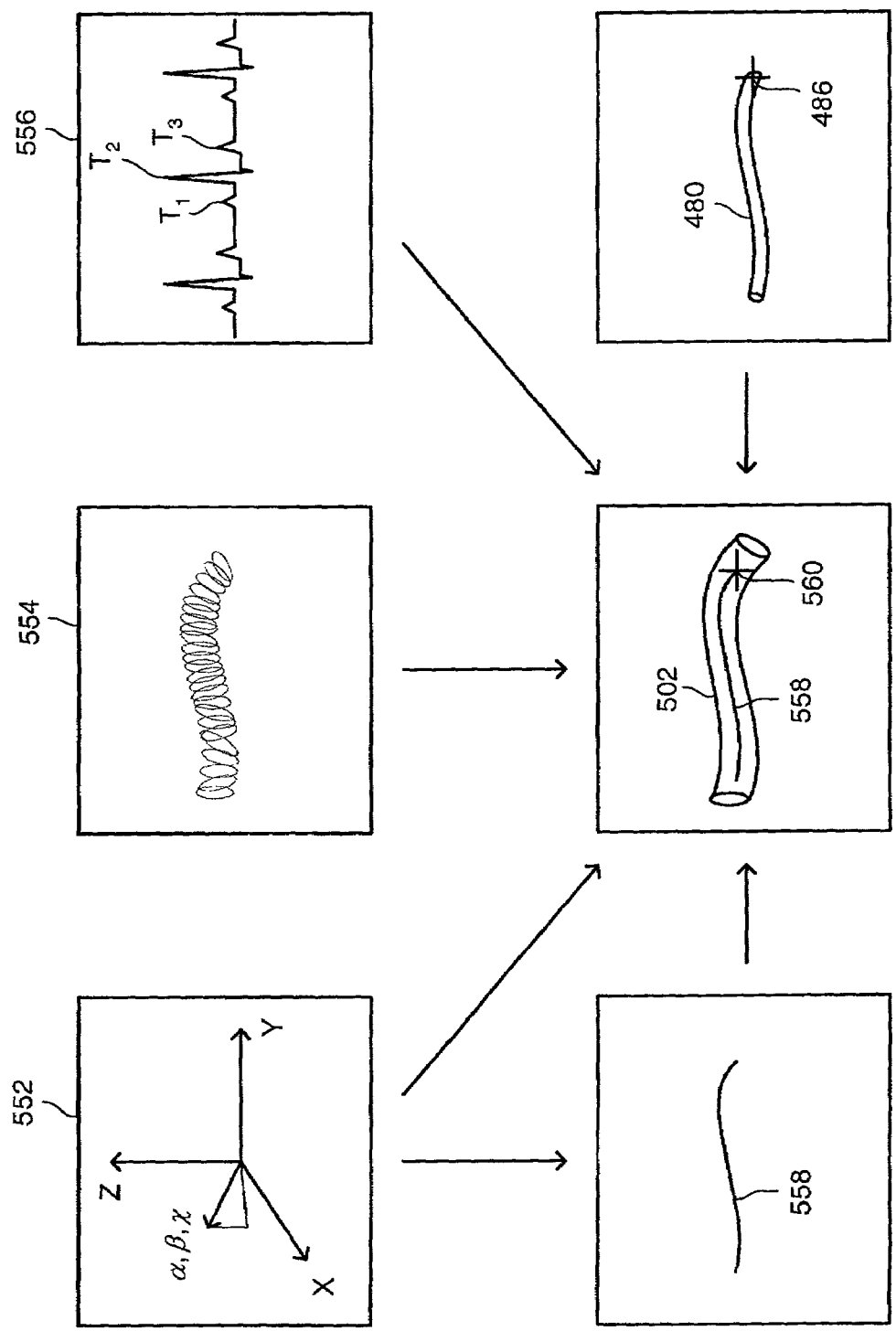
FIG. 16D is a schematic illustration of a process of reconstructing a three-dimensional organ motion dependent image sequence, and superimposing additional visual data thereon.

Reference is now made to FIGS. 16A, 16B, 16C and 16D. FIG. 16A is a schematic illustration of the system of FIG. 15A, further adapted for surgical procedure. FIG. 16B is a schematic illustration of a graphical user interface (GUI), generally referenced 730, constructed and operative in accordance with a further preferred embodiment of the present invention. FIG. 16C is a schematic illustration of a GUI, generally referenced 760, constructed and operative in accordance with another preferred embodiment of the present invention. FIG. 16D is a schematic illustration of a process of reconstructing a three-dimensional organ motion dependent image sequence, and superimposing additional visual data thereon, by processing the signals received from the imaging system, the MPS and the ECG monitor. The additional visual data can include the location of surgical equipment within the inspected organ, the trajectory of a catheter within the inspected organ, and the like.

With reference to FIG. 16A, system 450 further includes a surgical catheter 480, a guidance unit 482 and a real-time imaging system 484. Surgical catheter 480 further includes a surgical tool 486 and a catheter MPS sensor 488 at the tip thereof. Surgical tool 486 is one of a variety of interchangeable surgical devices, which can be mounted onto surgical catheter 480. It is noted that surgical tool 486 is a conventional tool, such as clamp, laser cutter, brush, catheter, stent, balloon, pace maker electrode, ablation catheter, electrophysiological mapping device, solution dispensing unit, neuron electrode, substance collection unit, surgical delivery tool (e.g., for delivering genes, drugs, devices and the like), endoscope, imaging device, and the like, or a combination thereof. For example, a device delivery tool can be a medical tool for delivery of a medical device, such as a permanent stent, a removable stent, and the like, to the body of patient 462. Catheter MPS sensor 488 is coupled to MPS 456.

Guidance unit 482 is coupled to surgical catheter 480. Guidance unit 482 is a device for navigating surgical catheter 480 within inspected organ 474 in space. Real-time imaging system 484 is an imaging system which constantly provides a real time image of that portion of the body of patient 462, which includes inspected organ 474. Real-time imaging system 484 is an X-ray table, a fluoroscopic unit, an ultrasound system, an MRI system and the like. In the present example, real-time imaging system 484 is located either under or above the body of patient 462 and is coupled to processor 460.

When the operator completes scanning inspected organ 474 (FIG. 15A) and processor 460 produces three-dimensional images of inspected organ 474, imaging catheter 452 can be removed from inspected organ 474. Surgical catheter 480 is then inserted in inspected organ 474, in order to perform a surgical procedure on inspected organ 474.

System 450 can play back the stored three-dimensional images in synchrony with the stored organ timing signal of the patient or sequentially, at any speed. System 450 can also be used during surgical procedures wherein system 450 plays back the stored three-dimensional images in synchrony with the real-time organ timing signal of the patient. System 450 can introduce additional information to the played back sequence of three-dimensional images. This additional information can include a representation of a surgical tool, a trajectory of the surgical tool, which was calculated during the scanning process, real time imaging data, and the like.

During the surgical procedure, MPS 456 determines the real-time location and orientation of surgical tool 486, according to signals received from catheter MPS sensor 488, and MPS 456 provides MPS coordinate data respective of this location and orientation, to processor 460. Real-time imaging system 484 acquires a real-time image of the body of patient 462 and provides real-time image data to processor 460. ECG monitor 464 detects the activity of the heart of patient 462 and provides real-time ECG data to processor 460. Processor 460 selects a three-dimensional image of the inspected organ 474, from a database, such as adaptive volumetric database 114 (FIG. 1), according to the real-time detected activity-state of the heart of patient 462 during the surgical procedure.

Processor 460 selects a trajectory from the trajectories, which were calculated during the scanning process, according to the real-time detected activity-state of the heart of patient 462. Processor 460 superimposes this selected trajectory on the selected three-dimensional image. Once the coordinate system of the surgical tool MPS sensor and the coordinate system of the pre-stored three-dimensional image sequence, are aligned, processor 460 can add a representation of the surgical tool on the three-dimensional image sequence.

It is noted that processor 460 can further alter the visual representation of the trajectory according to the location of the surgical tool. For example, processor 460 can set a selected color to a portion of the trajectory from the location of the surgical tool tip backward, in one color, thereby indicating the previous path of the surgical catheter. Similarly, processor 460 can set a different color to the portion of the trajectory from the location of the surgical tool tip forward, thereby indicating a theoretical path of the surgical catheter, should the physician move it forward.

Display 466 displays a graphical user interface (GUI) according to the video signals received from processor 460. This GUI can include a variety of medical information respective of an inspected organ of a patient, thereby facilitating the interaction of the user with the inspected organ. The GUI can include different windows which display images of the inspected organ from different views, or as detected by different types of image detectors. In addition, the GUI can include information respective of the organ timing signal and provisions to view different views of the inspected organ corresponding to different activity-states of the organ. The GUI can include auxiliary information, such as the location and orientation of a surgical tool in real-time, the trajectory of the surgical tool in the past and in the future, and the like.

In the example set forth in FIG. 16B, GUI 730 includes windows 732 and 734. Window 732 includes a reconstructed external three-dimensional navigation image 736 of an inspected organ. It is noted that this external three-dimensional image can be reconstructed in a semi-transparent manner, such that the near wall is colored in a transparent fashion and hence, the far wall can be seen through the near wall.

The inspected organ in this example is the descending aorta 744 of patient 462. Window 732 further includes a representation 738 of a surgical tool, similar to surgical tool 486, superimposed on external three-dimensional navigation image 736.

External three-dimensional navigation image 736 is the real-time three-dimensional sequence of images of descending aorta 744, corresponding to the real-time detected activity-state of the heart of patient 462. Processor 460 superimposes representation 738 of surgical tool 486 in real-time, on external three-dimensional navigation image 736, according to real-time coordinate data which processor 460 receives from MPS 456. Thus, representation 738 indicates the current location and orientation of surgical tool 486 within descending aorta 744.

According to another aspect of the invention, processor 460 selects a three-dimensional image of the inspected organ, according to the organ real-time detected activity-state and superimposes a projection of the selected three-dimensional image on the real-time two-dimensional navigation image. In the example set forth in FIG. 16B, GUI 734 includes a real-time two-dimensional navigation image 758 of the region of the body of the patient, which is under operation. In this example, this region includes the heart 740 of patient 462 and the veins and arteries which are coupled to heart 740, such as the ascending artery 742, descending aorta 744, superior vena cava 746, pulmonary trunk 748, abdominal aorta 750 and inferior vena cava 752.

Processor 460 superimposes a projection 754 of reconstructed three-dimensional image 736 on real-time two-dimensional navigation image 758, which is acquired by real-time imaging system 484, thereby producing the combined two-dimensional image presented in window 734. Processor 460 further superimposes representation 756 of surgical tool 486 on real-time two-dimensional navigation image 758. Representation 756 indicates the current location and orientation of surgical tool 486 within descending aorta 744. Processor 460 selects projection 754, in real-time according to a real-time detected activity-state of the heart of patient 462 and hence follows the visual activity of real-time two-dimensional navigation image 758.

It is noted that the location of real-time imaging system 484 relative to the origin of the global coordinate system is determined either according to a fixed predetermined location relative to transmitter 458, or according to an MPS sensor coupled to real-time imaging system 484.

Processor 460 superimposes two-dimensional image 754 on the actual location of descending aorta 744, in real-time two-dimensional navigation image 758, according to the MPS coordinate data acquired during the scanning process (FIG. 15A). In this manner, the operator can navigate surgical catheter 480 within descending aorta 744, with the aid of guidance unit 482, by observing the instantaneous location and orientation of surgical catheter 480, on a highlighted portion of the body of patient 462 (i.e., on projection 754 in window 734).

With reference to FIG. 16C, GUI 760 includes windows 762 and 764. Window 762 includes a reconstructed external three-dimensional navigation image 766 of another inspected organ of patient 462. In this case, the inspected organ is the left main and left anterior descending (LM & LAD) coronary artery 776 of the heart 770 of patient 462. Window 762 further includes a representation 768 of a surgical tool, similar to surgical tool 486, superimposed on external three-dimensional navigation image 766.

Window 764 includes a real-time two-dimensional navigation image 772 of the heart 770. Heart 770 includes LM & LAD coronary artery 776. Processor 460 superimposes a projection 774 of reconstructed three-dimensional image 766 on real-time two-dimensional navigation image 772, which is acquired by real-time imaging system 484, thereby producing the combined two-dimensional image presented in window 764. Processor 460 further superimposes a representation 778 of surgical tool 486 on real-time two-dimensional navigation image 772. Representation 778 indicates the current location and orientation of surgical tool 486 within LM & LAD coronary artery 776.

Following is a graphical representation of the process by which processor 460 generates a three-dimensional image, including auxiliary information, such as the trajectory of a surgical tool, a representation of the surgical tool, and the like. Processor 460 generates the three-dimensional image by processing different data, such as the detected image data, the MPS coordinate data, the organ timing data, and the like.

With reference to FIG. 16D, processor 460 reconstructs three-dimensional image 502 of inspected organ 474, from a plurality of two-dimensional images 554, according to MPS coordinate data 552, all of which respective of a selected activity state within the cycles of EGG data 556. Processor 460 reconstructs three-dimensional image 502 from all the two-dimensional images which belong to of activity-state $T_2$. In addition, processor 460 generates a trajectory 558 of imaging catheter tip, which corresponds to activity-state $T_2$, from points 514, 520 and 526.

System 450 can playback the sequence of reconstructed images or a selected cycle of the originally acquired two-dimensional images, according to the stored EGG data or at predetermined time intervals. System 450 can also playback the sequence of reconstructed images or a selected cycle of the originally acquired two-dimensional images, in synchrony with real-time detected EGG data.

It is noted that since the surgical tool moves within the inspected organ in real-time, no synchronization is required with respect to the organ timing signal in that aspect. However, it is noted that processor 460 has to register the coordinate system in which the images were acquired, with the coordinate system of the MPS sensor of the surgical tool, or to use the same MPS system for the image acquisition process and the playback surgical procedure.

Figure 17:
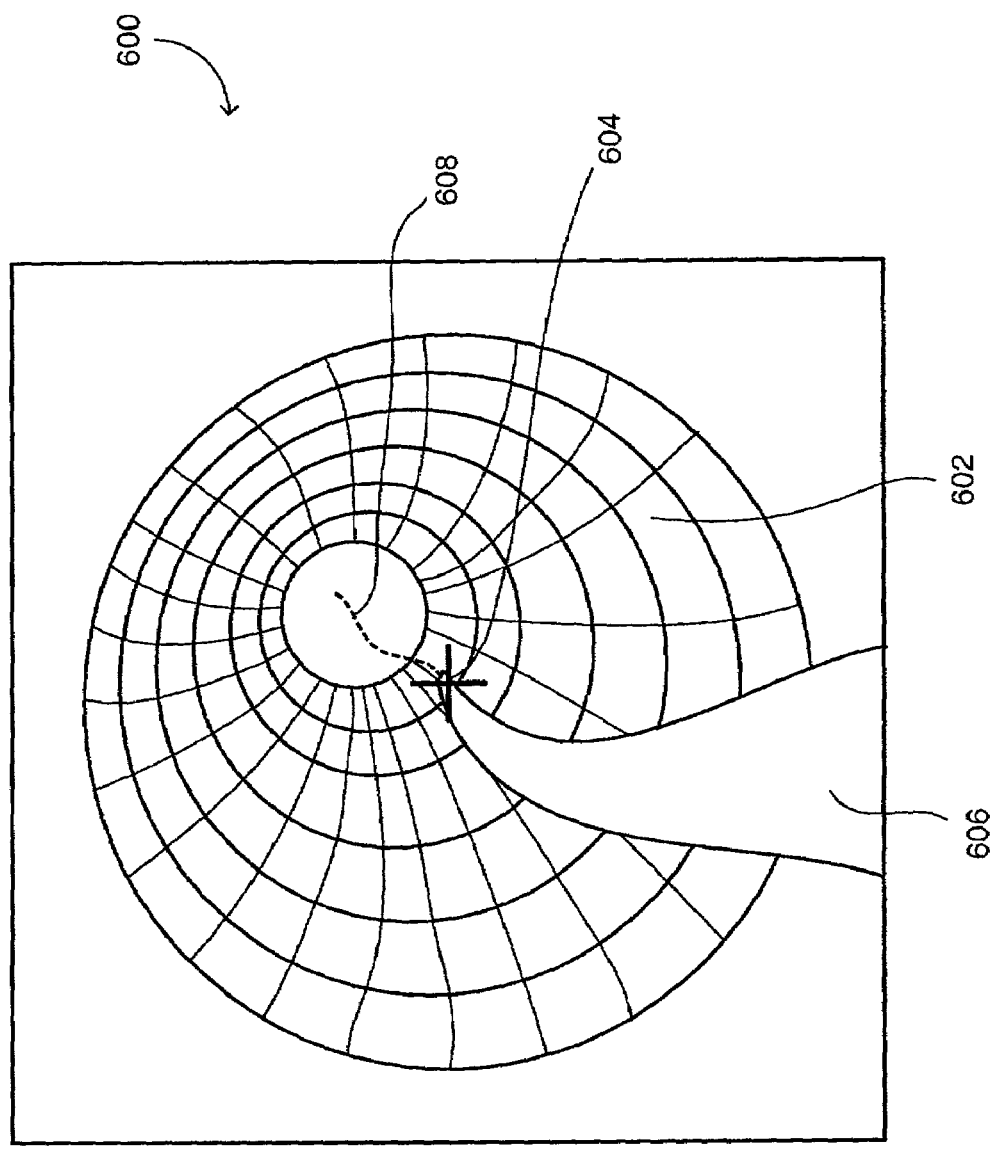
FIG. 17 is a schematic illustration of an internal three-dimensional navigation image of an inspected organ, constructed and operative in accordance with a further preferred embodiment of the present invention.

Reference is now made to FIG. 17, which is a schematic illustration of an internal three-dimensional navigation image of an inspected organ, generally referenced 600, constructed and operative in accordance with a further preferred embodiment of the present invention. Internal three-dimensional navigation image 600 includes an inner wall image 602 of an inspected organ, such as inspected organ 474 (FIG. 15A), as if the operator was located inside the inspected organ. Internal three-dimensional navigation image 600 further includes a surgical tool representation 604 of the current location of a surgical tool, such as surgical tool 486 (FIG. 16A), during the surgical operation. Internal three-dimensional navigation image 600 further includes surgical catheter representation 606 of the surgical catheter viewed from behind the current location of the surgical tool. Internal three-dimensional navigation image 600 further includes a trajectory representation 608 of the future trajectory of an imaging catheter, such as imaging catheter 452 (FIG. 15A), following the current location of the surgical tool, as viewed from the current location of the surgical tool.

Inner wall image 602 is the image of the inspected organ, surrounding image detector 470. Trajectory representation 608 represents the trajectory which the tip of the imaging catheter had traveled within the inspected organ, during the scanning process (FIG. 15A). Trajectory representation 608 displays the theoretical forward path, which the surgical catheter will follow within the inspected organ, should the operator advance the surgical catheter forward within the inspected organ.

Figure 18:
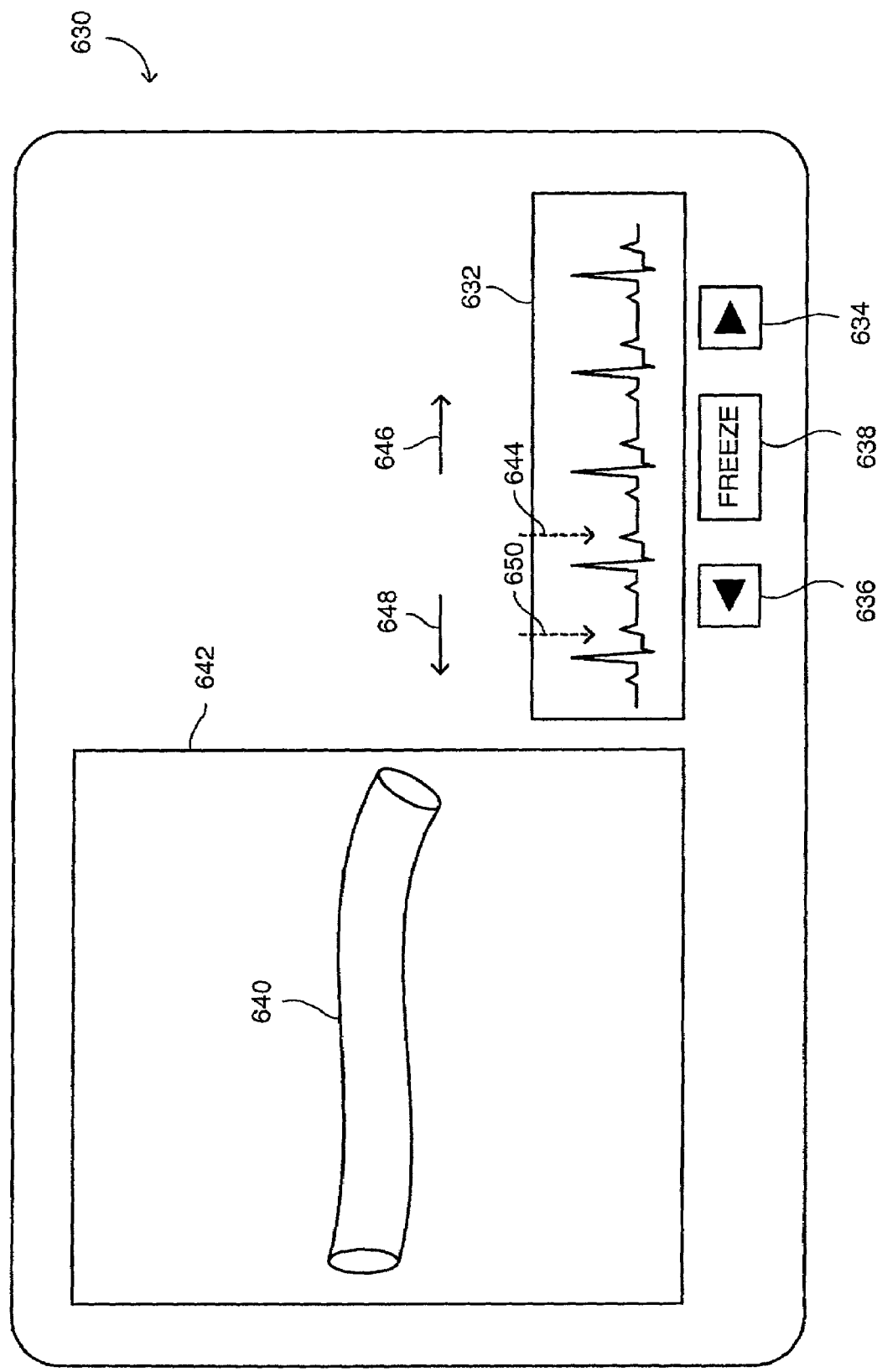
FIG. 18 is a schematic illustration of an ECG coordinated display of an inspected organ, constructed and operative in accordance with another preferred embodiment of the present invention.

Reference is now made to FIG. 18, which is a schematic illustration of an ECG coordinated display of an inspected organ, generally referenced 630, constructed and operative in accordance with another preferred embodiment of the present invention. ECG coordinated display 630 includes an ECG timing signal 632, a forward button 634, a backward button 636, a freeze button 638 and an external three-dimensional image 640 of an inspected organ, such as inspected organ 474 (FIG. 15A).

External three-dimensional image 640 is displayed in a window 642 and corresponds with an activity-state 644 in ECG timing signal 632. When the operator presses forward button 634, a sequence of external three-dimensional images of the inspected organ is displayed in window 642. Each of the external three-dimensional images displayed in window 642, corresponds with the respective activity-state in ECG timing signal 632, as if ECG timing signal 632 would advance in a direction designated by an arrow 646.

When the operator presses backward button 636, a sequence of external three-dimensional images of the inspected organ is successively displayed in window 642. Each of the external three-dimensional images displayed in window 642 corresponds with the respective activity-state in ECG timing signal 632, as if ECG timing signal 632 would retard in a direction designated by an arrow 648.

When the operator presses freeze button 638, an external three-dimensional image of the inspected organ is displayed in window 642, wherein the external three-dimensional image corresponds with a selected activity-state 650. In this manner the external three-dimensional image of the inspected organ in window 642 remains stationary at activity-state 650, during which the physician can inspect the three-dimensional image of the inspected organ.

Each of the external three-dimensional images, which are displayed in window 642, is acquired by system 450 (FIG. 15A), during the scanning process. Thus, the operator can view animated external three-dimensional images of the inspected organ as the heart of the patient would beat either forward or backward in time. The operator can alternatively view an external three-dimensional image of the inspected organ, which corresponds with a selected activity-state during a selected heart cycle of the patient, by pressing freeze button 638 at a selected point in time. It is noted that other sequenced images, such as a reference real-time image (i.e., served as road map during navigation, such as a fluoroscopic image, and the like) can also be made to freeze-up.

Figure 19A:
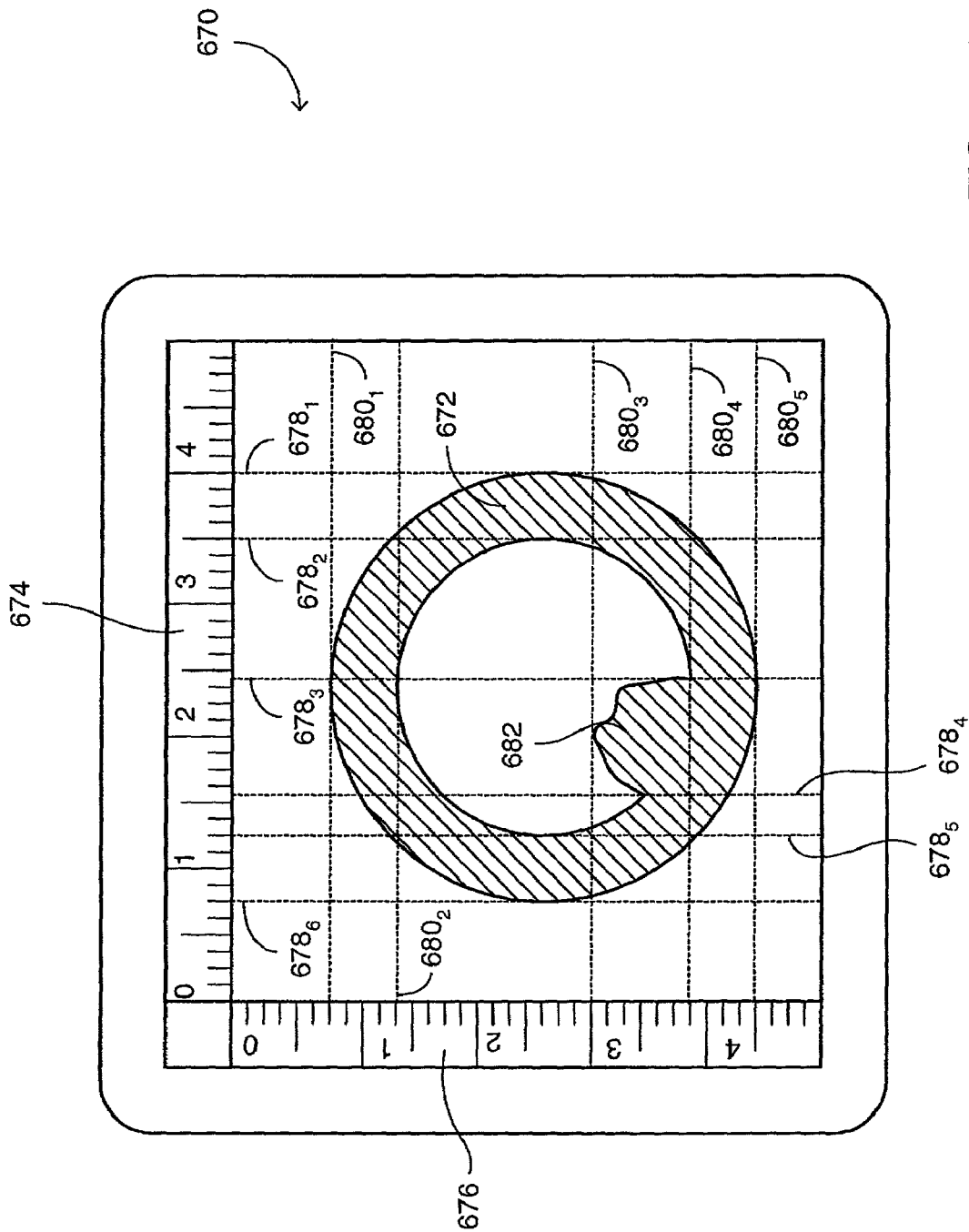
FIG. 19A is a schematic illustration of a GUI, constructed and operative in accordance with a further preferred embodiment of the present invention.
Figure 19B:
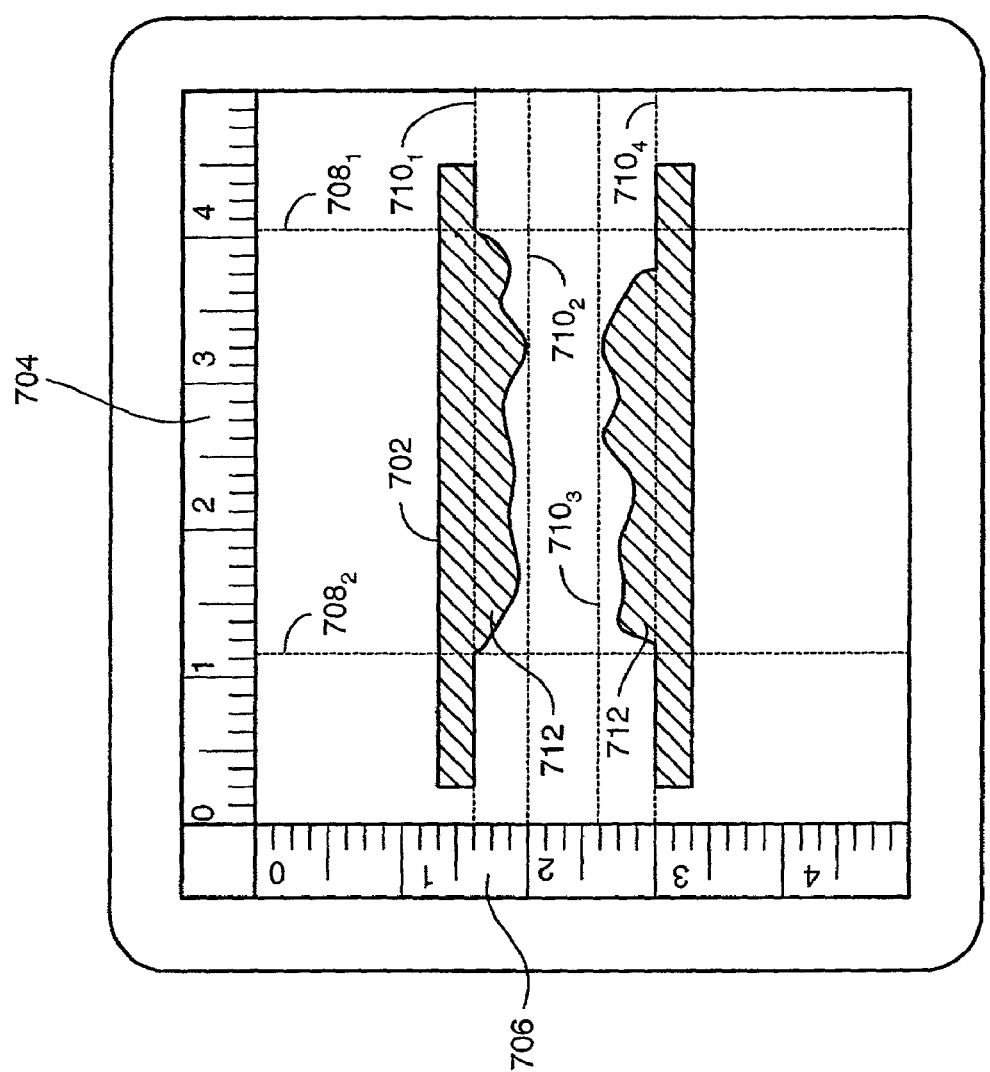
FIG. 19B is a schematic illustration of a GUI, constructed and operative in accordance with another preferred embodiment of the present invention.

Reference is now made to FIGS. 19A and 19B. FIG. 19A is a schematic illustration of a GUI, generally referenced 670, constructed and operative in accordance with a further preferred embodiment of the present invention. FIG. 19B is a schematic illustration of a GUI, generally referenced 700, constructed and operative in accordance with another preferred embodiment of the present invention.

With reference to FIG. 19A, GUI 670 includes a transverse cross sectional image 672 of an inspected organ, a horizontal ruler 674, a vertical ruler 676, a plurality of vertical guides 678$_1$, 678$_2$, 678$_3$, 678$_4$, 678$_5$ and 678$_6$, and a plurality of horizontal guides 680$_1$, 680$_2$, 680$_3$, 680$_4$ and 680$_5$. Transverse cross sectional image 672 includes an image of a plaque 682. The operator measures the geometrical parameters of the inspected organ, such as diameter, area, percent occlusion, and the like, by reading the location of vertical guides 678$_1$, 678$_2$, 678$_3$, 678$_4$, 678$_5$ and 678$_6$, and horizontal guides 680$_1$, 680$_2$, 680$_3$, 680$_4$ and 680$_5$ on horizontal ruler 674, and vertical ruler 676, respectively. The operator also measures the size of plaque 682. Alternatively, the geometrical parameters are written on GUI 670. Further alternatively, the geometrical parameters are announced via a speaker.

With reference to FIG. 19B, GUI 700 includes a longitudinal cross sectional image 702 of an inspected organ, a horizontal ruler 704, a vertical ruler 706, a plurality of vertical guides 708$_1$ and 708$_2$, and a plurality of horizontal guides 710$_1$, 710$_2$, 710$_3$ and 710$_4$. Longitudinal cross sectional image 702 includes a plaque 712. The operator measures the geometrical parameters of the inspected organ, such as diameter, area, percent occlusion, and the like, by reading the location of vertical guides 708$_1$ and 708$_2$, and horizontal guides 710$_1$, 710$_2$, 710$_3$ and 710$_4$ on horizontal ruler 704 and vertical ruler 706, respectively. The operator also measures the size of plaque 712. Alternatively, the geometrical parameters are written on GUI 700. Further alternatively, the geometrical parameters are announced via a speaker.

Figure 20:
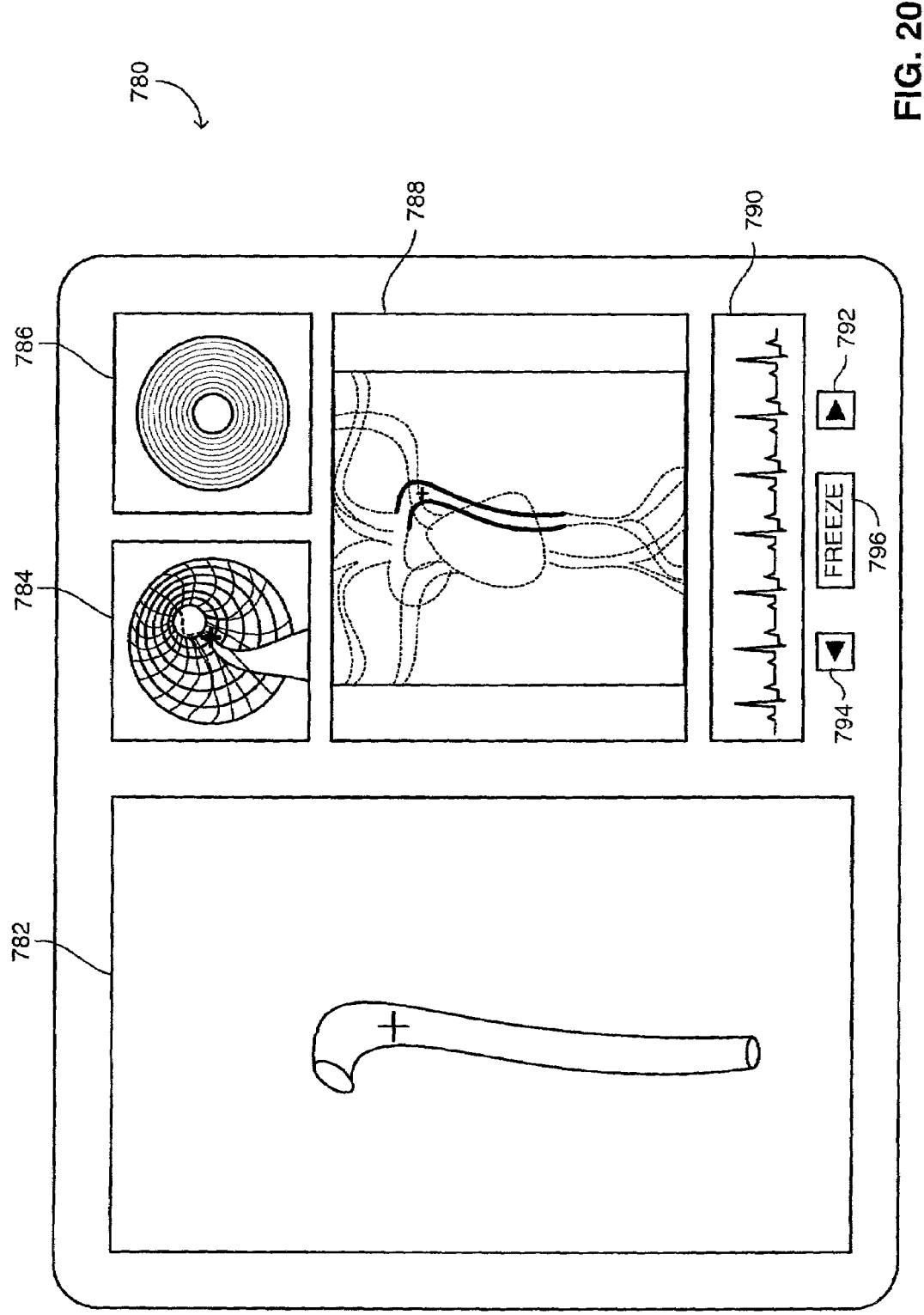
FIG. 20 is a schematic illustration of a GUI, constructed and operative in accordance with a further preferred embodiment of the present invention.

Reference is now made to FIG. 20, which is a schematic illustration of a GUI, generally referenced 780, constructed and operative in accordance with a further preferred embodiment of the present invention. GUI 780 includes windows 782, 784, 786 and 788, an ECG timing signal 790, a forward button 792, a backward button 794 and a freeze button 796. GUI 780 provides a quantitative model, by which the user acquires a realistic notion of the navigation process within the body of the patient.

Window 782 is similar to window 732 of FIG. 16B. Window 784 includes an image similar to the internal image of an inspected organ 600 of FIG. 17.

Window 786 includes historical two-dimensional information of the inspected organ, while the image detector is located inside the inspected organ. Window 788 is similar to window 734 of FIG. 16B. ECG timing signal 790 is similar to ECG timing signal 632 of FIG. 18. Forward button 792, backward button 794 and freeze button 796, are similar to forward button 634, backward button 636 and freeze button 638, respectively, of FIG. 18.

Figure 21:
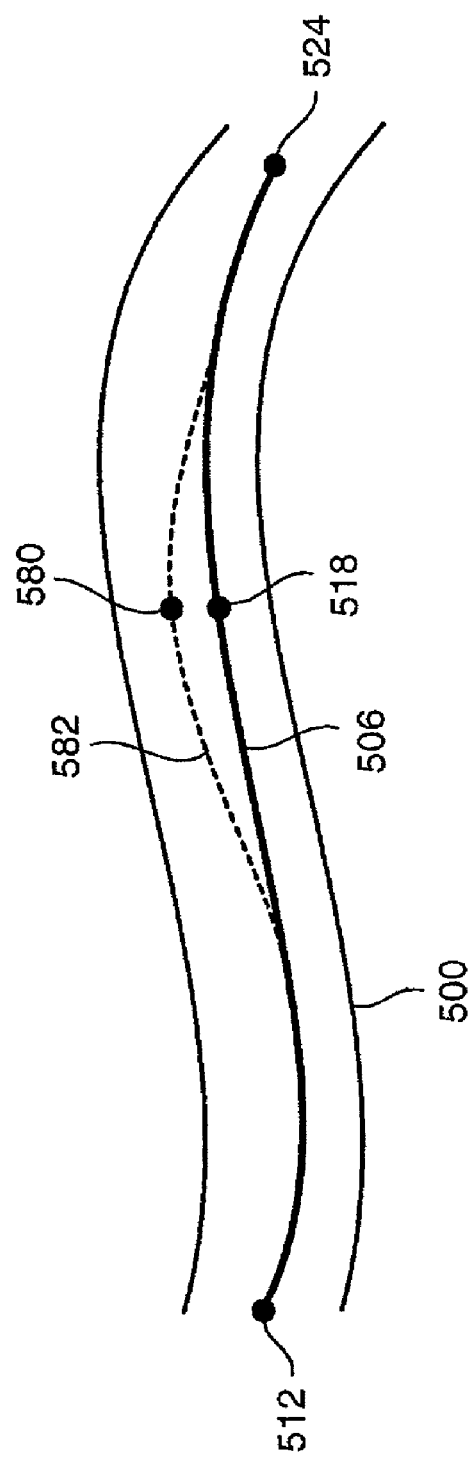
FIG. 21 is a schematic illustration of a trajectory, corrected according to the location and orientation of the tip of the surgical tool of the system of FIG. 16A, in accordance with another preferred embodiment of the present invention.

Reference is now made to FIG. 21, which is a schematic illustration of a trajectory, corrected according to the location and orientation of the tip of the surgical tool of the system of FIG. 16A, in accordance with another preferred embodiment of the present invention. During the surgical operation, the operator successively locates surgical tool 486 (FIG. 16A), at points 512, 580 and 524. Points 512 and 524 are located on trajectory 506, which processor 460 generated according to the trajectory of tip 472 of imaging catheter 452 (FIG. 15A), during the scanning process. Trajectory 506 is defined by points 512, 518 and 524 and point 580 is not located on trajectory 506. Processor 460 makes corrections to trajectory 506 and generates a corrected trajectory 582, defined by points 512, 580 and 524 and display 466 displays corrected trajectory 582, accordingly, superimposed on external three-dimensional navigation image 500.

Figure 22:
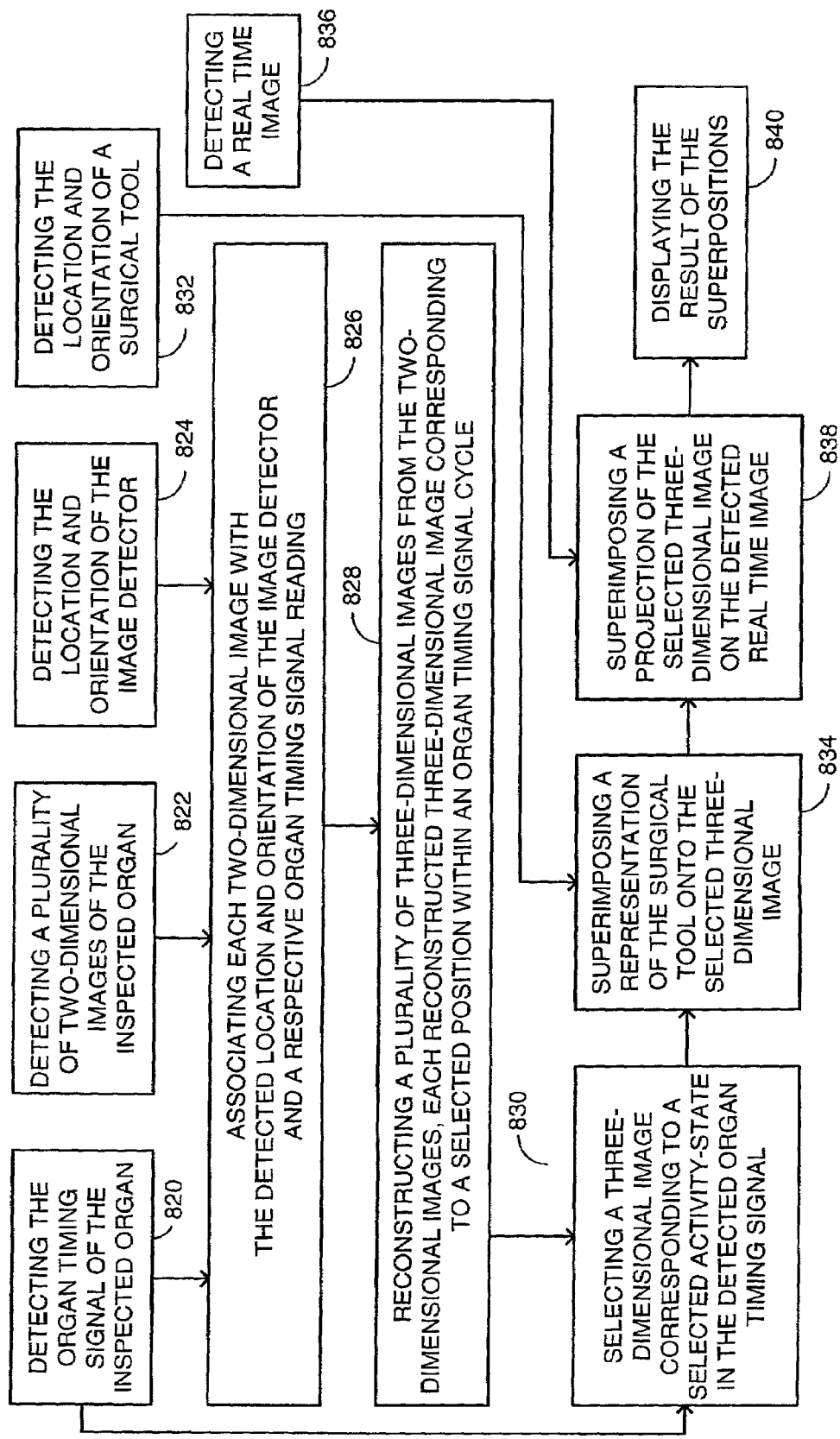
FIG. 22 is a schematic illustration of a method for operating the system of FIG. 15A, operative in accordance with a further preferred embodiment of the present invention.

Reference is now made to FIG. 22, which is a schematic illustration of a method for operating system 450 of FIG. 15A, operative in accordance with a further preferred embodiment of the present invention. In procedure 820, the organ timing signal of the inspected organ is detected. With reference to FIG. 15A, ECG monitor 464 detects the activity-state of the heart of patient 462, such as EGG timing signal 442 (FIG. 14).

In procedure 822, a plurality of two-dimensional images of the inspected organ are detected by an image detector. With reference to FIG. 15A, image detector 470 detects two-dimensional images 554 (FIG. 16D) of inspected organ 474. The image detector can be an ultrasound detector, and OCT detector, MRI device, thermography device, and the like.

In procedure 824, the location and orientation of the image detector is detected. With reference to FIG. 15A, imaging MPS sensor 468 detects the location and orientation of image detector 470.

In procedure 826, each two-dimensional image is associated with the detected location and orientation of the image detector and a respective organ timing signal reading. With reference to FIGS. 15A and 16D, processor 460 associates each of the two-dimensional images 554 with the respective MPS coordinate data 552 of image detector 470 and the respective activity state of the ECG timing signal 556.

In procedure 828, a plurality of three-dimensional images are reconstructed from the two-dimensional images. Each reconstructed three-dimensional image corresponds to a selected position within the organ timing signal cycle. With reference to FIGS. 14, 15A and 15B, processor 460 reconstructs external three-dimensional navigation images 500, 502 and 504, corresponding to activity-states $T_1$, $T_2$ and $T_3$, respectively. When the heart of patient 462 is for example, at activity-state $T_2$, processor 460 selects external three-dimensional navigation image 502 (procedure 830).

In procedure 832, the location and orientation of a surgical tool is detected. With reference to FIG. 16A, catheter MPS sensor 488 detects the location and orientation of surgical tool 486 of surgical catheter 480 and processor 460 superimposes a representation of surgical tool 486, according to the detected location and orientation, onto the selected three-dimensional image (procedure 834).

In procedure 836, a real time image is detected. With reference to FIG. 16A, real-time imaging system 484 detects a real time image of that portion of the body of patient 462, which includes inspected organ 474.

In procedure 838, a projection of the selected three-dimensional image is superimposed on the detected real time image. With reference to FIG. 16B, processor 460 superimposes projection 754 of reconstructed three-dimensional image 736 on real-time two-dimensional navigation image 758. It is noted that the outcome of this procedure yields a quantitative model, which provides the user a very realistic notion of the actual navigation within the body of the patient.

In procedure 840, the result of the superpositions is displayed. With reference to FIGS. 16A and 16B, a superposition of representation 756 of surgical tool 486 on real-time two-dimensional navigation image 758 and a projection 754 of reconstructed three-dimensional image 736 on real-time two-dimensional navigation image 758, are displayed on display 466.

According to another aspect of the present invention, system 450 displays a reconstructed three-dimensional image of the inspected organ, on which the occluded regions are marked. Furthermore, the operator can direct system 450 to mark only those regions of the inspected organ, whose occlusions are equal to or more than a selected limit.

Figure 23A:
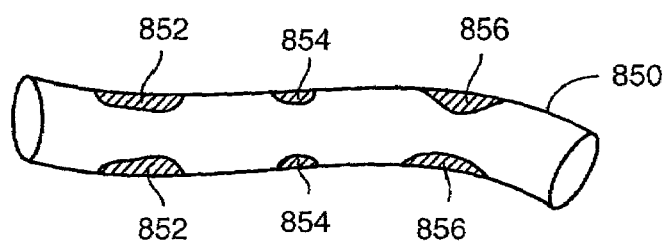
FIG. 23A is an illustration of an artery, having a plurality of occluded regions.
Figure 23B:
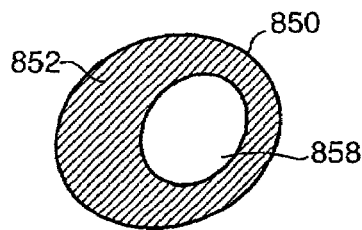
FIG. 23B is a cross-sectional view of a selected region of the artery of FIG. 23A.
Figure 23C:
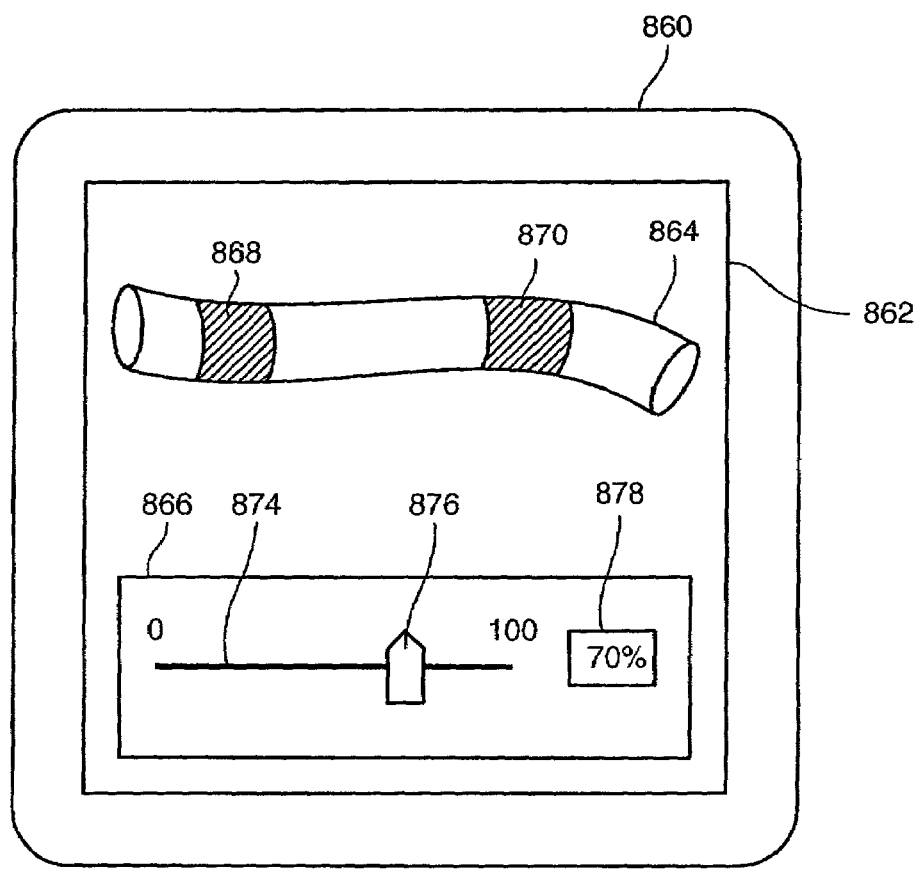
FIG. 23C is a schematic illustration of a representation of the artery of FIG. 23B in a GUI, operative in accordance with another preferred embodiment of the present invention.

Reference is now made to FIGS. 23A, 23B and 23C. FIG. 23A is an illustration of an artery, generally referenced 850, having a plurality of occluded regions. FIG. 23B is a cross-sectional view of a selected region of artery 850 of FIG. 23A. FIG. 23C is a schematic illustration of a representation of the artery of FIG. 23B in a graphical user interface (GUI), generally referenced 860, operative in accordance with another preferred embodiment of the present invention.

Artery 850 includes plaques 852, 854 and 856. It is noted that plaques 852, 854 and 856 can be fixed in their places or be dynamic. Plaques 852, 854 and 856 block artery 850 by 75%, 60% and 80%, respectively. With reference to FIG. 23B, the hatched area denotes the blockage due to plaque 852 within artery 850, leaving lumen 858 open for blood flow.

Processor 460 can determine the percentage of occlusion, according to a plurality of methods, taking into account parameters such as plaque type, plaque density, and the like. The following is a simple example for such a method:

$$\%_{BLOCKED} = \left(1 - \frac{S_{LUMEN}}{S_{ARTERY}}\right) \cdot 100$$

where, $S_{LUMEN}$ denotes the area of lumen 858 and $S_{ARTERY}$ denotes the total internal area of artery 850.

GUI 860 includes a graphical window 862. Graphical window 862 includes a reconstructed three-dimensional image 864 of artery 850 and a ratio selection window 866. Ratio selection window 866 includes a graduation bar 874, a pointer 876 and a numerical box 878. The operator can dynamically set the occlusion percentage threshold, by dragging pointer 876 along graduation bar 874, using a pointing device, such as a mouse, a stylus and a digital tablet, and the like. Alternatively, the operator can enter a selected occlusion percentage threshold in numerical box 878, through a user interface, such as keyboard, microphone, and the like. In the example set forth in FIG. 23B, the numerical value 70%, of the selected percentage is shown in numerical box 878.

System 450 then marks only those regions on reconstructed three-dimensional image 864, which are occluded more than the selected occlusion percentage. In the example set forth in FIG. 23B, only those regions of artery 850 which are occluded 70% or more, are marked in reconstructed three-dimensional image 864. Plaques 852 and 856, which exceed 70%, are represented by marked regions 868 and 870, respectively, on reconstructed three-dimensional image 864. Marked regions 868 and 870 are differentiated from the rest of the portions of reconstructed three-dimensional image 864, by being colored in a different hue, marked by hatches, animated, and the like.

It is noted the system enables the user to manually correct the marking on screen, in case that the user, according to her medical knowledge and experience detects for example, that the plaque portion should be different than what the system indicated. For example, if the user detects that the image presented in window 786 (FIG. 20) provides additional information regarding plaque 852, by which plaque 852 blocks less than what is shown on screen, then the user can mark plaque 852 on screen, accordingly. It is further noted that the system can present the various layers of the lumen (i.e., media, adventitia and intima), in GUI 860, in different colors.

Figure 24:
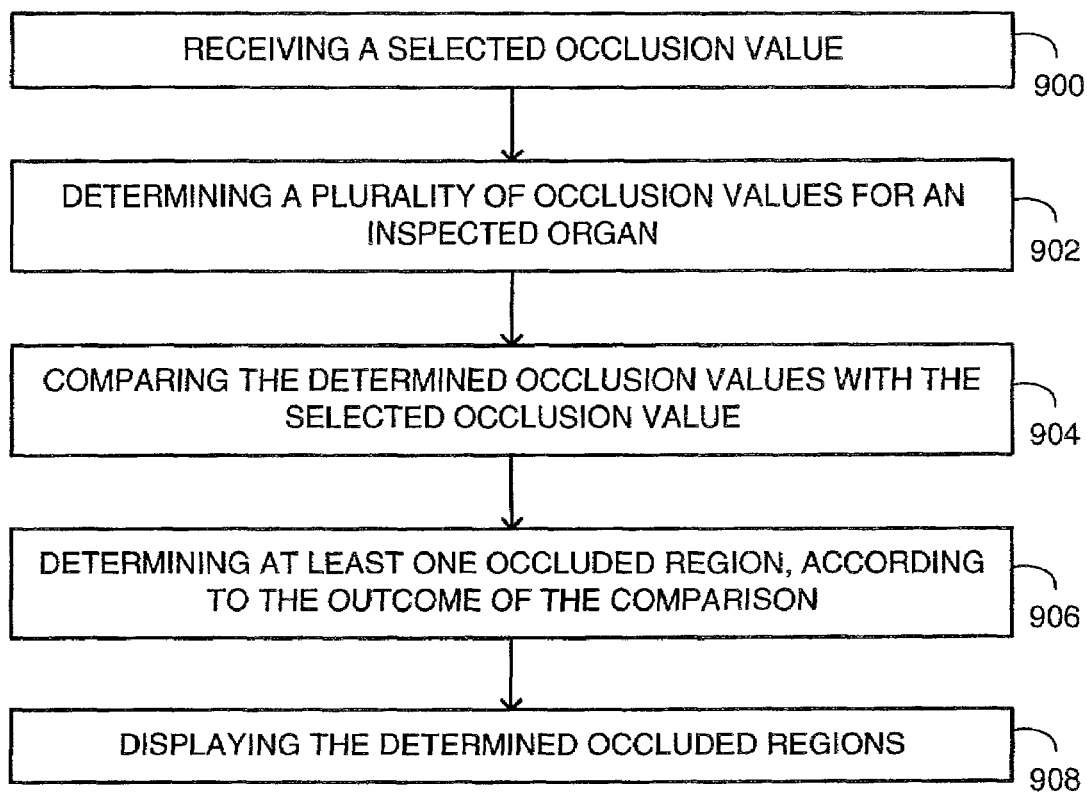
FIG. 24 is a schematic illustration of a method for operating the GUI of FIG. 23C, operative in accordance with a further preferred embodiment of the present invention.

Reference is now made to FIG. 24, which is a schematic illustration of a method for operating the graphical user interface of FIG. 23C, operative in accordance with a further preferred embodiment of the present invention. In procedure 900, an occlusion value is received. With reference to FIG. 23C, the operator sets an occlusion threshold of 70%, via ratio selection window 866 and processor 460 receives this selected occlusion threshold.

In procedure 902, a plurality of occlusion values are determined for an inspected organ. With reference to FIG. 23A, processor 460 determines that plaques 852, 854 and 856 block artery 850 by 75%, 60% and 80%, respectively.

In procedure 904, the determined occlusion values are compared with the selected occlusion value. With reference to FIGS. 23A and 23C, processor 460 compares the percentage occlusions 75%, 60% and 80% of plaques 852, 854 and 856, respectively, with the selected occlusion threshold of 70%.

In procedure 906, at least one occluded region is determined, according to the outcome of the comparison. With reference to FIGS. 23A and 23C, processor 460 determines that plaques 868 and 870 are the occluded regions, which are to be displayed. This is so, because the percentage occlusions of plaques 868 and 870 (75% and 80%, respectively) are greater than the selected occlusion threshold of 70%, while the percentage occlusion of plaque 854 (i.e., 60%) is less than 70%. With reference to FIG. 23C, plaques 852 and 856 are represented as marked regions 868 and 870, respectively, in reconstructed three-dimensional image 864 (procedure 908).

According to another aspect of the invention, the three-dimensional image of an inspected organ at a selected activity-state, is reconstructed from two-dimensional images of the inspected organ, which are detected during other activity-states of the inspected organ. Since more two-dimensional images are available for reconstruction of the three-dimensional image, the processor can reconstruct a more detailed image of the inspected organ at this selected activity-state. It is noted that this aspect of the invention can be applied for organs, which exhibit negligible deformation, or organs with known deformation.

In this case, the inspected organ is a vessel, such as an artery, bronchus, esophagus, and the like, whose geometry remains substantially constant at all activity-states of the organ timing signal, and that only the location and orientation of the vessel changes. The processor incorporates the two-dimensional images of the vessel detected at different activity-states, with the two-dimensional images detected at the selected activity-state, while changing the coordinates (i.e., the locations and orientations) of the incorporated two-dimensional images to those coordinates which were detected during the selected activity-state.

Figure 25A:
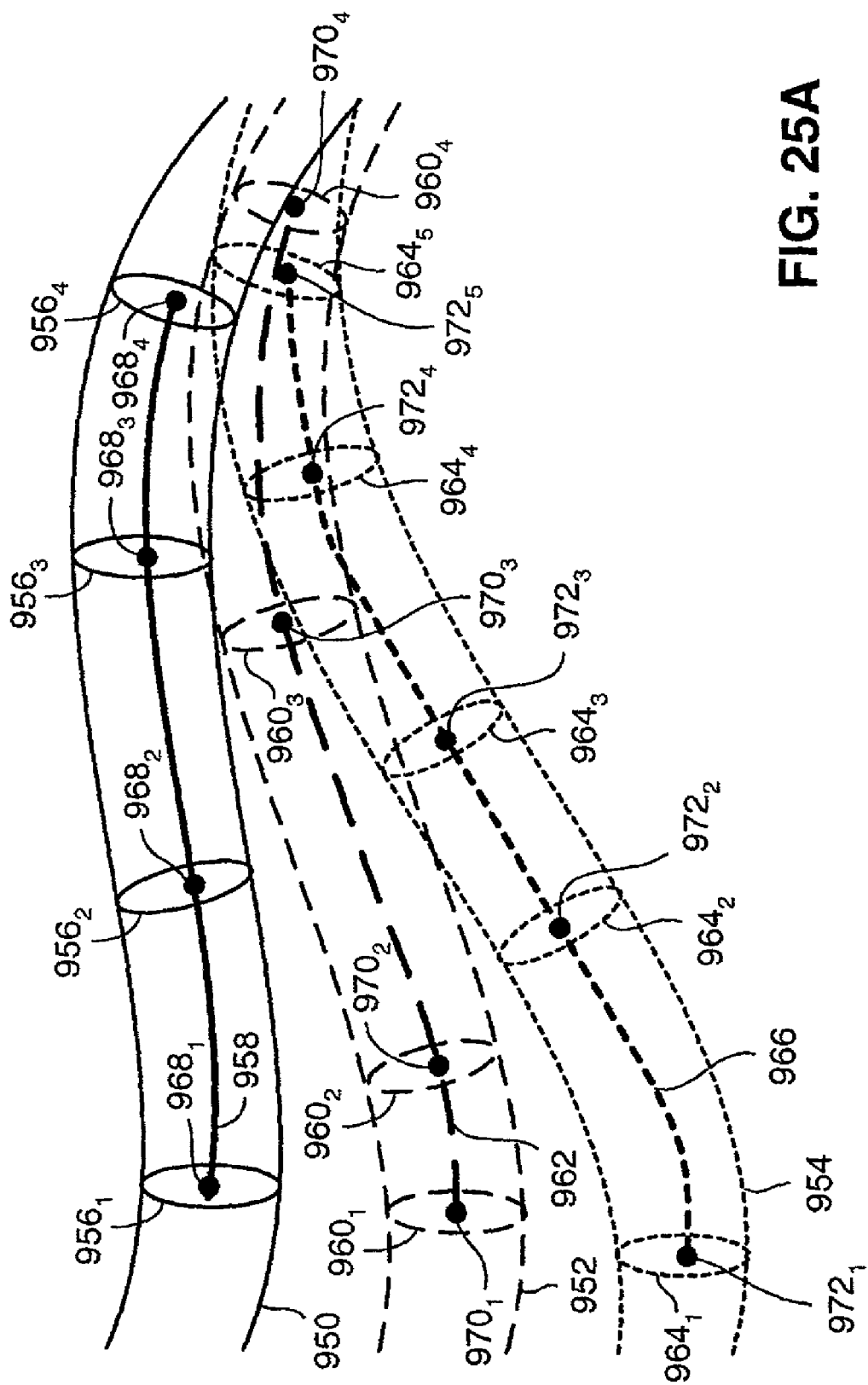
FIG. 25A is a schematic illustration of the images of a vessel at three different activity-states.
Figure 25B:
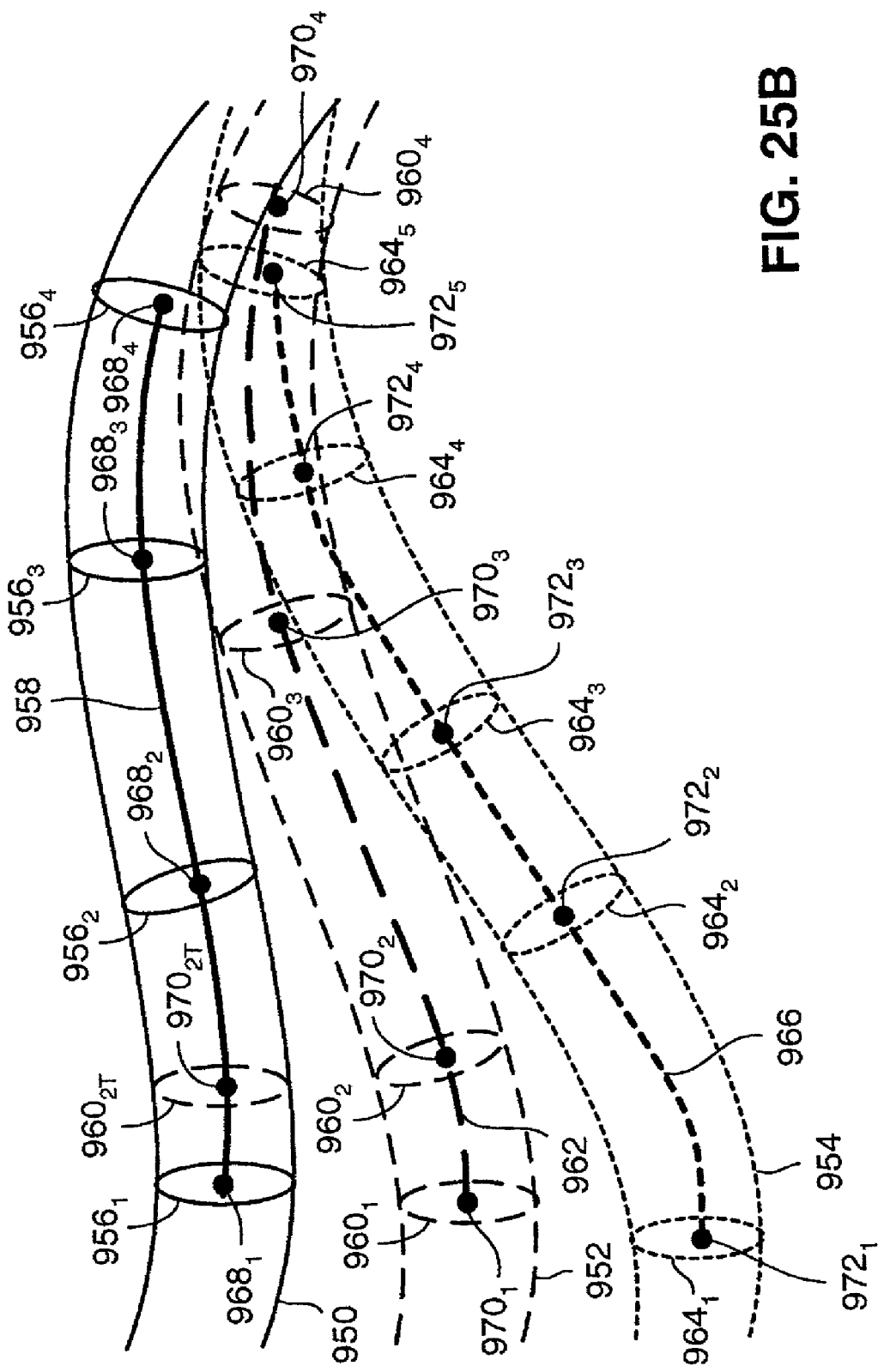
FIG. 25B is a schematic illustration of one of the two-dimensional images acquired at one activity-state, translated to another activity-state, in accordance with another preferred embodiment of the present invention.
Figure 25C:
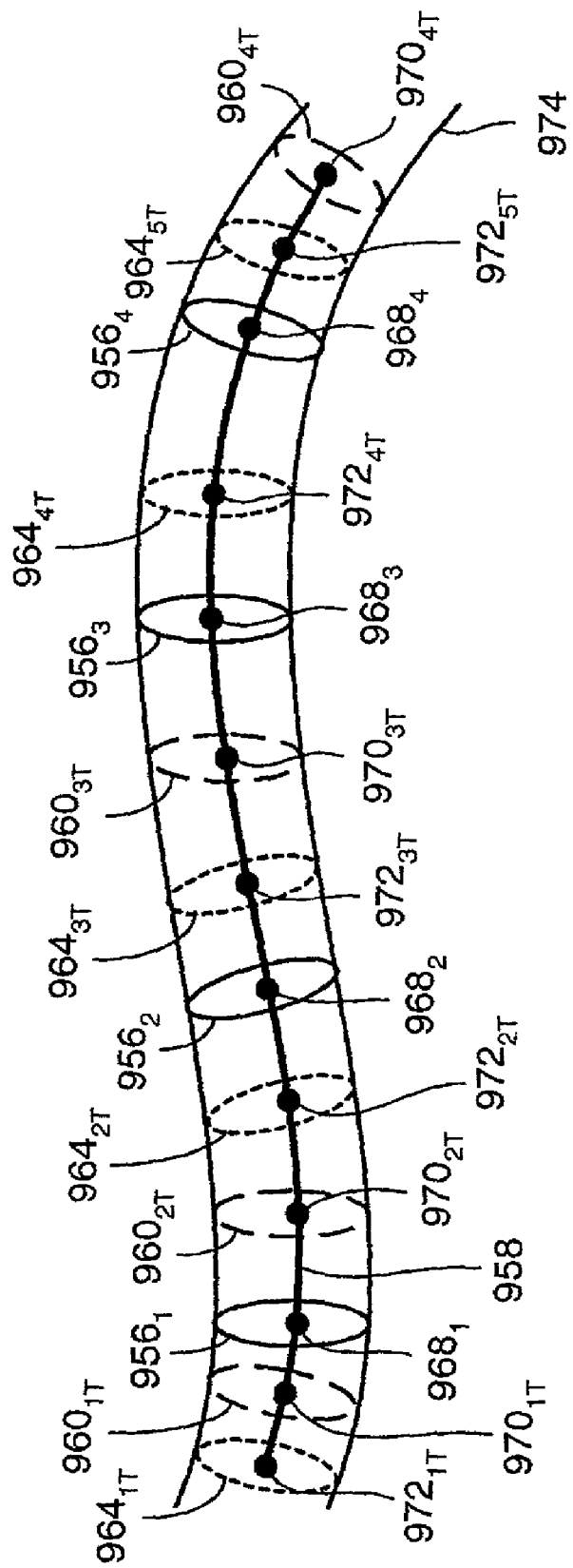
FIG. 25C is a schematic illustration of the image of the vessel of FIG. 25A at one of the activity-states, reconstructed in accordance with the embodiment of FIG. 25B, from the two-dimensional images of the vessel, which are detected at the other two activity-states.
Figure 25D:
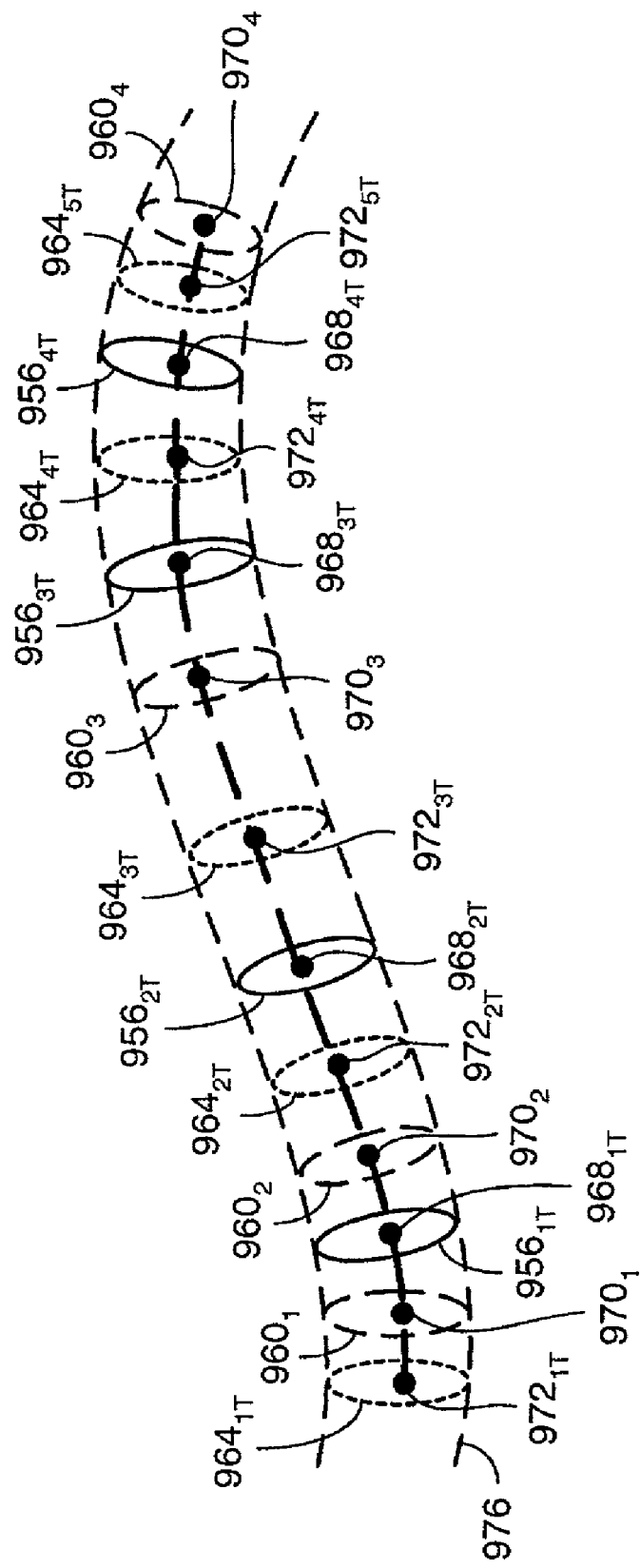
FIG. 25D is a schematic illustration of the image of the vessel of FIG. 25A at another activity-state, reconstructed in accordance with the embodiment of FIG. 25B, from the two-dimensional images of the vessel, which are detected at the other two activity-states.

Reference is now made to FIGS. 25A, 25B and 25C. FIG. 25A is a schematic illustration of the images of a vessel at three different activity-states, generally referenced 950, 952 and 954. FIG. 25B is a schematic illustration of one of the two-dimensional images acquired at one activity-state, translated to another activity-state, in accordance with another preferred embodiment of the present invention. FIG. 25C is a schematic illustration of the image of the vessel of FIG. 25A at one of the activity-states, reconstructed in accordance with the embodiment of FIG. 25B, from the two-dimensional images of the vessel, which are detected at the other two activity-states. FIG. 25D is a schematic illustration of the image of the vessel of FIG. 25A at another activity-state, reconstructed in accordance with the embodiment of FIG. 25B, from the two-dimensional images of the vessel, which are detected at the other two activity-states.

With reference to FIG. 25A, three-dimensional image 950 of inspected organ 474 (FIG. 15A), is reconstructed from two-dimensional images $956_1$, $956_2$, $956_3$, and $956_4$ detected during activity-state $T_1$. The path of imaging catheter 452 during activity-state $T_1$ is represented by a trajectory 958. Three-dimensional image 952 of inspected organ 474 is reconstructed from two-dimensional images $960_1$, $960_2$, $960_3$, and $960_4$ detected during activity-state $T_2$. The path of imaging catheter 452 during activity-state $T_2$ is represented by a trajectory 962. Three-dimensional image 954 of inspected organ 474 is reconstructed from two-dimensional images $964_1$, $964_2$, $964_3$, $964_4$ and $964_5$ detected during activity-state $T_3$. The path of imaging catheter 452 during activity-state $T_3$ is represented by a trajectory 966.

The coordinates of two-dimensional images $956_1$, $956_2$, $956_3$, and $956_4$ are represented by points $968_1$, $968_2$, $968_3$, and $968_4$, respectively. The coordinates of two-dimensional images $960_1$, $960_2$, $960_3$, and $960_4$ are represented by points $970_1$, $970_2$, $970_3$, and $970_4$, respectively. The coordinates of two-dimensional images $964_1$, $964_2$, $964_3$, $964_4$ and $964_5$ are represented by points $972_1$, $972_2$, $972_3$, $972_4$ and $972_5$, respectively.

It is noted that processor 460 computes each of the different trajectories 958, 962 and 966 for the path which imaging catheter supposedly follows inside inspected organ 474, during different activity-states of inspected organ 474. Otherwise, trajectories 958, 962 and 966 belong to the same scanning process, and are traversed during the same time period. Hence, points $968_1$, $970_1$ and $972_1$ which designate the start of trajectories 958, 962 and 966, respectively, belong to the same point in time. Likewise, points $956_4$, $970_4$ and $972_5$ which designate the end of trajectories 958, 962 and 966, respectively, belong to another point in time. Thus, a two-dimensional image which belongs to one activity-state and is located at a certain fraction of the length of one trajectory, can be translated to a respective location on another trajectory and to another activity-state, according to the same fraction of the length of this other trajectory.

With reference to FIG. 25B, two-dimensional image $960_2$ is acquired at activity-state $T_2$ and the coordinates associated therewith, are represented by point $970_2$. Processor 460 determines shifted coordinates for the image $960_2$ on trajectory 958, operating under the assumption that these coordinates would have been detected by the imaging MPS sensor 468, had this image been acquired during activity state $T_1$.

In the present example, processor 460 determines these new coordinates using the fact that the changes in the length of the artery are minor through all of the activity states. Accordingly, the distance of point $970_2$ from point $970_1$ (i.e., from the beginning of trajectory 962), is equal to a fraction b of the entire length of trajectory 962 (i.e., from point $970_1$ to point $970_4$). Processor 460 determines the translated coordinates represented by point $970_{2T}$ on trajectory 958, according to the fraction b of the length of trajectory 958 from point $968_1$. Processor 460, then can use two-dimensional image $960_2$ from activity-state $T_2$ for reconstructing the three-dimensional image associated with activity-state $T_1$, using translated coordinates represented by point $970_{2T}$.

With reference to FIG. 25C, processor 460 reconstructs a three-dimensional image 974 of inspected organ 474 at activity-state $T_1$, in the following manner. Processor 460 translates two-dimensional image $960_2$ from activity-state $T_2$ to activity-state $T_1$, as translated two-dimensional image $960_{2T}$ as described herein above.

Processor 460 determines that point $972_2$ is located at a fraction c of the length of trajectory 966. Processor 460 determines the translated coordinates represented by a point $972_{2T}$ on trajectory 958, according to the same fraction c of the length of trajectory 958. Processor 460, then translates two-dimensional image $964_2$ form activity-state $T_3$ to activity-state $T_1$, as a translated two-dimensional image $964_{2T}$.

Processor 460 determines that point $972_3$ is located at a fraction d of the length of trajectory 966. Processor 460 determines the translated coordinates represented by a point $972_{3T}$ on trajectory 958, according to the same fraction d of the length of trajectory 958. Processor 460, then translates two-dimensional image $964_3$ from activity-state $T_3$ to activity-state $T_1$, as a translated two-dimensional image $964_{3T}$. Likewise, processor 460 determines the translated coordinates represented by points $972_{1T}$, $970_{1T}$, $970_{3T}$, $972_{4T}$, $972_{5T}$ and $970_{4T}$ for translated two-dimensional images $964_{1T}$, $960_{1T}$, $960_{3T}$, $964_{4T}$, $964_{5T}$ and $960_{4T}$, respectively.

In this manner, processor 460 reconstructs three-dimensional image 950 from two-dimensional images $964_{1T}$, $960_{1T}$, $956_1$, $960_{2T}$, $964_{2T}$, $956_2$, $964_{3T}$, $960_{3T}$, $956_3$, $964_{4T}$, $956_4$, $964_{5T}$ and $960_{4T}$ which are substantially greater in number than the original two-dimensional images $956_1$, $956_2$, $956_3$ and $956_4$ (FIG. 25A). Accordingly, processor 460 can reconstruct three-dimensional image 974, which is substantially more detailed than three-dimensional image 950.

With reference to FIG. 25D, processor 460 reconstructs a three-dimensional image 976 for activity-state $T_2$, from the original two-dimensional images $960_1$, $960_2$, $960_3$ and $960_4$ and from additional two-dimensional images which belong to activity-states $T_1$ and $T_3$. Part of these additional two-dimensional images are references $956_1$, $956_2$, $956_3$ and $956_4$ which are translated from activity-state $T_1$ to activity-state $T_2$, as translated two-dimensional images $956_{1T}$, $956_{2T}$, $956_{3T}$ and $956_{4T}$, respectively. Translated two-dimensional images $956_{1T}$, $956_{2T}$, $956_{3T}$ and $956_{4T}$ possess the translated coordinates represented by points $968_{1T}$, $968_{2T}$, $968_{3T}$ and $968_{4T}$, respectively. The other additional two-dimensional images are references $964_1$, $964_2$, $964_3$, $964_4$ and $964_5$ which are translated from activity-state $T_3$ to activity-state $T_2$, as translated two-dimensional images $964_{1T}$, $964_{2T}$, $964_{3T}$, $964_{4T}$ and $964_{5T}$, respectively. Translated two-dimensional images $964_{1T}$, $964_{2T}$, $964_{3T}$, $964_{4T}$ and $964_{5T}$ possess translated coordinates represented by points $972_1$, $972_2$, $972_3$, $972_4$ and $972_5$, respectively.

It is noted that since three-dimensional image 976 is reconstructed from a substantially large number of two-dimensional images, three-dimensional image 976 is substantially more detailed than three-dimensional image 952, which is reconstructed from two-dimensional images which belong only to one activity-state. It is further noted that processor 460 can reconstruct a detailed three-dimensional image for each activity-state, from all the two-dimensional images of all other activity-states, in addition to two-dimensional images which belong to the activity-state under reconstruction.

Figure 26:
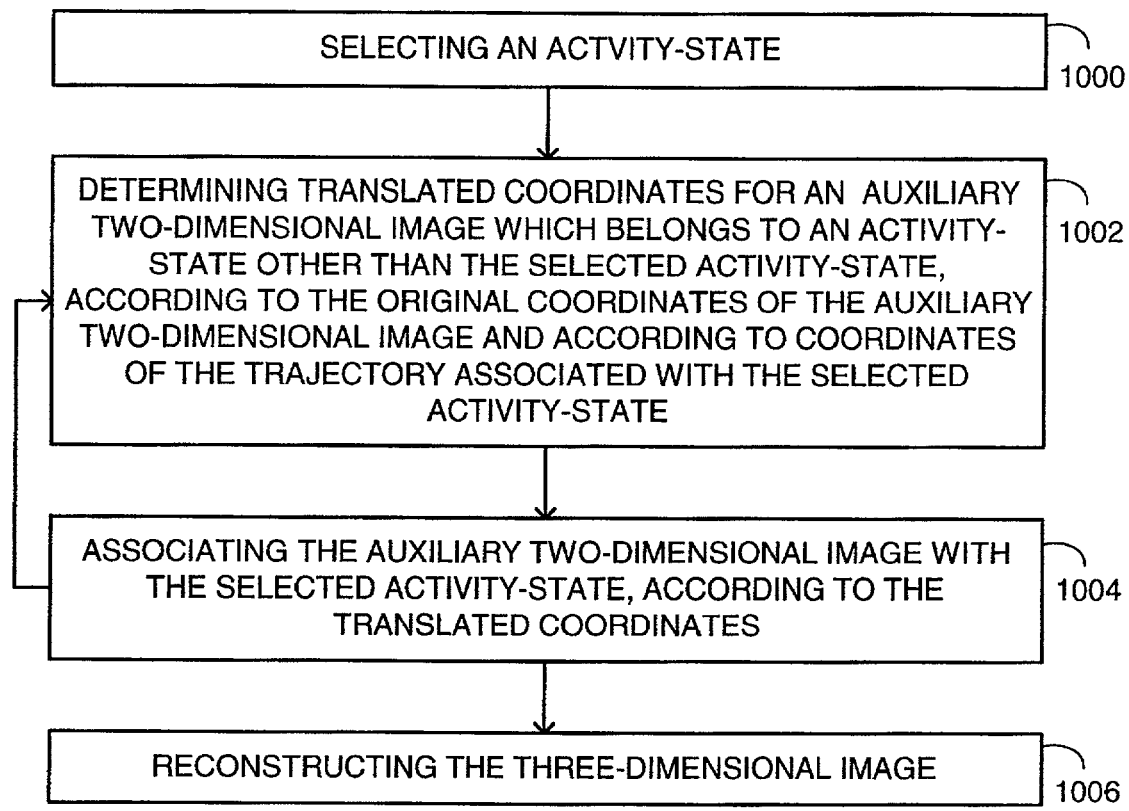
FIG. 26 is a schematic illustration of a method for reconstructing a three-dimensional image, operative according to a further preferred embodiment of the present invention.

Reference is now made to FIG. 26, which is a schematic illustration of a method for reconstructing a three-dimensional image, operative according to a further preferred embodiment of the present invention. In procedure 1000, an activity-state is selected. With reference to FIGS. 14, 15A, 25A and 25C, processor 460 selects activity-state $T_1$, for which three-dimensional image 974 is to be reconstructed.

In procedure 1002, translated coordinates for an auxiliary two-dimensional image, which belongs to an activity-state other than the selected activity-state, are determined according to the original coordinates of the auxiliary two-dimensional image, and according to coordinates of the trajectory associated with the selected activity-state. With reference to FIG. 25B, processor 460 determines the translated coordinates for two-dimensional image $960_2$ represented by point $970_{2T}$, which belongs to activity-state $T_2$. The translated coordinates are determined according to the original coordinates of two-dimensional image $960_2$ represented by point $970_2$ and according to the coordinates of trajectory 958 (i.e., those which are represented by points $968_1$, $968_2$, $968_3$ and $968_4$).

In procedure 1004, the auxiliary two-dimensional image is associated with the selected activity-state, according to the translated coordinates. With reference to FIG. 25B, processor 460 associates two-dimensional image $960_2$ with activity-state $T_1$, as translated two-dimensional image $960_{2T}$, according to the translated coordinates represented by point $970_{2T}$. At this point the method recursively returns back to procedure 1002, until the auxiliary two-dimensional images of all activity-states other than the selected activity-states, are associated with the selected activity-state. With reference to FIG. 25C, two-dimensional images $960_1$, $960_3$, $960_4$, which belong to activity-state $T_2$ and two-dimensional images $964_1$, $964_2$, $964_3$, $964_4$ and $964_5$, which belong to activity-state $T_3$, are associated with activity-state $T_1$, as translated two-dimensional images $960_{1T}$, $960_{3T}$, $960_{4T}$, $964_{1T}$, $964_{2T}$, $964_{3T}$, $964_{4T}$ and $964_{5T}$. The translated coordinates of these translated two-dimensional images are represented by points $970_{1T}$, $970_{3T}$, $970_{4T}$, $972_{1T}$, $972_{2T}$, $972_{3T}$, $972_{4T}$ and $972_{5T}$, respectively.

In procedure 1006, the three-dimensional image is reconstructed. With reference to FIG. 25C, processor 460 reconstructs three-dimensional image 974 from two-dimensional images $956_1$, $956_2$, $956_3$ and $956_4$ and from auxiliary two-dimensional images $960_1$, $960_2$, $960_3$, $960_4$, $964_1$, $964_2$, $964_3$, $964_4$ and $964_5$.

Figure 27B:
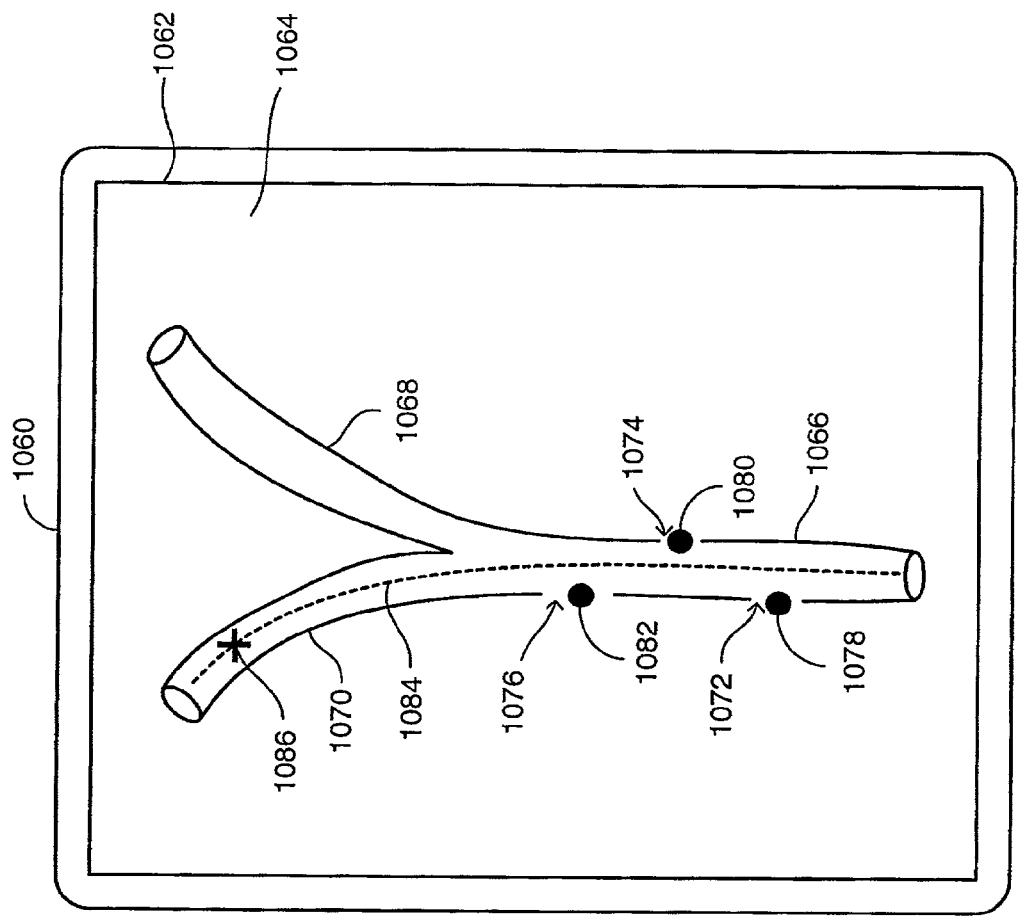
FIG. 27B is a schematic illustration of a GUI, constructed and operative according to another preferred embodiment of the present invention.
Figure 27A:
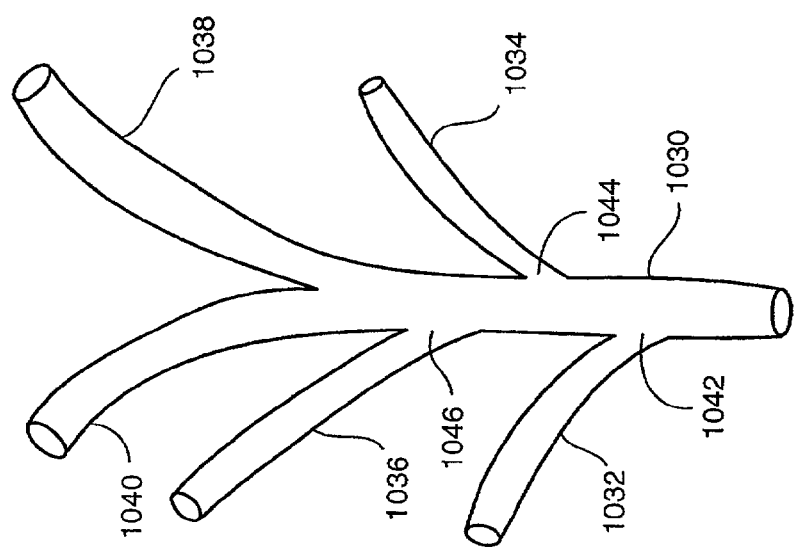
FIG. 27A is an illustration of a section of a vessel, which includes a plurality of branches.

Reference is now made to FIGS. 27A and 27B. FIG. 27A is an illustration of a section of a vessel, generally referenced 1030, which includes a plurality of branches. Vessel 1030 can be a section of an artery, vein, bronchus, and the like, which includes a plurality of bifurcations. FIG. 27B is a schematic illustration of a graphical user interface (GUI), generally referenced 1060, constructed and operative according to another preferred embodiment of the present invention.

With reference to FIG. 27A, vessel 1030 includes side branches 1032, 1034 and 1036, and two main branches 1038 and 1040. Side branches 1032, 1034 and 1036 branch out from vessel 1030 at branching regions 1042, 1044 and 1046, respectively.

With reference to FIG. 27B, GUI 1060 includes a window 1062. Window 1062 includes a three-dimensional image 1064 of vessel 1030. Three-dimensional image 1064 includes a main section 1066, branches 1068 and 1070, a plurality of openings 1072, 1074 and 1076, a plurality of marks 1078, 1080 and 1082, a trajectory 1084 and a representation of a surgical tool 1086. Main section 1066 represents vessel 1030. Branches 1068 and 1070 represent main branches 1038 and 1040, respectively.

Processor 460 (FIG. 15A) reconstructs three-dimensional image 1064 during a scanning process in which the operator scans vessel 1030 and main branches 1038 and 1040, by employing an imaging catheter, such as imaging catheter 452. While the imaging catheter moves inside vessel 1030 and passes branching regions 1042, 1044 and 1046, the image detector of the imaging catheter, such as image detector 470 detects branching regions 1042, 1044 and 1046 as a plurality of openings in the wall of vessel 1030.

GUI 1060 displays branching regions 1042, 1044 and 1046, as openings 1072, 1074 and 1076, respectively. GUI 1060 further displays marks 1078, 1080 and 1082 in the vicinity of openings 1072, 1074 and 1076, respectively, as an indication of branching regions 1042, 1044 and 1046, respectively. Each of marks 1078, 1080 and 1082 can be a polygon, closed curve, open curve, straight line with an end, straight line without an end, different colors, animation, and the like.

Trajectory 1084 indicates one of the paths which the imaging catheter followed inside vessel 1030 during the scanning process. Representation 1086 represents the location and orientation of a surgical tool inside vessel 1030, such as surgical tool 486 (FIG. 16A). By employing GUI 1060, the operator can navigate the surgical tool through vessel 1030, to selected side branches of vessel 1030 during a surgical procedure. It is noted that the system can derive various representations, according to the reconstructed model of the inspected organ, such as an internal model, a quantitative model superposed on a real-time acquired image, and the like.

It will be appreciated by persons skilled in the art that the present invention is not limited to what has been particularly shown and described herein above. Rather the scope of the present invention is defined only by the claims, which follow.

The invention claimed is:

1. Method for displaying an image sequence of a cyclically moving inspected organ that moves according to an organ motion cycle, comprising the steps of:

detecting an organ timing signal of said inspected organ, said organ timing signal including a plurality of occurrences within said organ motion cycle;

acquiring during said procedure of detecting a plurality of two-dimensional images of said inspected organ from different locations and orientations using an image detector;

detecting for each of said two-dimensional images acquired a respective location and orientation of said image detector;

associating each of said two-dimensional images with its corresponding respective image detector location and orientation and with a reading of said organ timing signal, which was detected at the same time as the acquisition of a said two-dimensional image, each said reading corresponding to a certain point in said organ motion cycle;

sorting said two-dimensional images into groups according to said cycle points in said organ motion cycle which correspond to the associated organ timing signal reading corresponding to a certain cycle point in said organ motion cycle;

reconstructing for each said group of two-dimensional images, a three-dimensional image based on the location and orientation associated with each of said two-dimensional images in a group, each said reconstructed three dimensional images being associated with respective cycle points of said organ motion cycle of said group;

detecting a real-time organ timing signal of said inspected organ at a time later than the detection of said organ timing signal;

identifying real-time cycle points within said real-time organ timing signal;

selecting for each said identified real-time cycle point one of said reconstructed three-dimensional images associated with a cycle point which corresponds to said identified real-time cycle point; and displaying in real-time a sequence of said selected three-dimensional images.

2. The method according to claim 1, further comprising the following procedures, after said procedure of selecting: detecting the location and orientation of a surgical tool; and superimposing a representation of said surgical tool onto said selected three-dimensional image, according to said detected location and orientation of said surgical tool.

3. The method according to claim 2, wherein said detected location and orientation of said surgical tool and said detected location and orientation of said image detector, both reside in a single coordinate system.

4. The method according to claim 2, wherein said surgical tool is selected from the list consisting of: clamp; laser cutter; brush; catheter; stent; balloon; pace maker electrode; solution dispensing unit; neuron electrode; substance collection unit; surgical delivery tool; gene delivery tool; drug delivery tool; device delivery tool; ablation catheter; endoscope; electrophysiological mapping device; imaging device; and a combination thereof.

5. The method according to claim 2, wherein said representation of said surgical tool indicates an estimated location of said surgical tool.

6. The method according to claim 2, wherein said representation of said surgical tool indicates the orientation of said surgical tool.

7. The method according to claim 2, wherein said representation of said surgical tool is in the form of a cursor.

8. The method according to claim 2, wherein said representation of said surgical tool is a pseudo realistic visualization of said surgical tool.

9. The method according to claim 2, wherein said representation of said surgical tool comprises a projection of a three-dimensional representation of said representation of said surgical tool, on a real time image.

10. The method according to claim 1, further comprising the following procedures, after said procedure of selecting: detecting the location and orientation of a surgical tool; and superimposing a representation of said detected location and orientation of said surgical tool, onto said selected three-dimensional image.

11. The method according to claim 1, further comprising the following procedures, prior to said procedure of displaying: detecting a real time image; and superimposing a projection of said selected three-dimensional image, onto said detected real time image.

12. The method according to claim 1, wherein said procedure of reconstruction is performed further according to the location and orientation information associated with each said selected two-dimensional images.

* * * * *